United States Patent
Bloxham et al.

(10) Patent No.: US 8,278,442 B2
(45) Date of Patent: Oct. 2, 2012

(54) BICYCLIC ARYL AND HETEROARYL COMPOUNDS FOR THE TREATMENT OF METABOLIC DISORDERS

(75) Inventors: Jason Bloxham, Oxford (GB); Stuart Edward Bradley, Oxford (GB); Tom Banksia Dupree, Oxford (GB); Peter Timothy Fry, Oxford (GB); Patrick Eric Hanrahan, Oxford (GB); Thomas Martin Krulle, Oxford (GB); Martin James Procter, Oxford (GB); Colin Peter Sambrook-Smith, Oxford (GB); Karen Lesley Schofield, Oxford (GB); Donald Smyth, Oxford (GB); Alan John Stewart, Oxford (GB)

(73) Assignee: Prosidion Limited, Oxford (GB)

( * ) Notice: Subject to any disclaimer, the term of this patent is extended or adjusted under 35 U.S.C. 154(b) by 0 days.

(21) Appl. No.: 12/601,100

(22) PCT Filed: May 22, 2008

(86) PCT No.: PCT/GB2008/050370
§ 371 (c)(1),
(2), (4) Date: Mar. 11, 2010

(87) PCT Pub. No.: WO2008/142454
PCT Pub. Date: Nov. 27, 2008

(65) Prior Publication Data
US 2010/0173886 A1    Jul. 8, 2010

(30) Foreign Application Priority Data

May 22, 2007   (GB) ................................ 0709789.2
Jan. 11, 2008   (GB) ................................ 0800454.1

(51) Int. Cl.
C07D 213/84   (2006.01)
C07D 217/22   (2006.01)
C07D 403/12   (2006.01)
C07D 413/12   (2006.01)

(52) U.S. Cl. ......... 544/131; 544/365; 546/141; 546/288
(58) Field of Classification Search .................. None
See application file for complete search history.

(56) References Cited

U.S. PATENT DOCUMENTS

| | | | |
|---|---|---|---|
| 6,028,175 | A | 2/2000 | Grandy et al. |
| 6,225,080 | B1 | 5/2001 | Uhl et al. |
| 2006/0217372 | A1* | 9/2006 | Blanco-Pillado et al. .. 514/227.5 |
| 2010/0113512 | A1 | 5/2010 | Ignar |
| 2010/0173886 | A1 | 7/2010 | Bloxham et al. |

FOREIGN PATENT DOCUMENTS

| | | |
|---|---|---|
| EP | 0843726 B1 | 5/1998 |
| WO | WO-9507983 A1 | 3/1995 |
| WO | WO-9707212 A1 | 2/1997 |
| WO | WO-03101963 A1 | 12/2003 |
| WO | WO-2004026305 A1 | 4/2004 |
| WO | WO 2004/080968 A1 * | 9/2004 |
| WO | WO-2004080996 A1 | 9/2004 |
| WO | WO-2005061442 A1 | 7/2005 |
| WO | WO-2005066164 A1 | 7/2005 |
| WO | WO-2005090286 A1 | 9/2005 |
| WO | WO-2005090303 A1 | 9/2005 |
| WO | WO-2005090337 A1 | 9/2005 |
| WO | WO-2005092836 A1 | 10/2005 |
| WO | WO-2007047397 A2 | 4/2007 |
| WO | WO-2008021849 A2 | 2/2008 |
| WO | WO-2008021851 A2 | 2/2008 |
| WO | WO-2008032156 A1 | 3/2008 |
| WO | WO-2008059335 A1 | 5/2008 |

OTHER PUBLICATIONS

Diaz et al., "SAR and biological evaluation of novel *trans*-3,4-dimethyl-4-arylpiperidine derivatives as opioid antagonists", *Bioorg. Med. Chem. Lett.*, 15:3844-3848 (2005).
Takeuchi et al., "Structure-activity relationship studies of carboxamido-biaryl ethers as opioid receptor antagonists (OpRAs). Part I", *Bioorg. Med. Chem. Lett.*, 17:5349-5352 (2007).
Takeuchi et al., "Structure-activity relationship studies of carboxamido-biaryl ethers as opioid receptor antagonists (OpRAs). Part 2", *Bioorg. Med. Chem. Lett.*, 17:6841-6846 (2007).
Zhang et al., "The µ-opioid receptor subtype is required for the anorectic effect of an opioid receptor antagonist", *Eur. J. Pharmacol.*, 545:147-152 (2006).

* cited by examiner

*Primary Examiner* — Janet Andres
*Assistant Examiner* — Timothy R Rozof
(74) *Attorney, Agent, or Firm* — Mintz Levin Cohn Ferris Glovsky and Popeo, P.C.; Ivor R. Elrifi; Heidi A. Erlacher

(57) ABSTRACT

Compounds of formula (I): or pharmaceutically acceptable salts thereof, are opioid receptor modulators, e.g. mu-opioid receptor antagonists, neutral antagonists or inverse agonists, and are useful for the treatment of metabolic disorders including obesity.

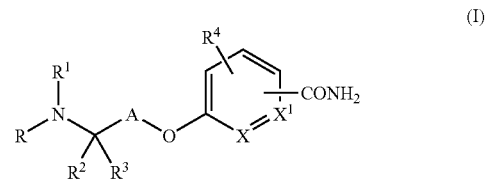

12 Claims, No Drawings

BICYCLIC ARYL AND HETEROARYL COMPOUNDS FOR THE TREATMENT OF METABOLIC DISORDERS

BACKGROUND OF THE INVENTION

The present invention is directed to bicyclic aryl and heteroaryl compounds which are opioid receptor modulators, e.g. mu-opioid receptor antagonists, that are useful for the treatment of metabolic disorders including obesity.

Obesity is characterized by an excessive adipose tissue mass relative to body size. Clinically, body fat mass is estimated by the body mass index (BMI; weight (kg)/height (m)$^2$), or waist circumference. Individuals are considered obese when the BMI is greater than 30 and there are established medical consequences of being overweight. It has been an accepted medical view for some time that an increased body weight, especially as a result of abdominal body fat, is associated with an increased risk for diabetes, hypertension, heart disease, and numerous other health complications, such as arthritis, stroke, gallbladder disease, muscular and respiratory problems, back pain and even certain cancers.

Pharmacological approaches to the treatment of obesity have been mainly concerned with reducing fat mass by altering the balance between energy intake and expenditure. Many studies have clearly established the link between adiposity and the brain circuitry involved in the regulation of energy homeostasis. Direct and indirect evidence suggest that serotonergic, dopaminergic, adrenergic, cholinergic, endocannabinoid, opioid, and histaminergic pathways in addition to many neuropeptide pathways (e.g. neuropeptide Y and melanocortins) are implicated in the central control of energy intake and expenditure. Hypothalamic centres are also able to sense peripheral hormones involved in the maintenance of body weight and degree of adiposity, such as insulin and leptin, and fat tissue derived peptides.

There is a continuing need for novel antiobesity agents, particularly ones that are well tolerated with few adverse effects.

Mu-, kappa- and delta-opioid receptors have been implicated in a number of disease states and their modulation is a potential target for therapeutic intervention.

Antagonists of opioid receptors, in particular the mu-opioid receptor have been shown to reduce body weight in animal models of obesity (J. Zhang et al, *European Journal of Pharmacology*, 454 (2006) 147-152).

Antagonists of opioid receptors have thus been suggested as useful for the treatment of obesity and related disorders, and other diseases or disorders including substance abuse, alcohol abuse, compulsive gambling, depression, opiate overdose, septic shock, irritable bowel syndrome, nausea, vomiting and stroke.

International Patent Applications WO2004/026305 and WO2004/080968 describe diaryl ethers as opioid receptor antagonists.

There remains a need to provide further opioid receptor modulators for the treatment of diseases associated with opioid receptors, for example obesity.

SUMMARY OF THE INVENTION

Compounds of formula (I):

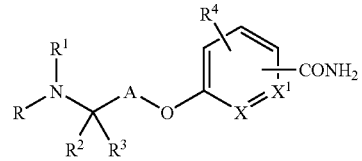

or pharmaceutically acceptable salts thereof, are opioid receptor modulators, e.g. mu-opioid receptor antagonists, neutral antagonists or inverse agonists, and are useful inter alia for the treatment of metabolic disorders including obesity.

DETAILED DESCRIPTION OF THE INVENTION

The present invention is directed to a compound of formula (I):

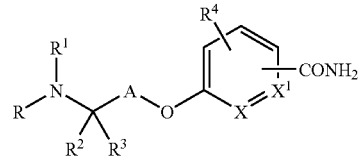

wherein X and $X^1$ are independently CH or N, provided that X and $X^1$ are not both N, and wherein when X is CH the H may be replaced by the $R^4$ group or where $X^1$ is CH the H may be replaced by the $R^4$ group or the —$CONH_2$ substituent;

A is selected from:

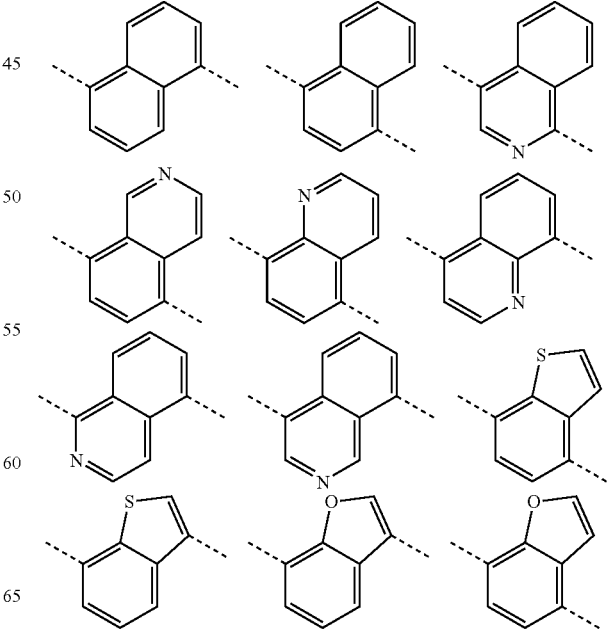

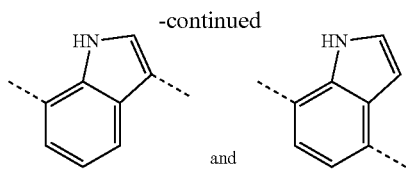
and wherein A is optionally substituted with one to three groups selected from nitrile, $C_1$-$C_3$ alkyl, $C_1$-$C_3$ alkoxy, halo, $C_1$-$C_3$ haloalkyl, $C_1$-$C_3$ haloalkoxy, —C(O)$C_1$-$C_3$ alkyl, $C_3$-$C_8$ cycloalkyl and —$C_1$-$C_3$ alkyl $C_3$-$C_8$ cycloalkyl;

R is hydrogen, $C_1$-$C_6$ alkyl or —$C_2$-$C_3$ alkylO$C_1$-$C_3$ alkyl;

$R^1$ is $C_1$-$C_6$ alkyl, $C_3$-$C_6$ alkenyl, —$C_1$-$C_6$ alkylaryl, $C_3$-$C_{10}$ cycloalkyl, —$C_1$-$C_6$ alkyl $C_3$-$C_{10}$ cycloalkyl, $C_3$-$C_9$ heterocyclyl, —$C_2$-$C_6$ alkyl-O—$C_3$-$C_9$ heterocyclyl, —$C_1$-$C_6$ alkyl $C_3$-$C_9$ heterocyclyl, —$C_2$-$C_6$ alkyl-O—$C_3$-$C_{10}$ cycloalkyl, —$C_2$-$C_6$ alkyl-O—$C_5$-$C_{10}$ heteroaryl, —$C_1$-$C_6$ alkyl $C_5$-$C_{10}$ heteroaryl, —$C_1$-$C_6$ alkylC(O)$C_1$-$C_6$ alkyl, —$C_1$-$C_6$ alkylC(O)$C_3$-$C_9$ heterocyclyl, —$C_1$-$C_6$ alkylC(O) aryl, —$C_2$-$C_6$ alkyl-O-aryl, —$C_2$-$C_6$ alkyl-O—$C_1$-$C_6$ alkyl, —$C_2$-$C_6$ alkylNR$^6$R$^7$, —(CH$_2$)$_m$C(O)NR$^6$R$^7$ and —(CH$_2$)$_m$NSO$_2$R$^5$; wherein each of the alkyl, alkenyl, cycloalkyl, heterocyclyl, heteroaryl and aryl groups are optionally substituted with one to three groups selected from halo, nitrile, $C_1$-$C_6$ haloalkyl, —S(O)$_n$$C_1$-$C_6$ alkyl, $C_1$-$C_6$ alkyl, $C_2$-$C_6$ alkenyl, $C_2$-$C_6$ alkynyl, aryl, —$C_1$-$C_6$ alkylaryl, —C(O)$C_1$-$C_6$ alkyl, $C_1$-$C_6$ alkoxy, —O—$C_1$-$C_6$ haloalkyl and hydroxy;

or R and R$^1$ may together with the N atom to which they are attached form a 4- to 7-membered heterocyclic ring optionally containing one further heteroatom selected from N, O and S, which ring may be substituted by one to five groups selected from NR$^8$R$^9$, $C_1$-$C_6$ alkyl, $C_2$-$C_6$ alkenyl, $C_2$-$C_6$ alkynyl, aryl, hydroxy, halo, —$C_1$-$C_6$ alkylaryl, —$C_1$-$C_6$ alkoxy, —$C_1$-$C_6$ alkoxyaryl, aryloxy, —C(O)$C_1$-$C_6$ alkyl, oxo, $C_1$-$C_6$ haloalkyl and —O—(CH$_2$)$_2$—O—, wherein any aryl groups are optionally substituted with one to three halo groups;

$R^2$ and $R^3$ are independently hydrogen or $C_1$-$C_3$ alkyl;

$R^4$ is hydrogen, $C_1$-$C_3$ alkyl, $C_1$-$C_3$ alkoxy, halo, $C_1$-$C_3$ haloalkyl, —C(O)$C_1$-$C_3$ alkyl, —$C_1$-$C_3$ alkyl $C_3$-$C_8$ cycloalkyl or $C_1$-$C_3$ haloalkoxy;

$R^5$ is $C_1$-$C_6$ alkyl, —$C_1$-$C_6$ alkylaryl or —$C_1$-$C_6$alkyl-O—$C_1$-$C_6$alkyl;

$R^6$ and $R^7$ are independently hydrogen, $C_1$-$C_6$ alkyl, —$C_1$-$C_6$ alkylaryl, $C_3$-$C_8$ cycloalkyl, —$C_1$-$C_6$ alkyl $C_5$-$C_{10}$ heteroaryl, —$C_1$-$C_6$ alkyl $C_3$-$C_7$heterocyclyl, —$C_1$-$C_6$ alkylC(O)$C_1$-$C_6$ alkyl, —$C_1$-$C_6$ alkylC(O)$C_3$-$C_7$heterocyclyl, —$C_1$-$C_6$ alkylC(O)aryl, —$C_1$-$C_6$ alkyl-O-aryl, —$C_2$-$C_6$alkyl-O—$C_1$-$C_6$alkyl, —$C_1$-$C_6$ alkyl $C_3$-$C_9$ cycloalkyl; wherein each of the alkyl, cycloalkyl, heterocyclyl, heteroaryl and aryl groups are optionally substituted with one to three groups selected from halo, $C_1$-$C_6$ haloalkyl, —S(O)$_n$$C_1$-$C_6$ alkyl, $C_1$-$C_6$ alkyl, $C_2$-$C_6$ alkenyl, $C_2$-$C_6$ alkynyl, aryl, —$C_1$-$C_6$ alkylaryl, —C(O)$C_1$-$C_6$ alkyl, $C_1$-$C_6$ alkoxy and $C_1$-$C_6$ haloalkoxy;

or $R^6$ and $R^7$ may together with the N atom to which they are attached form a 4- to 7-membered heterocyclic ring optionally containing one further heteroatom selected from N, O and S, which ring may be substituted by one to three groups selected from NR$^8$R$^9$, $C_1$-$C_6$ alkyl, $C_2$-$C_6$ alkenyl, $C_2$-$C_6$ alkynyl, aryl, hydroxy, halo, —$C_1$-$C_6$ alkylaryl, —C(O)$C_1$-$C_6$ alkyl, oxo and $C_1$-$C_6$ haloalkyl;

$R^8$ and $R^9$ are independently hydrogen or $C_1$-$C_6$ alkyl;

n is 0, 1, or 2; and m is 1, 2 or 3;

provided that the —CONH$_2$ substituent is not ortho to the —O— group on the phenyl or pyridyl ring.

In the compounds of formula (I):

The —CONH$_2$ substituent is preferably para to the —O— group on the phenyl or pyridyl ring.

It is understood that when the group A contains a heteroatom it may be linked through the points of attachment to the rest of the molecule in two possible configurations forming regioisomers, thus, for example, the compounds of formula (I) encompass the regioisomers shown below:

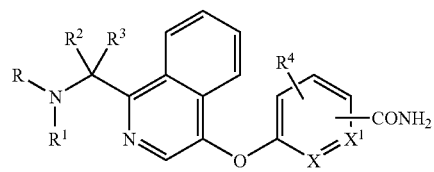

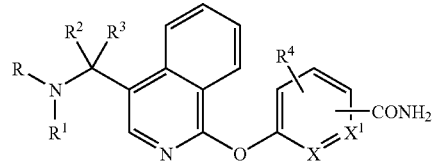

A is preferably selected from:

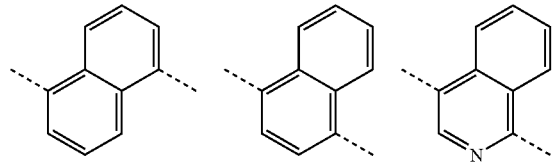

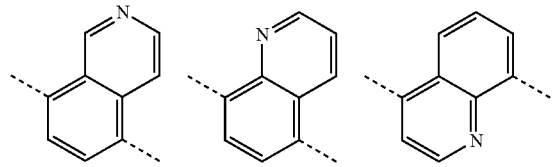

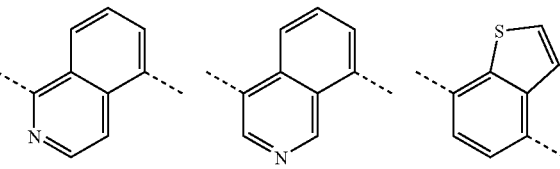

and

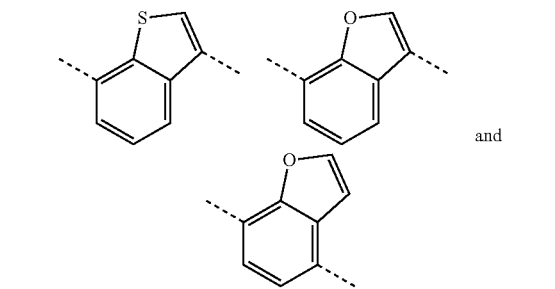

A is more preferably selected from:

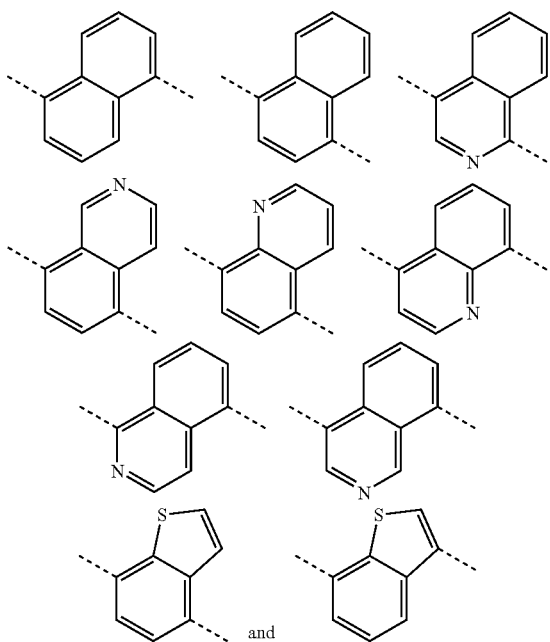

Particular A groups which may be mentioned are:

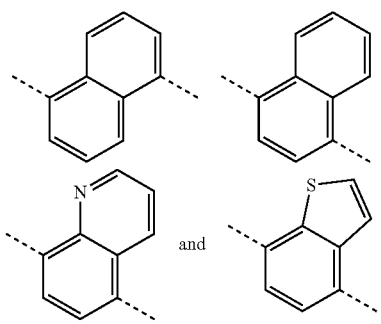

R is preferably hydrogen or $C_1$-$C_3$ alkyl.

Particular $R^1$ groups which may be mentioned are $C_1$-$C_6$ alkyl, $C_3$-$C_6$ alkenyl, —$C_1$-$C_6$ alkylaryl, $C_3$-$C_{10}$ cycloalkyl, —$C_1$-$C_6$ alkyl $C_3$-$C_{10}$ cycloalkyl, $C_3$-$C_7$ heterocyclyl, —$C_2$-$C_6$ alkyl-O—$C_3$-$C_7$ heterocyclyl, —$C_1$-$C_6$ alkyl $C_3$-$C_7$ heterocyclyl, —$C_2$-$C_6$ alkyl-O—$C_3$-$C_{10}$ cycloalkyl, —$C_2$-$C_6$ alkyl-O—$C_5$-$C_{10}$ heteroaryl, —$C_1$-$C_6$ alkyl $C_5$-$C_{10}$ heteroaryl, —$C_1$-$C_6$ alkylC(O)$C_1$-$C_6$ alkyl, —$C_1$-$C_6$ alkylC(O)$C_3$-$C_7$ heterocyclyl, —$C_1$-$C_6$ alkylC(O)aryl, —$C_2$-$C_6$ alkyl-O-aryl, —$C_2$-$C_6$ alkyl-O—$C_1$-$C_6$ alkyl, —$C_2$-$C_6$ alkylNR$^6$R$^7$, —$(CH_2)_mC(O)NR^6R^7$ and —$(CH_2)_mNSO_2R^5$; wherein each of the alkyl, alkenyl, cycloalkyl, heterocyclyl, heteroaryl and aryl groups are optionally substituted with one to three groups selected from halo, nitrile, $C_1$-$C_6$ haloalkyl, —$S(O)_nC_1$-$C_6$ alkyl, $C_1$-$C_6$ alkyl, $C_2$-$C_6$ alkenyl, $C_2$-$C_6$ alkynyl, aryl, —$C_1$-$C_6$ alkylaryl, —C(O)$C_1$-$C_6$ alkyl, $C_1$-$C_6$ alkoxy, —O—$C_1$-$C_6$ haloalkyl and hydroxy;

$R^1$ is preferably $C_1$-$C_6$ alkyl, —$C_1$-$C_6$ alkylaryl, $C_3$-$C_{10}$ cycloalkyl, —$C_1$-$C_6$ alkyl $C_3$-$C_{10}$ cycloalkyl, $C_3$-$C_7$ heterocyclyl, —$C_1$-$C_6$ alkyl $C_3$-$C_7$ heterocyclyl or —$C_1$-$C_6$ alkyl $C_5$-$C_{10}$ heteroaryl; wherein each of the alkyl, cycloalkyl, heterocyclyl, heteroaryl and aryl groups are optionally substituted with one or two groups as described above.

$R^1$ is more preferably $C_1$-$C_6$ alkyl or $C_3$-$C_{10}$ cycloalkyl.

A further preferred group of compounds are those where R and $R^1$ together with the N atom to which they are attached form a 4- to 7-membered heterocyclic ring, which ring may be substituted by one to three groups selected from NR$^8$R$^9$, $C_1$-$C_6$ alkyl, $C_2$-$C_6$ alkenyl, $C_2$-$C_6$ alkynyl, aryl, hydroxy, halo, —$C_1$-$C_6$ alkylaryl, —$C_1$-$C_6$ alkoxy, —$C_1$-$C_6$ alkoxyaryl, aryloxy, —C(O)$C_1$-$C_6$ alkyl, oxo and $C_1$-$C_6$ haloalkyl, wherein any aryl groups are optionally substituted with one to three halo groups.

When R and $R^1$ together with the N atom to which they are attached form a 4- to 7-membered heterocyclic ring optionally containing one further heteroatom selected from N, O and S, a particular group of substituents with which said ring may be substituted are one to three groups selected from NR$^8$R$^9$, $C_1$-$C_6$ alkyl, $C_2$-$C_6$ alkenyl, $C_2$-$C_6$ alkynyl, aryl, hydroxy, halo, —$C_1$-$C_6$ alkylaryl, —C(O)$C_1$-$C_6$ alkyl, oxo and $C_1$-$C_6$ haloalkyl.

At least one of $R^2$ and $R^3$ is preferably hydrogen, more preferably $R^2$ and $R^3$ are both hydrogen.

$R^4$ is preferably hydrogen or fluoro, e.g. hydrogen.

$R^4$ is preferably para to the —O— group on the phenyl or pyridyl ring.

$X^1$ is preferably CH.

X is preferably CH, N or CF, e.g. N or CF.

The molecular weight of the compounds of formula (I) is preferably less than 800, more preferably less than 600, even more preferably less than 500.

While the preferred groups for each variable have generally been listed above separately for each variable, preferred compounds of this invention include those in which several or each variable in formula (I) is selected from the preferred groups for each variable. Therefore, this invention is intended to include all combinations of preferred listed groups.

Specific compounds of the invention which may be mentioned are those included in the Examples as the free base or pharmaceutically acceptable salts thereof.

As used herein, unless stated otherwise, "alkyl" as well as other groups having the prefix "alk" such as, for example, alkoxy, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

The term "haloalkyl" includes alkyl groups substituted by one or more halo, e.g. fluoro atoms, such as $CH_2F$, $CHF_2$ and $CF_3$.

The term "halo" includes fluorine, chlorine, bromine and iodine atoms.

The term "cycloalkyl" means carbocycles containing no heteroatoms, and includes monocyclic mono-, bi-, and tricyclic saturated carbocycles, as well as fused and bridged systems. Such fused ring systems can include one ring that is partially or fully unsaturated, such as a benzene ring, to form fused ring systems, such as benzofused carbocycles. Cycloalkyl includes such fused ring systems as spirofused ring systems. Examples of cycloalkyl and carbocyclic rings include cyclopropyl, cyclobutyl, cyclopentyl, cyclohexyl, and decahydronaphthyl, adamantyl, indanyl, 1,2,3,4-tetrahydronaphthyl and the like.

The term "aryl" includes phenyl and naphthyl, in particular phenyl.

The term "heterocyclyl" includes 3- to 9-membered, e.g. 3- to 7-membered, saturated monocyclic and bicyclic (including spirofused) rings containing one or two heteroatoms chosen from oxygen, sulfur, and nitrogen. The heteroatoms are not directly attached to one another. Examples of heterocyclic rings include monocyclic rings, for example oxetane, tetrahydrofuran, tetrahydropyran, oxepane, thietane, tetrahydrothiophene, tetrahydrothiopyran, thiepane, azetidine, pyrrolidine, piperidine, azepane, [1,3]dioxane, oxazolidine, piperazine, and the like. Other examples of heterocyclic rings include the oxidised forms of the sulfur-containing rings. Thus, tetrahydrothiophene 1-oxide, tetrahydrothiophene 1,1-dioxide, tetrahydrothiopyran 1-oxide, and tetrahydrothiopyran 1,1-dioxide are also considered to be heterocyclic rings.

The term "heteroaryl" includes mono- and bicyclic 5- to 10-membered, e.g. monocyclic 5- or 6-membered, heteroaryl rings containing up to 4 heteroatoms selected from N, O and S. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl and triazinyl. Bicyclic heteroaryl groups include bicyclic heteroaromatic groups where a 5- or 6-membered heteroaryl ring is fused to a phenyl or another heteroaromatic group. Examples of such bicyclic heteroaromatic rings are benzofuran, benzothiophene, indole, benzoxazole, benzothiazole, indazole, benzimidazole, benzotriazole, quinoline, isoquinoline, quinazoline, quinoxaline and purine.

Compounds described herein may contain one or more asymmetric centers and may thus give rise to enantiomers, diastereomers and optical isomers. The present invention includes all such possible enantiomers, diastereomers as well as their racemic mixtures, their substantially pure resolved enantiomers, all possible geometric isomers, and pharmaceutically acceptable salts thereof. The above formula (I) is shown without a definitive stereochemistry at certain positions. The present invention includes all stereoisomers of formula (I) and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of formula (I) exists, the present invention includes any possible tautomers and pharmaceutically acceptable salts thereof, and mixtures thereof, except where specifically drawn or stated otherwise.

When the compound of formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, oxalic, pamoic, pantothenic, phosphoric, succinic, sulfuric, tartaric, p-toluenesulfonic acid and the like.

Since the compounds of formula (I) are intended for pharmaceutical use they are preferably provided in substantially pure form, for example at least 60% pure, more suitably at least 75% pure, especially at least 95% or 98% pure (% are on a weight for weight basis).

The compounds of formula (I) can be prepared as described below:

Compounds of the formula (I) can be prepared using the method illustrated in Scheme 1:

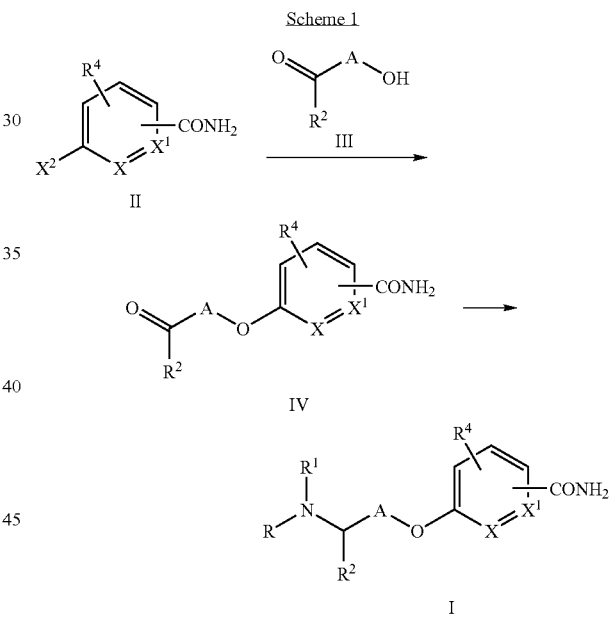

Pyridyl halides of formula (II, $X^2$=F, Cl, X or $X^1$=N) are readily available. Hydroxy aldehydes/ketones of formula (III, $R^2$=H or Alkyl) are either readily available, synthesised by known methods or can be synthesised by the methods shown in Schemes 4, 7, 9, 11, 12 and 13. Pyridyl halides of formula (II) can be reacted with hydroxy carbonyls of formula (III) using a base such as potassium carbonate in a solvent such as DMF to give pyridyl aldehydes/ketones of formula (IV). Reductive amination of aldehydes or ketones of formula (IV) with an amine and a reducing agent such as sodium borohydride in a solvent such as methanol gives compounds of the formula (I).

Alternatively groups may be used in place of the amide that may later be converted to the primary amide through known methods, for example, nitrile.

Compounds of the formula (VIII) can be prepared using the method illustrated in Scheme 2:

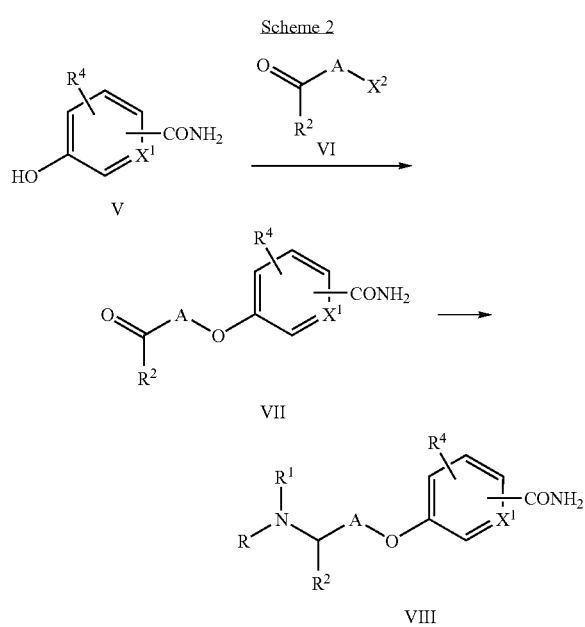

Hydroxy amides of formula (V, $X^1$=N or C) are readily available and halogenated aldehydes/ketones of formula (VI, A is a 1,4-substituted isoquinoline, a 1,5-substituted isoquinoline or a 4,8-substituted quinoline, $X^2$=Hal, $R^2$=H or Alkyl) for example 1-chloro-isoquinoline-4-carbaldehyde can be prepared by known methods (WO01/53274) or other isomers from methods illustrated in Schemes 8 and 10. Hydroxy amides of formula (V) react with aldehydes/ketones of formula (VI) using a base such as potassium carbonate in a solvent such as DMF to give amides of formula (VII). Reductive amination of amides of formula (VII) as described above leads to compounds of formula (VIII).

Compounds of the formula XVI can be prepared using the method illustrated in Scheme 3:

Iodonaphthalenes of formula (IX) (J. A. O'Meara et al., *J. Med. Chem.*, 2005, 48, 5580-5588) can be treated with a cyanide source such as potassium ferrocyanide, a catalyst such as palladium acetate and a base such as sodium carbonate in a solvent such as dimethyl acetamide to give the cyanonaphthalene of formula (X). The cyanonaphthalene of formula (X) can be treated with a reducing agent such as lithium aluminium hydride to give the naphthylamine of formula (XI) which can be reacted with an aldehyde and a reducing agent such as sodium borohydride in a solvent such as methanol to give naphthylamine of formula (XII). Reacting the methoxy naphthylamine of formula (XII) with a Lewis acid such as boron tribromide in a solvent such as dichloromethane removes a methyl to give the hydroxy naphthylalamine of formula (XIII). Reaction of the hydroxy naphthylamine of formula (XIII) with a halogenated pyridine for example a 6-chloronicotinonitrile of formula (XIV), a base such as potassium carbonate and in a solvent such as DMF gives the nitrile amine of formula (XV). Hydrolysis of the nitrile of formula (XV) with for example hydrogen peroxide and potassium carbonate in a solvent such as DMSO gives compounds the formula (XVI).

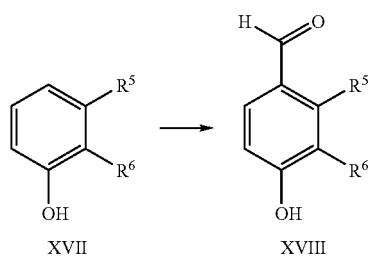

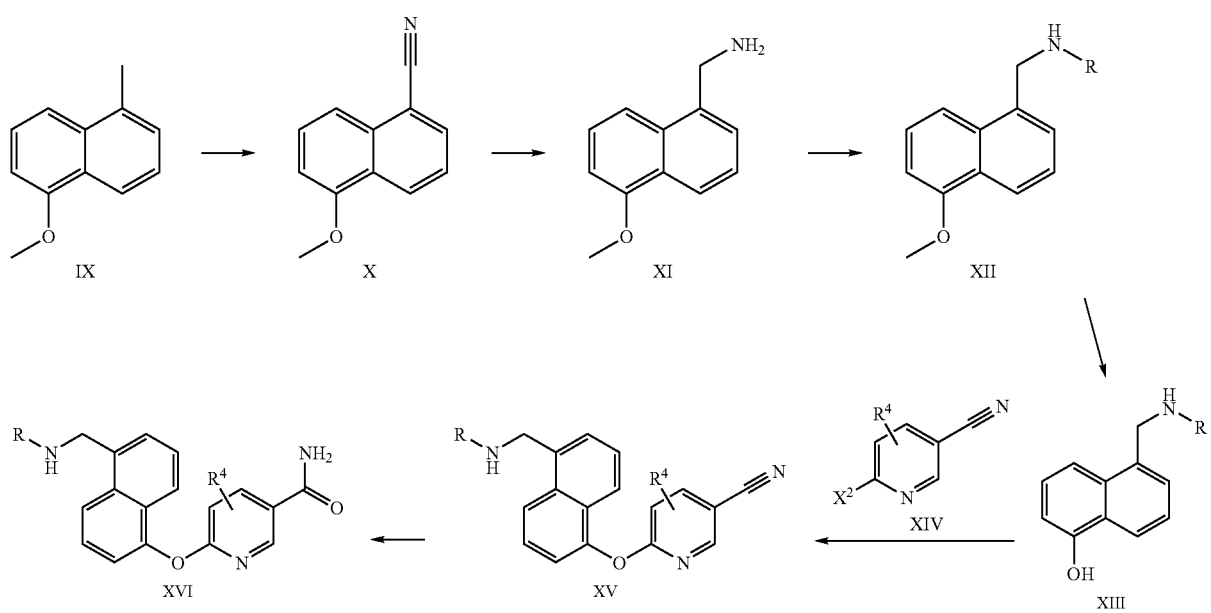

-continued

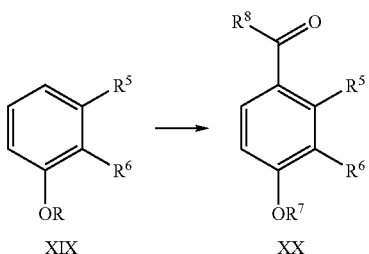

Phenolic compounds of formula (XVII where $R^5$ and $R^6$ form an aromatic ring) can be formylated using the Reimer-Tiemann reaction where treatment with for example chloroform and sodium hydroxide in a solvent such as ethanol/water gives the desired aldehydes of formula (XVIII). Alternatively the Vilsmeier method of treating phenols or methoxy compounds of formula (XIX, $R^7$=H or Me, where $R^5$ and $R^6$ form an aromatic ring) with dimethyl formamide and phosphorous oxylchloride in a solvent such as DCM gives aldehydes of formula (XX, $R^8$=H). Friedel-Crafts reactions of phenols or methoxy compounds of formula (XXII, $R^7$=H or Me) with for example an acyl chloride and a Lewis acid such as aluminium chloride in a solvent such as dichloroethane gives ketones of formula (XX, $R^8$=Alkyl). The methoxy groups can subsequently be removed to give the phenols through known methods.

Phenolic compounds of formula (XVII where $R^5$ and $R^6$ form an aromatic ring) can be hydroxymethylated using for example formaldehyde and sulfuric acid in acetonitrile and then oxidized using known methods to aldehyde of formula (XVIII).

Compounds of the formula (XXVI) can be prepared using the method illustrated in Scheme 5:

Chloro hydroxy isoquinolines of formula (XXI) can be reacted with halogenated pyridines for example a 6-chloronicotinonitrile (XIV), a base such as potassium carbonate and in a solvent such as DMF to give the chloro nitrile of formula (XXII). The chloro nitrile of formula (XXII) can be treated with trimethylboroxine with a base such as potassium carbonate and a catalyst such as palladium tetrakistriphenylphospine in a solvent such as DMF to give the methyl nitrile of formula (XXIII). Hydrolysis of the nitrile of formula (XXIII) with for example hydrogen peroxide and potassium carbonate in a solvent such as DMSO gives methyl amides of formula (XXIV). Oxidation of the methyl amide of formula (XXIV) with for example selenium dioxide in a solvent such as dioxane gives the amide aldehyde of formula (XXV). Reductive amination of the amide aldehyde of formula (XXV) under conditions mentioned previously give compounds of the formula (XXVI).

Compounds of the formula (I) can also be prepared using the method illustrated in Scheme 6:

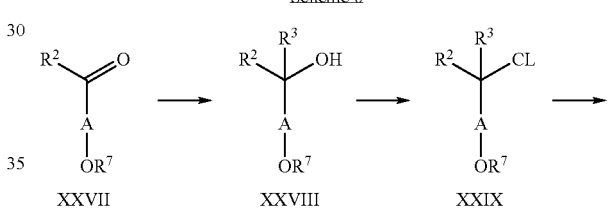

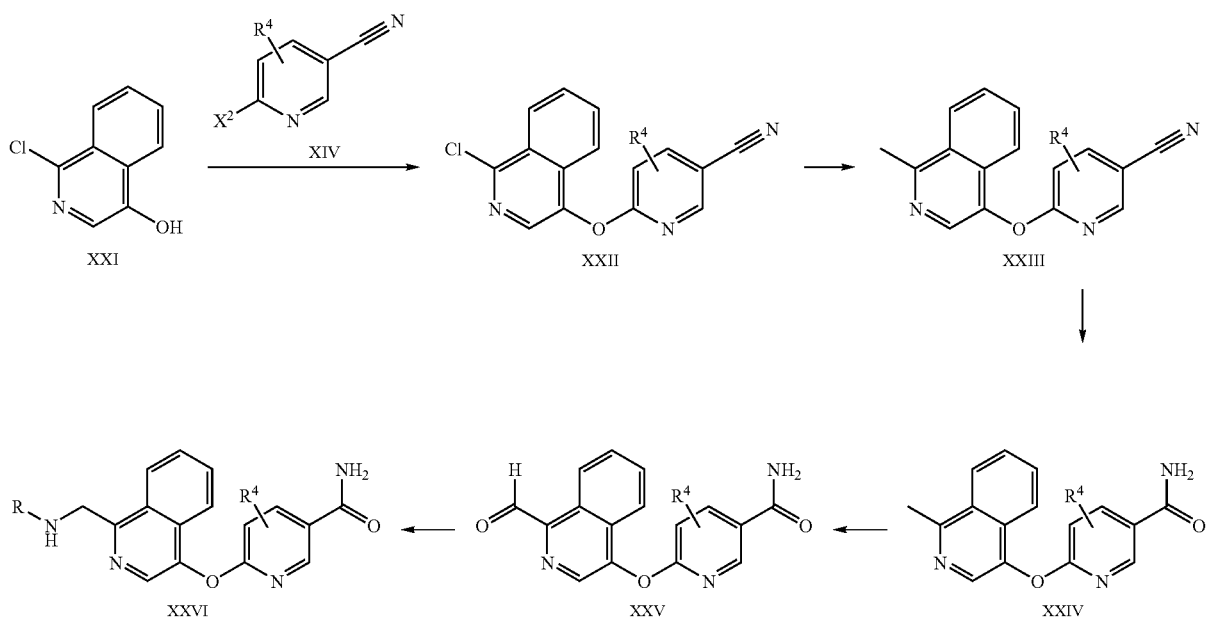

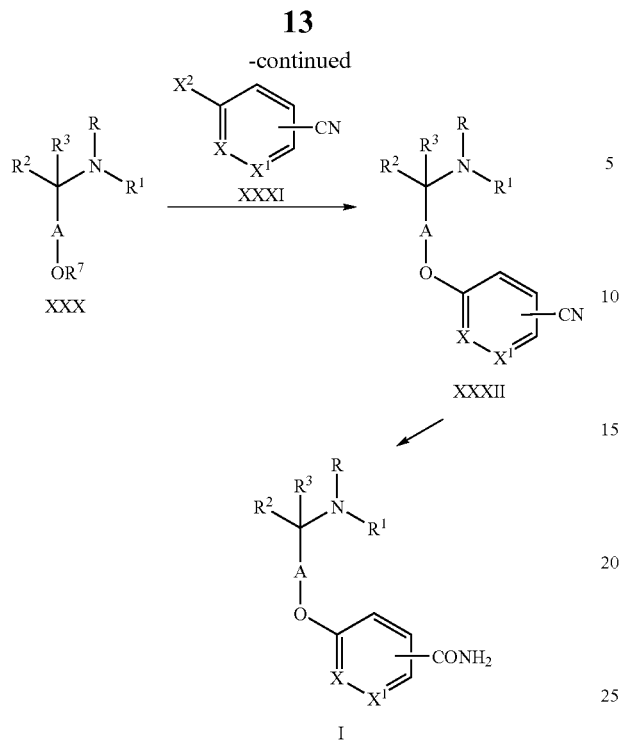

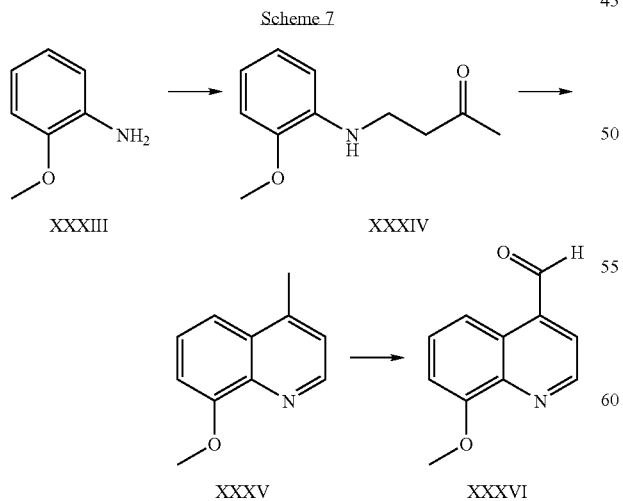

Ketones of formula (XXVII, R²=Alkyl, R⁷=Me) can be treated with organometallic reagents such as alkylmagnesium bromides in a solvent such as THF to give alcohols of the formula (XXVIII). Alcohols of the formula (XXVIII) can be chlorinated by reagents such as thionyl chloride in a solvent such as DCM to give chlorides of the formula (XXIX) which can then be treated with the desired amines in a solvent such as DCM and a base such as triethylamine to give benzylamines of the formula (XXX). Benzylamines of the formula (XXX, R⁷=Me) can then be deprotected with a Lewis acid such as boron tribromide in a solvent such as DCM to give benzylamines of the formula (XXX, R⁷=H). Benzylamines of the formula (XXX, R⁷=H) react with halogenated nitriles of formula (XXXI), a base such as potassium carbonate and in a solvent such as DMF to give the nitrile amine of formula (XXXII). Hydrolysis of the nitrile of formula (XXXII) with for example hydrogen peroxide and potassium carbonate in a solvent such as DMSO gives compounds the formula (I).

Anilines of formula (XXXIII) are readily available and can undergo Michael reactions with methyl vinyl ketone for example in the presence of an acid such as HCl to give secondary anilines of formula (XXXIV). Anilines of formula (XXXIV) can be cyclised under acidic conditions such as polyphosphoric acid to give methyl quinolines of formula (XXXV). Methyl quinolines of formula (XXXV) can be treated with an oxidising agent for example selenium dioxide in a solvent such as dioxane to give aldehydes of the formula (XXXVI). Aldehydes of formula (XXXVI) can then be demethylated as mentioned previously to give hydroxy aldehydes.

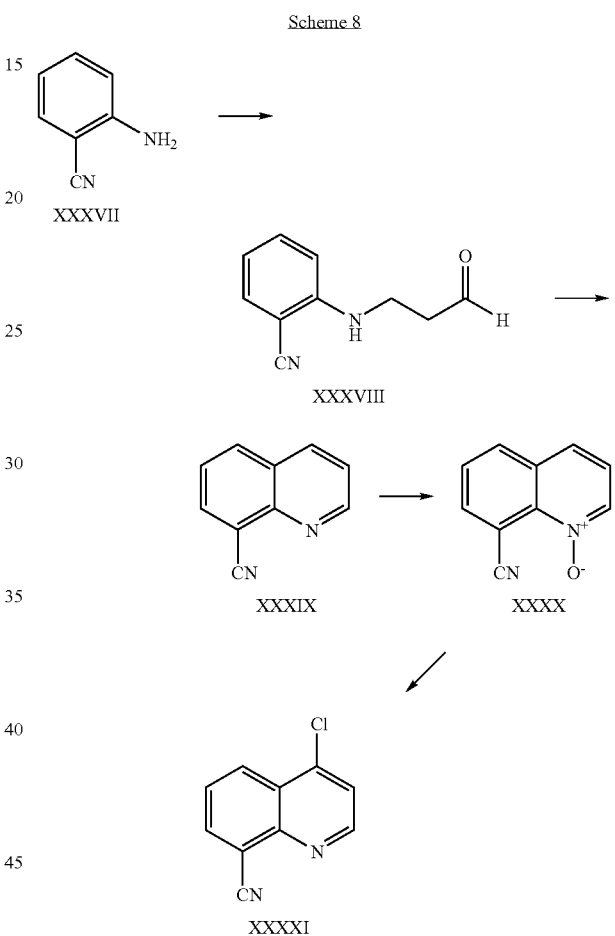

Anilines of formula (XXXVI) are readily available and can undergo Michael reactions with acrolein for example in the presence of an acid such as HCl to give secondary anilines of formula (XXXVIII). Anilines of formula (XXXVIII) can be cyclised under acidic conditions such as polyphosphoric acid to give quinolines of formula (XXXIX). Treatment of anilines of formula (XXXIX) with m-chloroperbenzoic acid in a solvent such as DCM gives N-oxides of formula (XXXX) which can be treated with phosphorus oxychloride to give chloro quinolines of formula (XXXXI). Reduction of the nitrile group in chloro quinolines of formula (XXXXI) with for example lithium aluminium hydride in as solvent such as THF gives the benzylamine or with diisobutylaluminium hydride in toluene gives the aldehyde which can then converted to compounds of formula (I) through previously mentioned chemistry.

Scheme 9

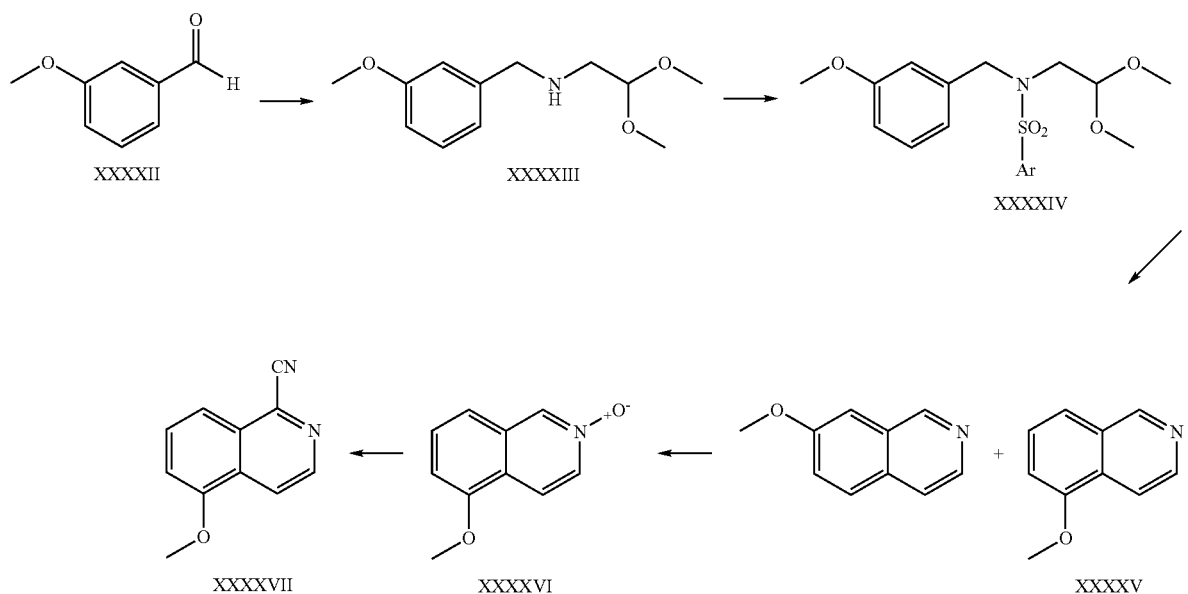

Aldehydes of formula (XXXXII) are readily available and can be treated with amines such as 2,2-dimethoxyethylamine and a reducing agent such as sodium triacteoxyborohydride in a solvent such as DCM to give the secondary amine of formula (XXXXIII). The secondary amine of formula (XXXXIII) can be reacted with p-toluenesulfonyl chloride, a base such as triethylamine and in a solvent such as DCM to give sulfonamides of formula (XXXXIV). Treating the sulfonamide under acid conditions such as polyphosphoric acid gives quinolines of formula (XXXXV) as well as an unwanted isomer. Quinoline of formula (XXXXV) can be treated with m-chloroperbenzoic in a solvent such as DCM to give N-oxides of formula (XXXXVI). N-oxides of formula (XXXXVI) can be treated with diethyl phosphorocyanate in a solvent such as acetonitrile to give nitriles of formula (XXXXVII). Nitriles of formula (XXXXVIII) can be converted to the benzylamine or aldehyde as previously described.

Scheme 10

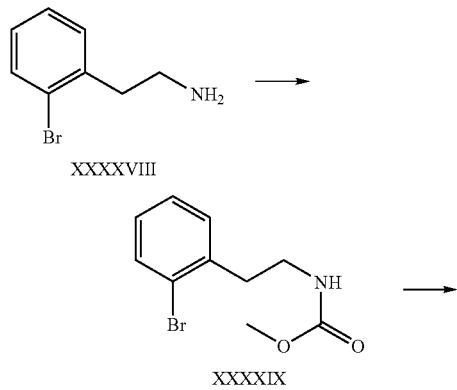

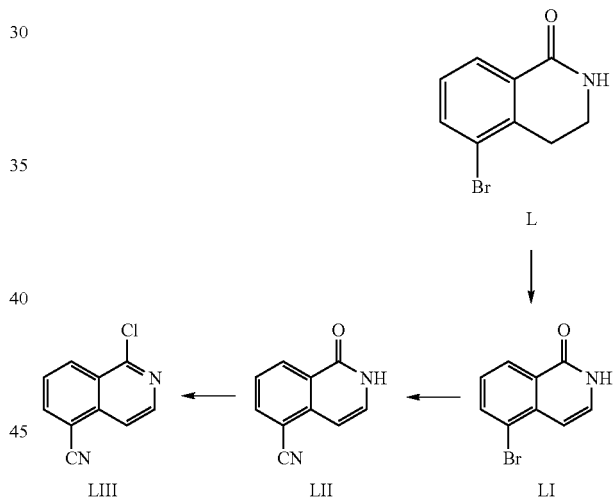

Phenethylamines of formula (XXXXVIII) are commercially available and can be treated with a chloroformate such as methylchloroformate and a base such as triethyamine in a solvent such as DCM to give carbamates of formula (XXXXIX). Carbamates of formula (XXXXIX) upon treatment with acids, such as polyphosphoric acid, cyclise to give cyclic amides of formula (L). Cyclic amides of formula (L) can be oxidised with for example 2,3-dichloro-5,6-dicyano-1,4-benzoquinone in a solvent such as DCM to give bromo isoquinolinones of formula (LI). Bromo isoquinolinones of formula (LI) can be treated with zinc cyanide, a palladium catalyst such as palladium tetrakistriphenylphosphine and in a solvent such as DMF to give nitriles of formula (LII). Nitriles of formula (LII) can be treated with a chlorinating agent such as phosphorous oxychloride to give chloro quinolines of formula (LIII) which can be further manipulated as previously described.

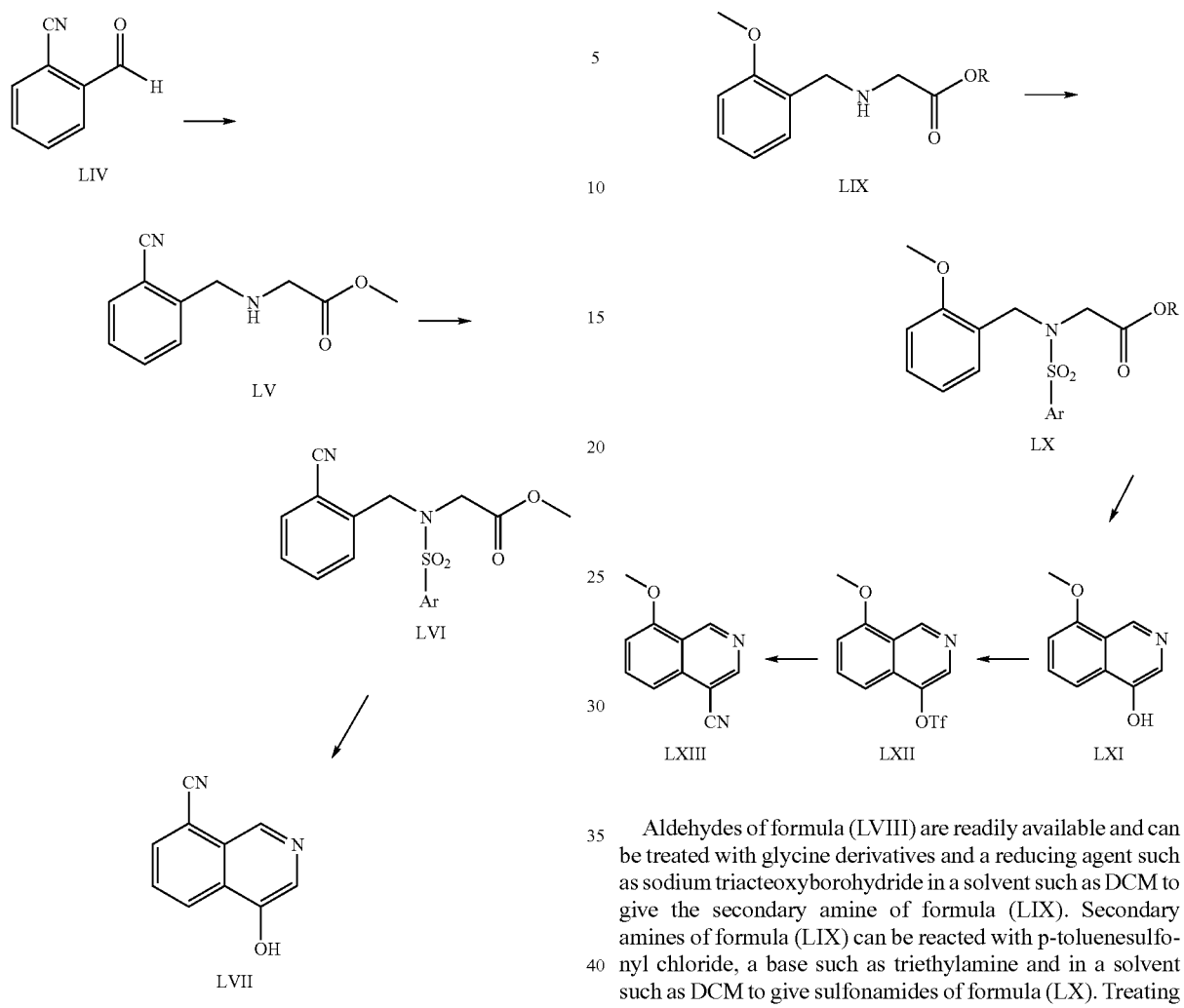

Aldehydes of formula (LIV) are readily available and can be and can be treated with amines such as 2,2-dimethoxyethylamine and a reducing agent such as sodium triacteoxyborohydride in a solvent such as DCM to give secondary amines of formula (LV). Secondary amines of formula (LV) can be reacted with p-toluenesulfonyl chloride, a base such as triethylamine and in a solvent such as DCM to give sulfonamides of formula (LVI). Treating sulfonamides of formula (LVI) under acid conditions such as polyphosphoric acid gives quinolines of formula (LVII) which can be manipulated as previously described.

Aldehydes of formula (LVIII) are readily available and can be treated with glycine derivatives and a reducing agent such as sodium triacteoxyborohydride in a solvent such as DCM to give the secondary amine of formula (LIX). Secondary amines of formula (LIX) can be reacted with p-toluenesulfonyl chloride, a base such as triethylamine and in a solvent such as DCM to give sulfonamides of formula (LX). Treating sulfonamides of formula (LX) under acid conditions such as polyphosphoric acid gives quinolines of formula (LX). Quinolines of formula (LX) can be treated with a triflating agent such as trifluoromethanesulfonic anhydride, a base such as triethylamine and in a solvent such as DCM to give triflates of formula (LXII). Treatment of triflates of formula (LXII) with zinc cyanide, a palladium catalyst such as palladium tetrakistriphenylphosphine and in a solvent such as DMF gives nitriles of formula (LXIII). Nitriles of formula (LXIII) can be manipulated as previously described.

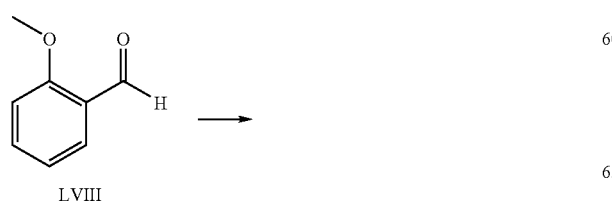

Scheme 12

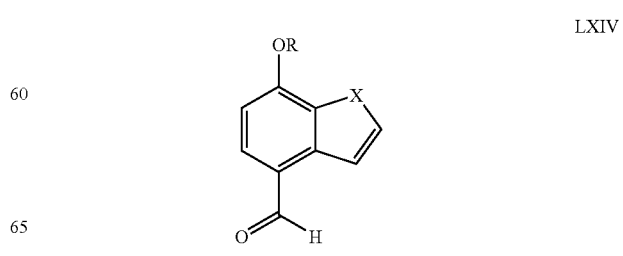

Scheme 13

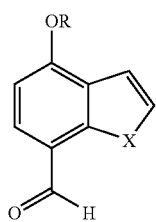

LXV

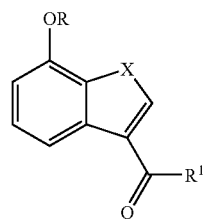

LXI

Aldehydes of formula (LXIV and LXV, where X=N, O or S and R=Alkyl or H) are known. Compounds of formula (LXI, R=Me, X=N and $R^1$=H) are known and compounds of formula (LXI, R=Me, X=O or S and $R^1$=H) can be obtained via reduction and subsequent oxidation of known compounds of formula (LXI, R=Me, X=O or S and $R^1$=OMe) using well known reagents.

Compounds of the formula (LXX) can be also prepared using the method illustrated in Scheme 14:

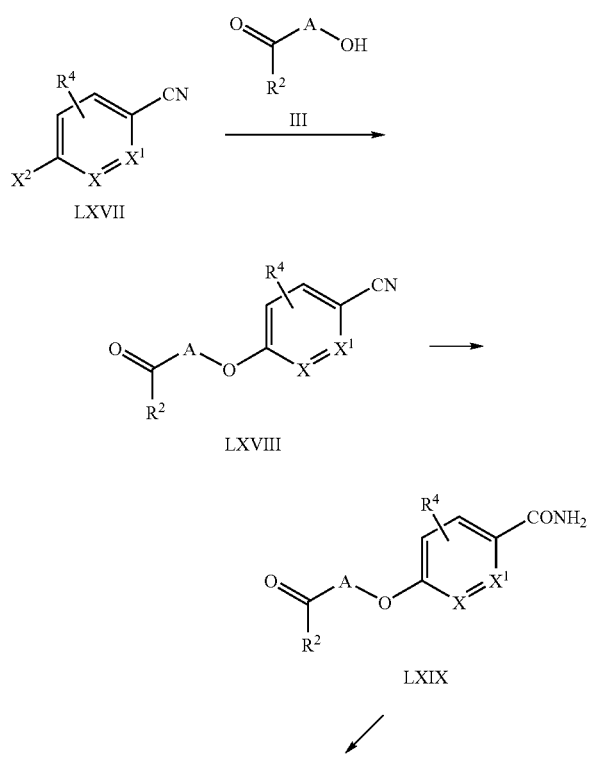

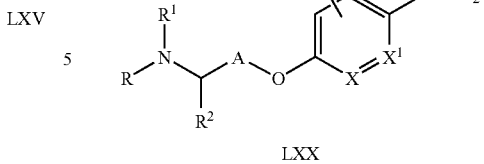

LXX

Halo nitriles of the formula (LXVII, X=N, CH or C, $X^1$=CH or C, and $X^2$=F, Cl) are readily available and can be reacted with hydroxy carbonyls of formula (III) using a base such as potassium carbonate in a solvent such as DMF to give aldehydes/ketones of formula (LXVIII). Nitrile aldehydes/ketones of formula (LXVIII) can be hydrolysed with for example hydrogen peroxide and potassium carbonate in a solvent such as DMSO to give amides of formula (LXIX). Reductive amination of amides of formula (LXIX) with an amine as previous described gives compounds of formula (LXX). The hydrolysis and reductive amination reactions can also be carried out in the reverse order.

Further details for the preparation of the compounds of formula (I) are found in the examples.

The compounds of formula (I) may be prepared singly or as compound libraries comprising at least 2, for example 5 to 1,000, compounds and more preferably 10 to 100 compounds of formula (I). Compound libraries may be prepared by a combinatorial "split and mix" approach or by multiple parallel synthesis using either solution or solid phase chemistry, using procedures known to those skilled in the art.

During the synthesis of the compounds of formula (I), labile functional groups in the intermediate compounds, e.g. hydroxy, carboxy and amino groups, may be protected. The protecting groups may be removed at any stage in the synthesis of the compounds of formula (I) or may be present on the final compound of formula (I). A comprehensive discussion of the ways in which various labile functional groups may be protected and methods for cleaving the resulting protected derivatives is given in, for example, Protective Groups in Organic Chemistry, T. W. Greene and P. G. M. Wuts, (1991) Wiley-Interscience, New York, $2^{nd}$ edition.

Any novel intermediates as defined above, such as the compounds of formula (II) are also included within the scope of the invention.

The preferences recited above for the compounds of formula (I) also apply to any intermediate compounds.

As indicated above the compounds of formula (I) are useful as opioid receptor modulators e.g. for the treatment of obesity. For such use the compounds of formula (I) will generally be administered in the form of a pharmaceutical composition.

The invention also encompasses a pharmaceutical composition comprising a compound of formula (I), or a pharmaceutically acceptable salt thereof, in combination with a pharmaceutically acceptable carrier.

Preferably the composition is comprised of a pharmaceutically acceptable carrier and a non-toxic therapeutically effective amount of a compound of formula (I), or a pharmaceutically acceptable salt thereof.

Moreover, the invention also provides a pharmaceutical composition for the treatment of disease by modulating opioid receptors, e.g. resulting in the treatment of obesity, comprising a pharmaceutically acceptable carrier and a non-toxic therapeutically effective amount of compound of formula (I), or a pharmaceutically acceptable salt thereof.

The pharmaceutical compositions may optionally comprise other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds of formula (I), or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous).

Thus, the pharmaceutical compositions can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound of formula (I), or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The compounds of formula (I), or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, using a compound of formula (I), or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient.

Compositions containing a compound of formula (I), or pharmaceutically acceptable salts thereof, may also be prepared in powder or liquid concentrate form.

Generally, dosage levels on the order of 0.01 mg/kg to about 150 mg/kg of body weight per day are useful in the treatment of the above-indicated conditions, or alternatively about 0.5 mg to about 7 g per patient per day. For example, obesity may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of formula (I), may be used in the treatment of diseases or conditions in which opioid receptors play a role.

Thus the invention also provides a method for the treatment of a disease or condition in which opioid receptors play a role comprising a step of administering to a subject in need thereof an effective amount of a compound of formula (I), or a pharmaceutically acceptable salt thereof.

Diseases or conditions in which opioid receptors play a role include obesity. In the context of the present application the treatment of obesity is intended to encompass the treatment of diseases or conditions such as obesity and other eating disorders associated with excessive food intake e.g. by reduction of appetite and body weight, maintenance of weight reduction and prevention of rebound.

The compounds of the invention may also be used for treating of other diseases related to obesity including metabolic diseases such as Type II diabetes, metabolic syndrome (syndrome X), impaired glucose tolerance, dyslipidemia, hyperlipidemia, hypertriglyceridemia, hypercholesterolemia, low HDL levels and hypertension.

Other diseases or conditions in which opioid receptors play a role include substance abuse, alcohol abuse, compulsive gambling, depression, opiate overdose, septic shock, irritable bowel syndrome, nausea, vomiting and stroke.

The invention also provides a method for the regulation of feeding and/or satiety comprising a step of administering to a subject in need thereof an effective amount of a compound of formula (I), or a pharmaceutically acceptable salt thereof.

The invention also provides a method for the treatment of obesity comprising a step of administering to a subject in need thereof an effective amount of a compound of formula (I), or a pharmaceutically acceptable salt thereof.

The invention also provides a method for the treatment of a metabolic disease selected from Type II diabetes, metabolic syndrome (syndrome X), impaired glucose tolerance, dyslipidemia, hyperlipidemia, hypertriglyceridemia, hypercholesterolemia, low HDL levels and hypertension, comprising a step of administering to a subject in need thereof an effective amount of a compound of formula (I), or a pharmaceutically acceptable salt thereof.

The invention also provides the use of a compound of formula (I), or a pharmaceutically acceptable salt thereof, in the treatment of a condition as defined above.

The invention also provides the use of a compound of formula (I), or a pharmaceutically acceptable salt thereof, in the manufacture of a medicament for the treatment of a condition as defined above.

In the methods of the invention the term "treatment" includes both therapeutic and prophylactic treatment.

The compounds of formula (I), or pharmaceutically acceptable salts thereof, may be administered alone or in combination with one or more other therapeutically active compounds. The other therapeutically active compounds may be for the treatment of the same disease or condition as the compounds of formula (I), or a different disease or condition. The therapeutically active compounds may be administered simultaneously, sequentially or separately.

The compounds of formula (I), may be administered with other active compounds for the treatment of obesity and/or diabetes, for example insulin and insulin analogs, gastric lipase inhibitors, pancreatic lipase inhibitors, sulfonyl ureas and analogs, biguanides, $\alpha 2$ agonists, glitazones, PPAR-$\gamma$ agonists, RXR agonists, fatty acid oxidation inhibitors, $\alpha$-glucosidase inhibitors, $\beta$-agonists, phosphodiesterase inhibitors, lipid lowering agents, glycogen phosphorylase inhibitors, MCH-1 antagonists, CB-1 antagonists, GPR119 agonists, serotonin and noradrenalin reuptake inhibitors, amylin antagonists, lipoxygenase inhibitors, somostatin analogs, glucokinase activators, glucagon antagonists, insulin signalling agonists, PTP1B inhibitors, gluconeogenesis inhibitors, antilypolitic agents, GSK inhibitors, galanin receptor agonists, anorectic agents, CCK receptor agonists, leptin, serotonergic/dopaminergic antiobesity drugs, CRF antagonists, CRF binding proteins, thyromimetic compounds, aldose reductase inhibitors, glucocorticoid receptor antagonists, NHE-1 inhibitors or sorbitol dehydrogenase inhibitors.

All publications, including, but not limited to, patents and patent application cited in this specification, are herein incorporated by reference as if each individual publication were specifically and individually indicated to be incorporated by reference herein as fully set forth.

The invention will now be described by reference to the following examples which are for illustrative purposes and are not to be construed as a limitation of the scope of the present invention.

EXAMPLES

Materials and Methods

Column chromatography was carried out on $SiO_2$ (40-63 mesh). LCMS data were obtained using a Waters Symmetry 3.5μ $C_{18}$ column (2.1×30.0 mm, flow rate=0.8 mL/min) eluting with a (5% MeCN in $H_2O$)-MeCN solution containing 0.1% $HCO_2H$ over 6 min and UV detection at 220 nm Gradient information: 0.0-1.2 min: 100% (5% MeCN in $H_2O$); 1.2-3.8 min: Ramp up to 10% (5% MeCN in $H_2O$)-90% MeCN; 3.8-4.4 min: Hold at 10% (5% MeCN in $H_2O$)-90% MeCN; 4.4-5.5 min: Ramp up to 100% MeCN; 5.5-6.0 min: Return to 100% (5% MeCN in $H_2O$). The mass spectra were obtained employing an electrospray ionisation source in either the positive ($ES^+$) or negative ($EST$) ion mode. Where chlorine is present in the molecule the masses are quoted for $^{35}Cl$ and when bromine is present $^{81}Br$ has been quoted. Additional LCMS data (LCMS method 2) were obtained using Waters Xterra MS C18, 5 μm (4.6×50 mm, flow rate 1.5 mL/min) eluting with a $H_2O$-MeCN gradient containing 0.1% v/v ammonia over 12 min with UV detection at 215 and 254 nm Gradient information: 0.0-8.0 min: Ramp from 95% $H_2O$-5% MeCN to 5% $H_2O$-95% MeCN; 8.0-9.9 min: Hold at 5% $H_2O$-95% MeCN; 9.9-10.0 min: Return to 95% $H_2O$-5% MeCN; 10.0-12.0 min: Hold at 95% $H_2O$-5% MeCN. Mass spectra were obtained using an electrospray ionization source in either the positive (ESI) or negative (EST) mode. Prep HPLC purification was carried out using a Lunar 10μ

ODS2 (250×21.2 mm; Flow rate=20 mL/min) eluting with solvent A (10% MeCN, 90% water) and solvent B (90% MeCN, 10% water) and UV detection at 215 nm Gradient information: 0.0-0.2 min: 90% A, 10% B; 0.2-10.0 min: Ramp up to 10% A, 90% B; 10.0-15.0 min: 10% A, 90% B; 15.0-16.0 min: Return to 90% A, 10% B.

Abbreviations and Acronyms:

MeCN: Acetonitrile; $NH_3$: Ammonia; $NH_4OH$ Ammonium hydroxide; $BBr_3$: Boron tribromide; bs: broad singlet; conc: concentrated; d: doublet; dd: doublet of doublet; DCM: Dichloromethane; DIBAL-H: diisobutylaluminium hydride; DIPEA: N,N-Diisopropylethylamine; DME: Dimethoxyethane; DMSO: Dimethylsulfoxide; DMF: N,N-Dimethylformamide; Ether: Diethyl ether; EtOH: Ethanol; EtOAc: Ethyl acetate; h: hour(s); HCl: Hydrogen chloride; $H_2O_2$: Hydrogen peroxide; $LiAlH_4$: Lithium aluminium hydride; $MgSO_4$: Magnesium sulphate; MeOH: Methanol; m: multiplet; $K_2CO_3$: Potassium Carbonate; q: quartet; rt: room temperature; RT: Retention time; sat.: saturated; s: singlet; $NaBH_4$: Sodium borohydride; $Na_2CO_3$: Sodium carbonate; $NaHCO_3$: Sodium hydrogen carbonate; NaOH: Sodium hydroxide; $Na_2S_2O_3$: sodium thiosulfate; $NaBH(OAc)_3$: Sodium triacetoxyborohydride; THF: Tetrahydrofuran; TFA: Trifluoroacetic acid; t: triplet; $Et_3N$: Triethylamine Preparation 1:
6-(4-Formylnaphthalen-1-yloxy)nicotinonitrile

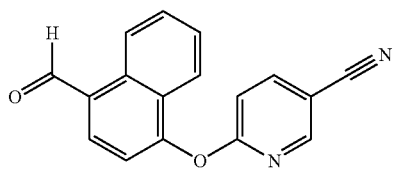

To a solution of 4-hydroxynaphthaldehyde (1.24 g, 7.2 mmol) in DMSO (8 mL) was added 2-chloro-5-cyanopyridine (1.0 g, 7.2 mmol) and $K_2CO_3$ (2.0 g, 14.5 mmol). The reaction was heated at 80° C. for 4 h. The reaction was cooled to rt and poured into water (100 mL). The resulting solid was filtered, washed with water, ether and air dried to give the title compound: RT=3.54 min; m/z (ES$^+$)=275.0 [M+H]$^+$.

Preparation 2:
6-(4-Formylnaphthalen-1-yloxy)nicotinamide

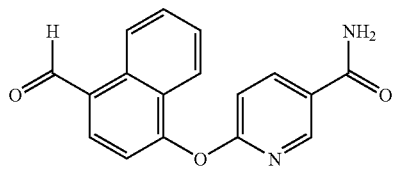

To a solution of 6-(4-formylnaphthalen-1-yloxy)nicotinonitrile (Preparation 1) (3.83 g, 14.0 mmol) in DMSO (90 mL) was added $K_2CO_3$ (0.97 g, 7.0 mmol). The mixture was cooled to 0° C., $H_2O_2$ (27.5% w/v, 4.6 mL, 37.0 mmol) added dropwise and the reaction allowed to warm to rt. The mixture was poured into water (300 mL) and the resulting precipitate was filtered, washed with water and air dried to give the title compound which was used without further purification: RT=3.13 min; m/z (ES$^+$)=292.9 [M+H]$^+$.

Preparation 3: Benzyl-(4-isopropylcyclohexyl)amine

Using the procedure outlined in Example 1, 4-isopropylcyclohexanone and benzylamine were converted to the title compound: RT=2.52 min; m/z (ES$^+$)=232.1 [M+H]$^+$.

The procedure described in Example 1 was used for Preparations 4-6 in Table 1 from benzylamine and the appropriate ketone:

TABLE 1

| Prep | Structure | Name | RT (min) | m/z (ES$^+$) |
|---|---|---|---|---|
| 4 | 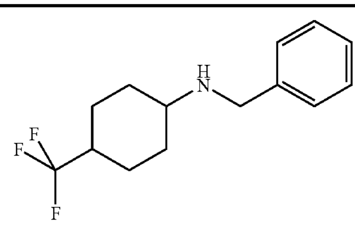 | Benzyl-(4-trifluoromethylcyclohexyl)amine | 2.32 | 258.1 [M + H]$^+$ |
| 5 | 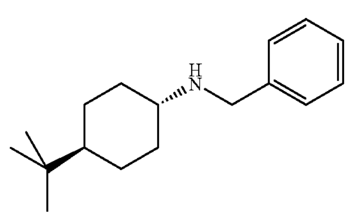 | trans-Benzyl-(4-tert-butylcyclohexyl)amine | 2.77 | 246.2 [M + H]$^+$ |

TABLE 1-continued

| Prep | Structure | Name | RT (min) | m/z (ES+) |
|---|---|---|---|---|
| 6 | 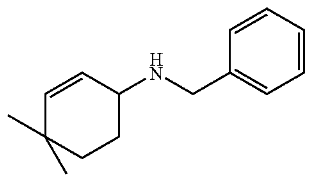 | Benzyl-(4,4-dimethylcyclohex-2-enyl)amine | 2.39 | 216.1 [M + H]+ |

Preparation 7: 4-Isopropylcyclohexylamine hydrochloride salt

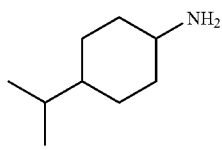

To a solution of benzyl-(4-isopropylcyclohexyl)amine (Preparation 3) (2.39 g, 10.7 mmol) in THF (10 mL) under argon was added 10% palladium-on-carbon (1.14 g, 1.1 mmol). The reaction was then stirred under an atmosphere of $H_2$ for 16 h. The mixture was filtered through Celite and washed with THF (50 mL) and the solvent was removed in vacuo. The residue was dissolved in EtOAc (10 mL) and 1M HCl in ether (5.3 mL) added. The precipitate was filtered off to give to title compound: RT=2.25 min; m/z (ES+)=142.1 [M+H]+.

The procedure described in Preparation 7 was used for Preparations 8-9 in Table 2 from the appropriate benzylamines:

TABLE 2

| Prep | Structure | Name | NMR |
|---|---|---|---|
| 8 | 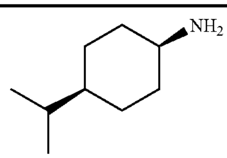 | cis-4-Isopropylcyclohexylamine hydrochloride | $\delta_H$ (CD$_3$OD) 0.91-0.96 (6H, m), 1.13-1.23 (1H, m), 1.45-1.67 (5H, m), 1.72-1.80 (4H, m), 3.31-3.38 (1H, m) |
| 9 | 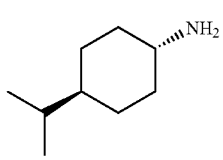 | trans-4-Isopropylcyclohexylamine hydrochloride | $\delta_H$ (DMSO) 0.79-0.86 (6H, m), 0.94-1.07 (3H, m), 1.21-1.34 (2H, m), 1.35-1.46 (1H, m), 1.66-1.75 (2H, m), 1.91-2.00 (2H, m), 2.82-2.92 (1H, m), 7.90-8.11 (2H, bs) |

Preparation 10: 4,4-Dimethylcyclohexylamine hydrochloride

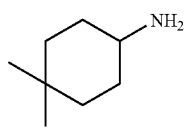

Using the procedure outlined in Preparation 7, benzyl-(4,4-dimethylcyclohex-2-enyl)amine (Preparation 6) was converted to the title compound: RT=1.75 min; m/z (ES+)=128.1 [M+H]+.

Preparation 11: 5-Methoxynaphthalene-1-carbonitrile

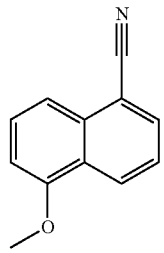

To a solution of 1-iodo-5-methoxynapthalene (J. A. O'Meara et al., *J. Med. Chem.*, 2005, 48, 5580-5588 1.104 g, 3.89 mmol) in dimethylacetamide (6 mL) at rt under nitrogen, was added potassium ferrocyanide (494 mg, 1.17 mmol), Na$_2$CO$_3$ (412 mg, 3.89 mmol) and palladium acetate (43 mg, 0.19 mmol). The reaction mixture was stirred at 120° C. for 3 h, cooled, diluted with EtOAc (100 mL) and filtered through Celite. The organic phase was washed with water (30 mL), NaHCO$_3$ (30 mL), brine (30 mL) and dried (MgSO$_4$). Solvent was removed in vacuo and the residue purified by column chromatography (isohexane:EtOAc, 90:10 to 85:15) to give the title compound: RT=3.64 min; m/z (ES+)=184.0 [M+H]+.

Preparation 12: 5-Methoxynaphthalen-1-ylmethylamine

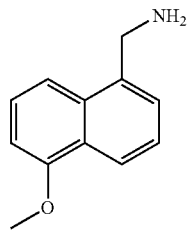

To a solution of LiAlH$_4$ (244 mg, 6.44 mmol) in THF (30 mL) at rt under nitrogen was added 5-methoxynaphthalene-1-carbonitrile (Preparation 11) (513 mg, 2.80 mmol). The reaction mixture was heated to 90° C. for 3 h, then cooled to rt. Water (0.25 mL) was added followed by 1M NaOH (0.25 mL) and water (0.5 mL). The mixture was filtered through Celite and the solvent removed in vacuo to give the title compound: RT=1.99 min; m/z (ES$^+$)=188.0 [M+H]$^+$.

Preparation 13: (5-Methoxynaphthalen-1-ylmethyl)-(3-methylbutyl)amine

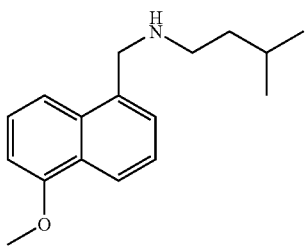

To a solution of 5-methoxynaphthalen-1-ylmethylamine (Preparation 12) (389 mg, 2.08 mmol) in MeOH (15 mL), was added 3-methylbutyraldehyde (223 μL, 2.08 mmol). The mixture was stirred for 16 h at rt under nitrogen before adding NaBH$_4$ (236 mg, 6.24 mmol). After stirring for 1 h water (0.5 mL) was added and the solvent removed in vacuo. The mixture was partitioned between EtOAc (100 mL) and NaHCO$_3$ (25 mL), the organic phase was washed with water (25 mL), brine (25 mL) and dried (MgSO$_4$). Solvent was removed in vacuo and the residue purified by column chromatography (DCM: MeOH: NH$_4$OH, 97:3:0.3 to 95:5:0.5) to give the title compound: RT=2.46 min; m/z (ES$^+$)=258.1 [M+H]$^+$.

Preparation 14: 5-[(3-Methylbutylamino)methyl]naphthalen-1-ol

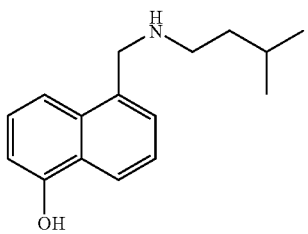

To a solution of 5-methoxynaphthalen-1-ylmethyl(3-methylbutyl)amine (Preparation 13) (310 mg, 1.20 mmol) in DCM (15 mL) at −78° C., was added 1M BBr$_3$ in DCM (3.61 mL, 3.61 mmol.). The reaction mixture was stirred at −78° C. for 16 h. NaHCO$_3$ (0.5 mL) was added and the mixture partitioned between NaHCO$_3$ (0.25 mmol) and EtOAc (50 mL). The aqueous phase was extracted with EtOAc (2×50 mL) and the combine organic phases washed with 1M NaOH (20 mL). The aqueous phase was acidified with 1M HCl to pH 7 and extracted with EtOAc (100 mL). The organic phase was washed with brine (25 mL) and dried (MgSO$_4$). Solvent was removed in vacuo to give the title compound: RT=2.49 min; m/z (ES$^+$)=244.1 [M+H]$^+$.

Preparation 15: 6-{5-[(3-Methylbutylamino)methyl]naphthalen-1-yloxy}nicotinonitrile

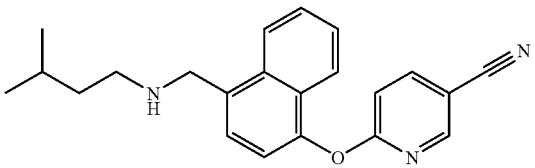

To a solution of 5-[(3-methylbutylamino)methyl]naphthalen-1-ol (Preparation 14) (85 mg, 0.35 mmol) in DMF (10 mL), was added 6-chloronicotinonitrile (43 mg, 0.62 mmol) and K$_2$CO$_3$ (86 mg, 0.62 mmol). The reaction mixture was heated at 70° C. for 16 h. Solvent was removed in vacuo and residue partitioned between EtOAc (50 mL) and water (20 mL). The aqueous phase was extracted with EtOAc (50 mL) and the organic phase washed with NaHCO$_3$ (20 mL), brine (20 mL) and dried (MgSO$_4$). Solvent was removed in vacuo and the residue purified by column chromatography (DCM: MeOH:NH$_4$OH, 95:5:0.5) to give the title compound: RT=2.83 min; m/z (ES$^+$)=346.0 [M+H]$^+$.

Preparation 16: 4-(4-Formylisoquinolin-1-yloxy)benzamide

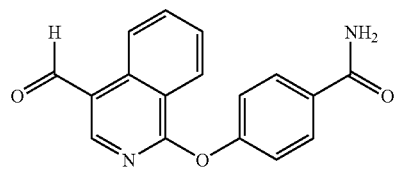

To a solution of 4-hydroxybenzamide (0.96 g, 7.0 mmol) in DMF (15 mL) at rt was added sodium hydride (0.28 g, 7.0 mmol). After 1 h, 1-chloro-isoquinoline-4-carbaldehyde (WO01/53274, 1.34 g, 7.0 mmol) was added and the reaction heated at 120° C. for 16 h. The solvent was removed in vacuo and the residue washed with water (100 mL), ether (50 mL) and MeCN (50 mL) to give the title compound: RT=3.13 min; m/z (ES$^+$)=292.9 [M+H]$^+$.

Preparation 17: 6-(1-Chloroisoquinolin-4-yloxy)nicotinonitrile

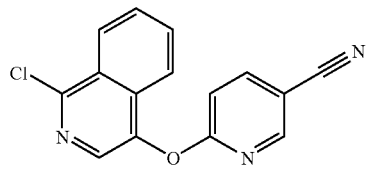

To a solution of 1-chloro-4-hydroxyisoquinoline (1.0 g, 5.6 mmol) in DMF (16 mL), was added 6-chloronicotinonitrile (0.55 g, 4.0 mmol) and $K_2CO_3$ (1.65 g, 11.9 mmol). The reaction mixture was heated at 70° C. for 6.5 h. Solvent was removed in vacuo and residue partitioned between EtOAc (100 mL), THF (100 mL) and water (60 mL). The organic phase was washed with water (2×60 mL), 1M NaOH (2×40 mL), brine (40 mL) and dried ($MgSO_4$). Solvent was removed in vacuo to give the title compound: RT=3.66 min; m/z (ES$^+$)=282.0 [M+H]$^+$.

Preparation 18:
6-(1-Methylisoquinolin-4-yloxy)nicotinonitrile

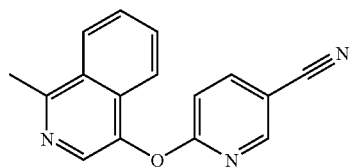

To a solution of 6-(1-chloroisoquinolin-4-yloxy)nicotinonitrile (Preparation 17) (300 mg, 1.1 mmol) in DMF (8 mL) under argon was added trimethylboroxine (148 μL, 1.1 mmol) followed by $K_2CO_3$ (442 mg, 3.2 mmol) and palladium tetrakistriphenylphosphine (123 mg, 0.1 mmol). The mixture was purged with argon for 5 min and then heated to 80° C. for 16 h. Solvent was removed in vacuo. The residue was partitioned between EtOAc (100 mL) and water (40 mL), the organic phase was washed with water (40 mL), $NaHCO_3$ (40 mL), brine (30 mL) and dried ($MgSO_4$). Solvent was removed in vacuo and the residue purified by column chromatography (2% MeOH: DCM) to give the title compound: RT=2.40 min; m/z (ES$^+$)=262.4 [M+H]$^+$.

Preparation 19:
6-(1-Methylisoquinolin-4-yloxy)nicotinamide

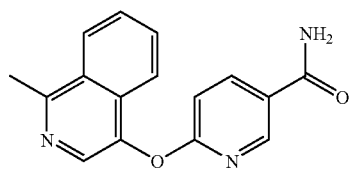

To a solution of 6-(1-methylisoquinolin-4-yloxy)nicotinonitrile (Preparation 18) (200 mg, 0.77 mmol) in DMSO (5 mL) was added $K_2CO_3$ (53 mg, 0.38 mmol) and $H_2O_2$ (30% w/v, 120 μL, 1.1 mmol). After 1 h water (20 mL) was added and the mixture extracted with EtOAc (3×50 mL). The organic phase was washed with water (2×30 mL), $NaHCO_3$ (30 mL), brine (30 mL) and dried ($MgSO_4$). Solvent was removed in vacuo and the residue purified by column chromatography (0.5 $NH_3$: 5 MeOH: 95 DCM) to give the title compound: RT=2.11 min; m/z (ES$^+$)=280.1 [M+H]$^+$.

Preparation 20:
6-(1-Formylisoquinolin-4-yloxy)nicotinamide

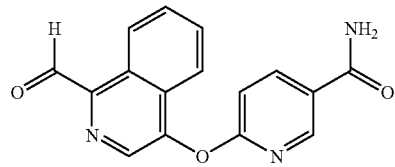

To 6-(1-methylisoquinolin-4-yloxy)nicotinamide (Preparation 19) (135 mg, 0.48 mmol) in dioxane (6 mL) under argon was added selenium dioxide (54 mg, 0.48 mmol). The mixture was heated to 80° C. for 3 h after which time selenium dioxide (54 mg, 0.48 mmol) was added. After a further 0.5 h at 80° C. the mixture was cooled, filtered through Celite and washed with EtOAc (50 mL). The organic phase was washed with $NaHCO_3$ (30 mL), water (30 mL), brine (30 mL) and dried ($MgSO_4$). Solvent was removed in vacuo to give the title compound: RT=2.93 min; m/z (ES$^+$)=294.1 [M+H]$^+$.

Preparation 21: 5-Methylnaphthalen-1-ol

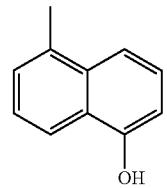

Using the procedure by D. G. Batt et al., (*J. Org. Chem.*, 1991, 56, 23, 6704-6708), 2-amino-3-methylbenzoic acid was converted to the title compound: RT=2.93 min; m/z (ES$^+$)=159.1 [M+H]$^+$.

Preparation 22:
6-(5-Methylnaphthalen-1-yloxy)nicotinonitrile

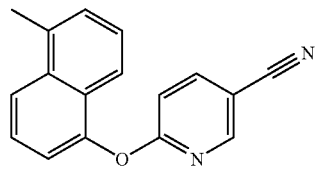

Using the procedure outlined in Preparation 15, 5-methylnaphthalen-1-ol and 6-chloronicotinonitrile were converted to the title compound: RT=3.90 min; m/z (ES$^+$)=261.1 [M+H]$^+$.

Preparation 23:
6-(5-Bromomethylnaphthalen-1-yloxy)nicotinonitrile

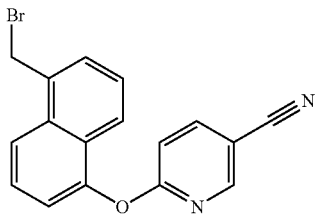

To a solution of 6-(5-methylnaphthalen-1-yloxy)nicotinonitrile (Preparation 22) (530 mg, 2.04 mmol) in carbon tetrachloride (30 mL) under argon was added N-bromosuccinimide (435 mg, 2.44 mmol) followed by benzoyl peroxide (25 mg, 0.1 mmol). The mixture was heated to 70° C. for 16 h. The reaction mixture was cooled, filtered through celite, and washed with DCM (70 mL). The organic phase was washed with NaHCO$_3$ (30 mL), brine (30 mL) and dried (MgSO$_4$). Solvent was removed in vacuo to give the title compound: RT=3.93 min; m/z (ES$^+$)=341.0 [M+H]$^+$.

Preparation 24: 5-Hydroxynaphthalene-1-carboxylic acid

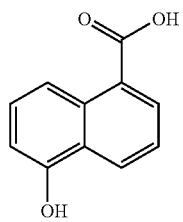

The title compound was synthesised in 4 unambiguous steps starting from naphthalene-1-carboxylic acid via regioselective bromination, esterification, copper(I)-promoted halogen/methoxide exchange[a] and final double demethylation[b]: δ$_H$ (DMSO): 6.95 (1H, d), 7.43 (1H, dd), 7.52 (1H, dd), 8.11 (1H, d), 8.27 (1H, d), 8.41 (1H, d), 10.31 (1H, bs), 13.02 (1H, bs).

a) M. Lukeman et al., *Canadian Journal of Chemistry*, 2004, 82, 240-253
b) J. A. O'Meara et al., *Journal of Medicinal Chemistry*, 2005, 48, 5580-5588

Preparation 25:
5-Hydroxynaphthalene-1-carbonitrile

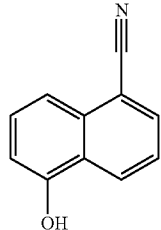

To a solution of 5-methoxynaphthalene-1-carbonitrile (Preparation 11) (880 mg, 4.80 mmol) in DCM (10 mL) under argon at 0° C. was added 1M BBr$_3$ solution in DCM (12.5 mL). After 10 min the mixture was maintained at rt for 4 h. The mixture was partitioned between NaHCO$_3$ solution and EtOAc, the organic phase was washed with 1M HCl, brine and dried (MgSO$_4$). Solvent was removed in vacuo and the residue purified by column chromatography (isohexane:EtOAc, 2:1) to give the title compound: δ$_H$(CD$_3$OD): 6.97 (1H, d), 7.50, 7.52 (2H, 2dd), 7.62 (1H, d), 7.94 (1H, d), 8.53 (1H, d).

Preparation 26:
5-Hydroxynaphthalene-1-carbaldehyde

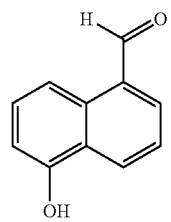

To a suspension of 5-hydroxynaphthalene-1-carbonitrile (Preparation 25) (580 mg, 3.43 mmol) in DCM (25 mL) under argon at −78° C. was added DIBAL-H (8 mL, 1M, in toluene). The mixture was stirred for 1 h at −78° C., 0.5 h at rt, recooled to −78° C. and quenched with NH$_4$Cl solution. EtOAc was added, organic phase was washed with sat. potassium sodium tartrate solution, water, brine and then dried (MgSO$_4$). Solvent was removed in vacuo and the residue purified by column chromatography (isohexane:EtOAc, 1:1) gave the title compound: δ$_H$ (CD$_3$OD): 6.97 (1H, d), 7.51 (1H, dd), 7.63 (1H, dd), 8.08 (1H, d), 8.61 (1H, d), 8.69 (1H, d), 10.38 (1H, s).

Preparation 27:
5-Methoxynaphthalene-1-carbaldehyde

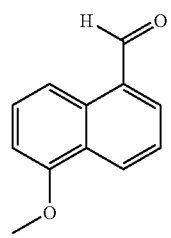

To a solution of 5-methoxynaphthalene-1-carbonitrile (Preparation 11) (1.1 g, 6.00 mmol) in DCM (40 mL) at −78° C. under nitrogen was added DIBAL (1.0M in toluene, 18 mL) dropwise over 10 minutes. The reaction mixture was stirred at −78° C. for 1 h, warmed to rt for 1 h and then cooled to 0° C. Acetic acid (1 mL) followed by water (1 mL) were added. The mixture was partitioned between EtOAc (100 mL) and water (100 mL), the organic phase was separated and dried (MgSO$_4$). Solvent was removed in vacuo and the residue purified by column chromatography (EtOAc:isohexane 2:8) to give the title compound: RT=3.54 min; m/z (ES$^+$)=187.0 [M+H]$^+$.

Preparation 28: 4-(4-Formylnaphthalen-1-yloxy)benzonitrile

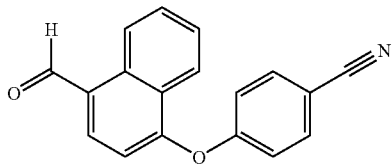

To a solution of 4-hydroxy-1-napthaldehyde (172 mg, 1.0 mmol) in DCM (10 mL) was added copper (II) diacetate (181 mg, 1.0 mmol), 4-cyanophenyl boronic acid (441 mg, 3.0 mmol), triethylamine (0.7 mL, 5.0 mmol) and 4 Å molecular sieves. After 48 h at rt the mixture was filtered. Solvent was removed in vacuo and the residue purified by column chromatography (EtOAc:isohexane 3:7). The resulting solid was washed with ether (10 mL) and filtered. The filtrate was concentrated in vacuo to give the title compound: $\delta_H$ (CDCl$_3$) 7.06 (1H, d), 7.21 (2H, d), 7.49 (1H, t), 7.62-7.82 (3H, m), 7.96 (1H, d), 8.28 (1H, d), 9.36 (1H, d), 10.33 (1H, s).

Preparation 29: (5-Methoxynaphthalen-1-ylmethyl)-bis-(3-methylbutyl)amine

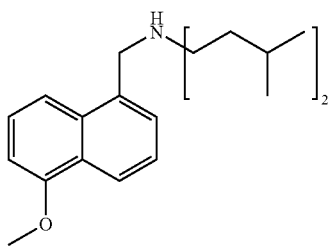

To a solution of 5-methoxynaphthalen-1-yl-methylamine (Preparation 12) (1.83 g, 9.80 mmol) in DCM (100 mL) was added 3-methylbutyraldehyde (1.26 mL, 11.8 mmol), acetic acid (0.6 mL, 10.5 mmol) and NaBH(OAc)$_3$ (3.2 g, 15.1 mmol). The mixture was stirred for 48 h at rt. Following the addition of EtOAc (200 mL) and NaHCO$_3$ solution (200 mL the mixture was stirred for 1 h. The organic phase was separated, washed with brine and dried (MgSO$_4$). Solvent was removed in vacuo and the residue purified by column chromatography (hexane:EtOAc, 5:1) to give the title compound: RT=2.65 min; m/z (ES$^+$)=314.5 [M+H]$^+$.

Preparation 30: 3-Nitrophthalic acid 1-methyl ester

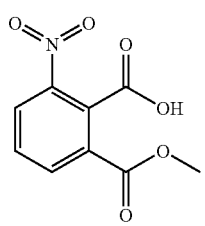

To MeOH (100 ml) at 0° C. was added acetyl chloride (14.5 mL, 203.4 mmol) and the solution stirred at rt for 1 h. 3-Nitrophthalic acid (25.7 g, 121.7 mmol) was added and the mixture heated at reflux for 22 h. The reaction was cooled to rt and partitioned between water (80 mL) and EtOAc (3×80 mL). The combined organic phase was dried (MgSO$_4$) and solvent removed in vacuo to give the title compound: Data in agreement with previous reports (Roger, M. E.; Averill, B. A. *J. Org. Chem.* 1986, 51, 3308-3314).

Preparation 31: 3-Aminophthalic acid 1-methyl ester

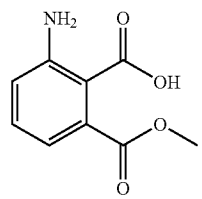

Prepared from 3-nitrophthalic acid 1-methyl ester (Preparation 30) according to previous reports: Data in agreement with previous reports (Roger, M. E.; Averill, B. A. *J. Org. Chem.* 1986, 51, 3308-3314).

Preparation 32: 5-Hydroxymethylnaphthalen-1-ol

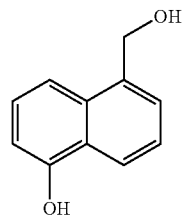

Method A: Prepared from 3-aminophthalic acid 1-methyl ester (Preparation 31) according to previous reports: Data in agreement with previous reports (WO 2005/123069 PCT/US2005/020519).

Method B: A solution of 5-hydroxynaphthalene-1-carboxylic acid (Preparation 24) (1.75 g, 9.30 mmol) in THF (50 mL) was added slowly to a suspension of LiAlH$_4$ (1.08 g, 28.5 mmol) in THF (150 mL). The reaction mixture was refluxed for 12 h. The mixture was added to ice water (500 mL) and acidified with 1M HCl (100 mL). The mixture was extracted with EtOAc and the organic phase washed with brine and dried (MgSO$_4$). Solvent was removed in vacuo to give the title compound: $\delta_H$ (DMSO): 4.94 (2H, d), 5.25 (1H, t), 6.90 (1H, d), 7.34 (1H, dd), 7.41 (1H, dd), 7.49 (1H, d), 7.55 (1H, d), 8.10 (1H, d), 10.06 (1H, s).

Preparation 33: 6-(5-Hydroxymethylnaphthalene-1-yloxy)nicotinonitrile

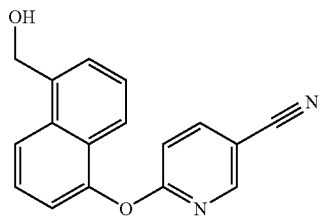

Using the procedure outlined in Preparation 15, 5-hydroxymethylnaphthalen-1-ol (Preparation 32) and 6-chloronicotinonitrile were converted to the title compound: RT=3.17 min; m/z (ES$^+$)=277.1 [M+H]$^+$.

Preparation 34: 6-(5-Formylnaphthalen-1-yloxy)nicotinonitrile

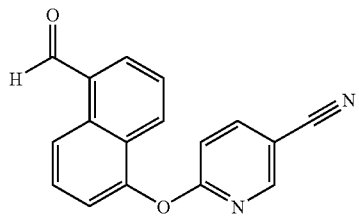

Method A: To a solution of 6-(5-hydroxymethylnaphthalene-1-yloxy)nicotinonitrile (Preparation 33) (1.0 g, 3.62 mmol) in DCM (25 mL) under argon was added Dess-Martin periodinane (1.84 g, 4.34 mmol). The mixture was stirred at rt for 3 h then diluted with EtOAc (100 mL). The organic phase was washed with sat. Na$_2$S$_2$O$_3$ (75 mL), NaHCO$_3$ (50 mL), brine (50 mL) and then dried (MgSO$_4$). Solvent was removed in vacuo to give the title compound: RT=3.60 min; m/z (ES$^+$)=275.1 [M+H]$^+$.

Method B: To a solution of 6-(5-bromomethylnaphthalen-1-yloxy)nicotinonitrile (Preparation 23) (300 mg, 0.88 mmol) in DMSO (3 mL) under argon was added NaHCO$_3$ (149 mg, 1.77 mmol) and the mixture was heated to 85° C. for 4 h. The mixture was partitioned between water (10 mL) and EtOAc (2×50 mL), the organic phase was washed with water (50 mL), NaHCO$_3$ (30 mL), brine (30 mL) and dried (MgSO$_4$). Solvent was removed in vacuo to give the title compound.

Preparation 35: 6-(5-Formylnaphthalen-1-yloxy)nicotinamide

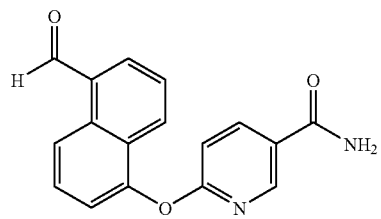

Method A: Using the procedure outlined in Preparation 19, 6-(5-formylnaphthalen-1-yloxy)nicotinonitrile was converted to the title compound: RT=3.04 min; m/z (ES$^+$)=293.1 [M+H]$^+$.

Method B: To a suspension of 6-(5-{[bis(3-methylbutyl)amino]methyl}naphthalen-1-yloxy)nicotinamide hydrochloride (Example 92) (1.05 g, 2.42 mmol) in 80% aqueous DMF (50 mL) was added N-bromosuccinimide (967 mg, 5.43 mmol). The mixture was stirred for 12 h at rt. EtOAc (500 mL) was added and the organic phase washed with water, 10% Na$_2$S$_2$O$_3$ solution, brine and then dried (MgSO$_4$). Solvent was removed in vacuo and the residue purified by column chromatography (EtOAc) to give the title compound.

Preparation 36: 3-Fluoro-4-(5-hydroxymethylnaphthalen-1-yloxy)benzonitrile

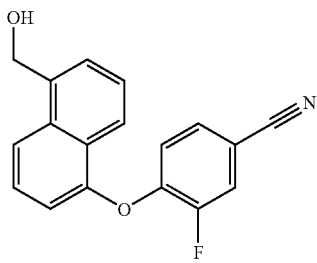

To a solution of 5-hydroxymethylnaphthalen-1-ol (Preparation 32) (350 mg, 2.01 mmol) and 3,4-difluorobenzonitrile (279 mg, 2.01 mmol) in sulfalone (8 mL) was added K$_2$CO$_3$ (1.39 g, 10.05 mmol) and the mixture heated to 80° C. for 16 h before cooling to rt. The mixture was partitioned between water (50 mL) and EtOAc (3×50 mL), the organic phase was washed with water (3×50 mL), brine (50 mL) and dried (MgSO$_4$). Solvent was removed in vacuo and the residue purified by column chromatography (SiO$_2$, MeOH:DCM, 2:98) to give the title compound: RT=3.54 min; m/z (ES$^+$)=276.1 [M H$_2$O]$^+$.

Preparation 37: 3-Fluoro-4-(5-formylnaphthalen-1-yloxy)benzonitrile

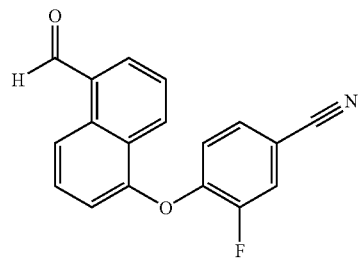

Using the procedure outlined in Preparation 34 method A, 3-fluoro-4-(5-hydroxymethylnaphthalen-1-yloxy)benzonitrile (Preparation 36) was converted to the title compound: δ$_H$ (DMSO): 7.12-7.17 (1H, m), 7.29-7.32 (1H, m), 7.65-7.69 (1H, m), 7.73-7.78 (1H, m), 7.82-7.87 (1H, m), 8.12-8.16 (1H, m), 8.29-8.32 (1H, m), 8.41-8.45 (1H, m), 9.02-9.06 (1H, m), 10.46 (1H, s).

Preparation 38:
3-Fluoro-4-(5-formylnaphthalen-1-yloxy)benzamide

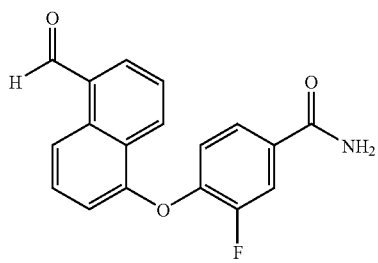

Using the procedure outlined in Preparation 19, 3-fluoro-4-(5-formylnaphthalen-1-yloxy)benzonitrile (Preparation 38) was converted to the title compound: RT=3.35 min; m/z (ES$^+$)=310.1 [M+H]$^+$.

Preparation 39: 4-(1-Chloroisoquinolin-4-yloxy)-3-fluorobenzonitrile

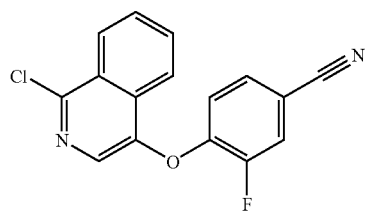

Using the procedure outlined in Preparation 17, 1-chloro-4-hydroxyisoquinoline and 3,4-difluorobenzonitrile were converted to the title compound: RT=3.90 min; m/z (ES$^+$)=299.04 [M+H]$^+$.

Preparation 40: 3-Fluoro-4-(1-methylisoquinolin-4-yloxy)benzonitrile

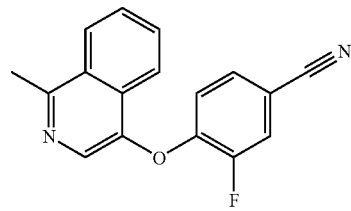

Using the procedure outlined in Preparation 18, 4-(1-chloroisoquinolin-4-yloxy)-3-fluorobenzonitrile (Preparation 39) was converted to the title compound: RT=2.85 min; m/z (ES$^+$)=279.1 [M+H]$^+$.

Preparation 41:
3-Fluoro-4-(1-methylisoquinolin-4-yloxy)benzamide

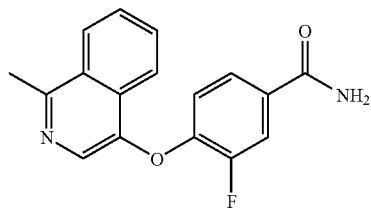

Using the procedure outlined in Preparation 19, 3-fluoro-4-(1-methylisoquinolin-4-yloxy)benzonitrile (Preparation 40) was converted to the title compound: RT=2.42 min; m/z (ES$^+$)=297.1 [M+H]$^+$.

Preparation 42:
3-Fluoro-4-(1-formylisoquinolin-4-yloxy)benzamide

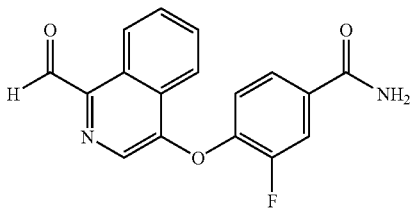

Using the procedure outlined in Preparation 20, 3-fluoro-4-(1-methylisoquinolin-4-yloxy)benzamide (Preparation 41) was converted to the title compound: RT=3.29 min; m/z (ES$^+$)=311.1 [M+H]$^+$.

Preparation 43: 6-{4-[(3-Methylbutylamino)methyl]naphthalen-1-yloxy}nicotinonitrile hydrochloride

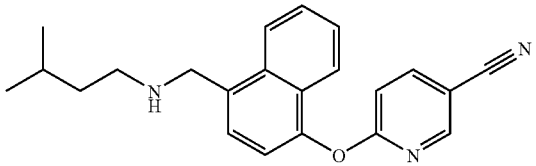

To a solution of 6-(4-formylnaphthalen-1-yloxy)nicotinonitrile (Preparation 1) (1.50 g, 5.47 mmol) in DCM (15 mL) was added acetic acid (0.98 mL, 16.42 mmol) and 3-methylbutylamine (1.91 mL, 16.42 mmol). After 1 h NaBH(OAc)$_3$ (3.48 g, 16.42 mmol) and DCM (20 mL) were added. The reaction was stirred at rt for a further 16 h. The mixture was partitioned between DCM (150 mL) and saturated NaHCO$_3$ (200 mL), the organic phase washed with water (200 mL) and dried (MgSO$_4$). Solvent removed in vacuo. To the residue was added ether (10 mL) followed by 4M HCl in dioxane (1.0 mL, 4.0 mmol). A further 40 mL of ether was added and the resulting precipitate filtered and dried under vacuum to give the title compound: RT=2.84 min; m/z (ES$^+$)=346.2 [M+H]$^+$.

Preparation 44: 4-Trifluoromethylcyclohexylamine hydrochloride

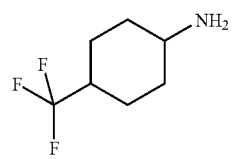

A solution of benzyl(4-trifluoromethylcyclohexyl)amine (Preparation 4) (1.48 g, 5.73 mmol) in MeOH (150 mL) was passed through an H-Cube at 100° C. fitted with a 10% Pd/C CatCart and on full H$_2$ mode. The volume was reduced to 50 mL and 4M HCl in dioxane (1.43 mL) was added. The precipitate was filtered, the filtrate collected and the solvent removed in vacuo. The resulting residue was triturated with acetone to give the title compound: $\delta_H$ (CD$_3$OD) 1.41-1.53 (4H, m), 2.03-2.25 (5H, m), 3.07-3.15 (1H, m).

Preparation 45: trans-4-tert-Butylcyclohexylamine hydrochloride

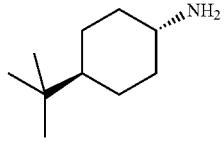

Using the procedure outlined in Preparation 44, trans-benzyl-(4-tert-butyl-cyclohexyl)amine (Preparation 5) was converted to the title compound: $\delta_H$ (DMSO) 0.81-1.08 (12H, m), 1.20-1.32 (2H, m), 1.72-1.80 (2H, m), 1.93-2.01 (2H, m), 2.83-2.92 (1H, m), 7.94 (2H, bs).

Preparation 46: cis-Benzyl(4-isopropylcyclohexyl)amine hydrochloride

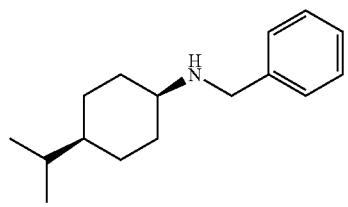

To a solution of 4-isopropylcyclohexanone (5.0 g, 36 mmol) and benzylamine (3.54 mL, 32 mmol) in MeOH (40 mL) was added 4 Å molecular sieves (2 g). After 16 h at rt NaBH$_4$ (2.45 g, 65 mmol) was added and the mixture stirred for a further 6 h. Water (3 mL) was added and the solvent was removed in vacuo. The residue was partitioned between NaHCO$_3$ (150 mL) and EtOAc (150 mL), the aqueous layer was extracted with EtOAc (2×50 mL) and the combined organic phases were washed with brine (2×50 mL) and dried (MgSO$_4$). Solvent was removed in vacuo and the residue purified by column chromatography (SiO$_2$, NH$_4$OH:MeOH:DCM 0.25:5:95) to give the product as a free base. 4M HCl in dioxane and Et$_2$O were added to the residue, and the resulting precipitate was filtered to give the title compound: $\delta_H$ (CD$_3$OD) 0.92-0.97 (6H, m), 1.17-1.26 (1H, m), 1.53-1.92 (9H, m), 3.21-3.29 (1H, m), 4.23 (2H, s) 7.44-7.54 (5H, m).

Preparation 47: trans-Benzyl(4-isopropylcyclohexyl)amine hydrochloride

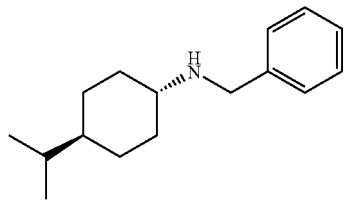

Using the procedure outlined in Preparation 46, benzylamine and 4-isopropylcyclo-hexanone were converted to the title compound: $\delta_H$ (CDCl$_3$) 0.83-0.90 (6H, m), 0.94-1.19 (4H, m), 1.23-1.48 (2H, m), 1.70-1.78 (2H, m), 1.96-2.04 (2H, m), 2.38-2.48 (1H, m), 3.83 (2H, s) 7.21-7.29 (1H, m), 7.30-7.36 (4H, m).

Preparation 48: 6-(5-{[Bis-(3-methylbutyl)amino]methyl}naphthalen-1-yloxy)-nicotinonitrile

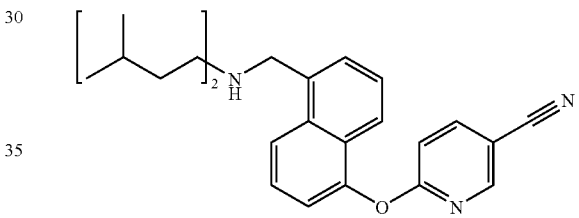

Using the procedure outlined in Preparation 14 and Preparation 15, (5-methoxynaphthalen-1-ylmethyl)-bis-(3-methylbutyl)amine (Preparation 29) and 2-chloro-5-cyanopyridine were converted to the title compound: RT=2.93 min; m/z (ES$^+$)=416.8 [M+H]$^+$.

Using the procedures outlined in Preparations 13, 14 and 15, the appropriate carbonyl compound, 5-methoxynaphthalen-1-yl-methylamine and 2-chloro-5-cyanopyridine were converted to Preparations 49-51 in Table 3.

TABLE 3

| Prep | Structure | Name | RT (min) | m/z (ES$^+$) |
|---|---|---|---|---|
| 49 | 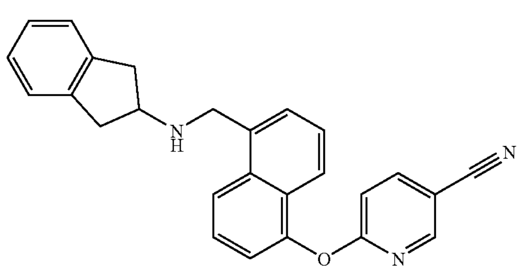 | 6-[5-(Indan-2-ylaminomethyl)-naphthalen-1-yloxy]-nicotinonitrile | 2.83 | 393.2 [M + H]$^+$ |

TABLE 3-continued

| Prep | Structure | Name | RT (min) | m/z (ES+) |
|---|---|---|---|---|
| 50 | 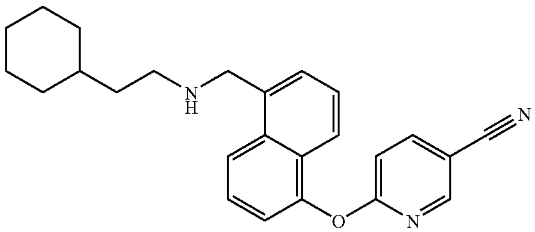 | 6-{5-[(2-Cyclohexyl-ethylamino)methyl]-naphthalen-1-yloxy}-nicotinonitrile | 3.12 | 386.2 [M + H]+ |
| 51 | 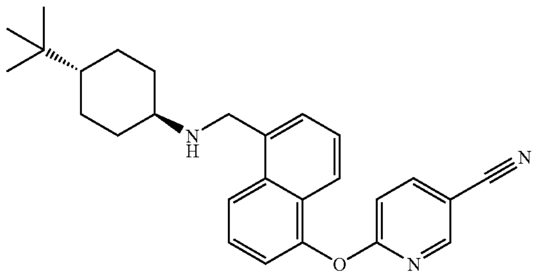 | Trans-6-{5-[(4-tert-Butylcyclohexyl-amino)methyl]-naphthalen-1-yloxy}-nicotinonitrile | 3.17 | 414.2 [M + H]+ |

Preparation 52:
cis-1-Benzylamino-4-propylcyclohexane and
Preparation 53:
trans-1-Benzylamino-4-propylcyclohexane

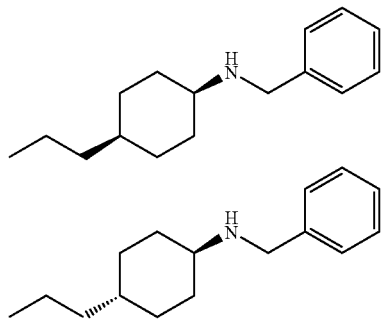

Using the procedure outlined in Example 1, benzylamine and 4-propylcyclohexanone gave a mixture of 2 stereoisomers. Purification by column chromatography on silica (toluene:acetone, 2:1) gave 2 compounds. The less polar product was identified as cis-1-benzylamino-4-propylcyclohexane: RT=2.29 min; m/z (ES+)=232.1 [M+H]+.

The more polar product was dissolved in MeOH (100 mL) and aqueous 1M HCl (10 mL) added. Solvent was removed in vacuo and the solid residue stirred in EtOAc (50 mL) for 4 h. The solid was filtered and air dried to give trans-1-benzylamino-4-propylcyclohexane hydrochloride: RT=2.63 min; m/z (ES+)=232.1 [M+H]+.

The procedure described in Preparation 53/54 was used to synthesise Preparations 55-58 in Table 4 from benzylamine and the appropriate cyclohexanone. Separation of the isomers was achieved in a similar way

TABLE 4

| Prep | Structure | Name | RT (min) | m/z (ES+) |
|---|---|---|---|---|
| 54 | 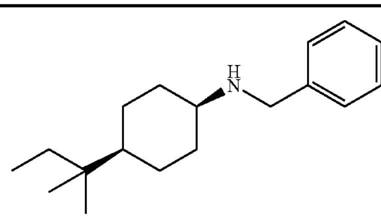 | cis-1-Benzylamino[4-(1,1-dimethylpropyl)]-cyclohexane | 2.84 | 260.2 [M + H]+ |
| 55 | 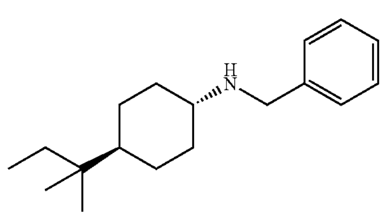 | trans-1-Benzylamino-[4-(1,1-dimethyl-propyl)]cyclohexane hydrochloride | 2.85 | 260.2 [M + H]+ |

TABLE 4-continued

| Prep | Structure | Name | RT (min) | m/z (ES+) |
|---|---|---|---|---|
| 56 | 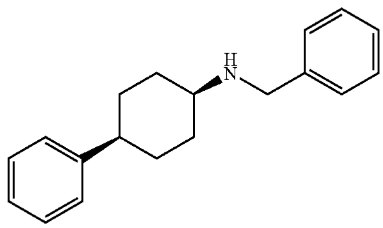 | cis-1-Benzylamino-4-phenylcyclohexane | 2.50 | 266.1 [M + H]+ |
| 57 | 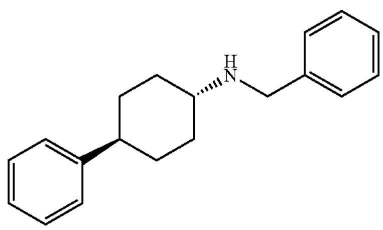 | tran-1-Benzylamino-4-phenylcyclohexane hydrochloride | 2.47 | 266.1 [M + H]+ |

Preparation 58: cis-4-Propylcyclohexylamine

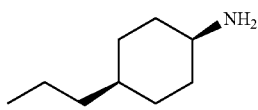

To a solution of cis-1-benzylamino-4-propylcyclohexane (Preparation 52) (1.59 g, 6.87 mmol) in EtOH (90 mL) was added cyclohexene (10 mL) and 10% palladium-on-carbon (550 mg). The mixture was refluxed for 12 h. After cooling the mixture was filtered through celite. Solvent was removed in vacuo to give the title compound: $\delta_H$ (CD$_3$OD): 0.95 (3H, t), 1.28-1.74 (13H, m), 2.95 (1H, m).

The procedure described in Preparation 58 was used to synthesise Preparations 59-63 in Table 5 from the corresponding benzylamines. All cis-isomers were converted into their hydrochloride salts by the method described in Preparation 54.

TABLE 5

| Prep | Structure | Name | $\delta_H$ (400 MHz, CD$_3$OD) |
|---|---|---|---|
| 59 | 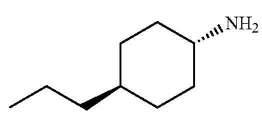 | trans-4-Propyl-cyclohexylamine hydrochloride | 0.94 (3H, t), 1.07 (2H, m), 1.22-1.46 (7H, m), 1.90 (2H, m), 2.06 (2H, m), 3.05 (1H, m) |
| 60 | 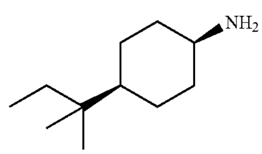 | cis-1-(1,1-Dimethyl-propyl)cyclohexyl-amine hydrochloride | 0.86 (3H, t), 0.88 (6H, s), 1.33 (3H, m), 1.35 (2H, q), 1.72 (2H, m), 1.80 (2H, m), 1.98 (2H, m), 3.52 (1H, m) |
| 61 | 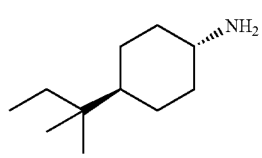 | trans-4-(1,1-Dimethyl-propyl)cyclohexyl-amine hydrochloride | 0.83-0.89 (9H, m), 1.13-1.27 (3H, m), 1.30-1.43 (4H, m), 1.84-1.94 (2H, m), 2.11 (2H, d), 3.03 (1H, m) |
| 62 | 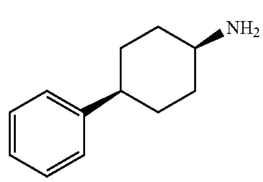 | cis-4-Phenyl-cyclohexylamine hydrochloride | 1.82-2.00 (8H, 2m), 2.74 (1H, m), 3.57 (1H, m), 7.21 (1H, m), 7.34 (4H, m) |

TABLE 5-continued

| Prep | Structure | Name | $\delta_H$ (400 MHz, CD$_3$OD) |
|---|---|---|---|
| 63 | 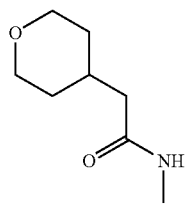 | trans-4-Phenyl-cyclohexylamine hydrochloride | 1.55-1.73 (4H, m), 1.98-2.07 (2H, m), 2.19 (2H, m), 2.53-2.67 (1H, m), 3.17-3.29 (1H, m), 7.19-7.38 (5H, m) |

Preparation 64:
N-Methyl-2-(tetrahydropyran-4-yl)acetamide

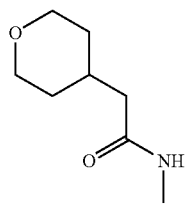

To a solution of (tetrahydropyran-4-yl)acetic acid (500 mg, 3.47 mmol) in thionyl chloride (10 mL) was added DMF (1 drop). The reaction was heated to reflux for 1 h, cooled to rt and the solvent removed in vacuo. The residue was redissolved in THF (5 mL) and added dropwise to a solution of methylamine hydrochloride (2.34 g, 34.7 mmol) and NaOH (1.11 g, 27.7 mmol) in water. The solution was stirred for 30 min and EtOAc (100 mL) added. The mixture was extracted with EtOAc (5×100 mL) and the combined organic phase dried (MgSO$_4$). Solvent was removed in vacuo to give the title compound: $\delta_H$ (CDCl$_3$) 1.14-1.33 (2H, m), 1.48-1.63 (3H, m), 1.97-2.07 (2H, m), 2.74 (3H, s), 3.26-3.41 (2H, m), 3.87 (2H, dd), 5.34 (1H, bs).

Preparation 65:
Methyl-[2-(tetrahydropyran-4-yl)ethyl]amine hydrochloride salt

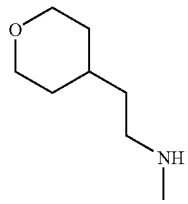

N-Methyl-2-(tetrahydropyran-4-yl)acetamide (Preparation 64) in THF (10 mL) was added to a solution of LiAlH$_4$ (99 mg, 2.60 mmol) in THF (10 mL). The reaction was refluxed for 2 h. After cooling to rt water (0.1 mL), NaOH (0.1N, 0.1 mL) and water (0.1 mL) were added sequentially, the mixture filtered through celite and the filtrate was dried (MgSO$_4$). Solvent was removed in vacuo. The residue was treated with MeOH (5 mL) and conc. HCl (0.2 mL), filtered and air dried to give the title compound: $\delta_H$ (CDCl$_3$) 1.19-1.34 (2H, m), 1.49-1.64 (3H, m), 1.71-1.80 (2H, m), 2.62 (3H, t), 2.87-2.99 (2H, m), 3.26-3.36 (2H, m), 3.88 (2H, dd).

Preparation 66:
6-(5-Formylquinolin-8-yloxy)nicotinonitrile

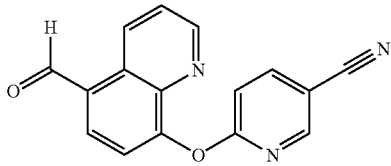

To a solution of 8-hydroxyquinoline-5-carbaldehyde (692 mg, 4 mmol) in sulfolane (8 mL) was added 2-chloro-5-cyanopyridine (552 mg, 4 mmol) and K$_2$CO$_3$ (1.7 g, 12 mmol). The reaction was heated at 90° C. for 2 h in a microwave. The reaction was cooled to rt and poured into water (100 mL). The resulting solid was filtered, washed with water, ether and air dried to give the title compound: RT=3.02 min; m/z (ES$^+$)=276.0 [M+H]$^+$.

Preparation 67:
6-(5-Formylquinolin-8-yloxy)nicotinamide

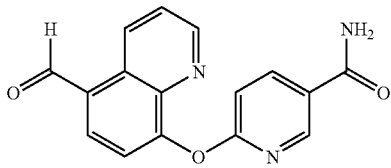

Using the procedure outlined in Preparation 2, 6-(5-formyl-quinolin-8-yloxy)-nicotinonitrile (Preparation 66) was converted to the title compound: RT=2.43 min; m/z (ES$^+$)=294.0 [M+H]$^+$.

Preparation 68:
7-Methoxybenzo[b]thiophene-4-carbaldehyde

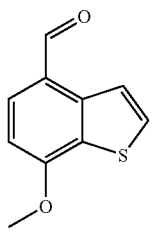

Phosphorous oxychloride (0.518 g, 17.7 mmol) was added to DMF (1.04 mL) under argon at rt. After 30 min 7-methoxybenzothiophene (0.5 g, 3.04 mmol) was added and the reaction was heated to 100° C. for 3.5 h. The reaction was cooled to rt and poured into a saturated Na$_2$CO$_3$ solution, extracted with ether (100 mL) and the organic phase dried (MgSO$_4$). Solvent was removed in vacuo to give the title compound: RT=3.34 min; m/z (ES$^+$)=193.2 [M+H]$^+$.

Preparation 69:
7-Hydroxybenzo[b]thiophene-4-carbaldehyde

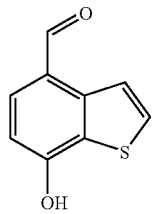

7-Methoxybenzo[b]thiophene-4-carbaldehyde (Preparation 68) (844 mg, 4.39 mmol) was added to a suspension of potassium tert-butoxide (1.5 g, 14.0 mmol) and diethylaminoethanethiol hydrochloride (1.12 g, 6.58 mmol) in DMF (22 mL). The mixture was refluxed for 1 h. After cooling the mixture was acidified to pH 1 with 1N HCl and the aqueous phase extracted with EtOAc. The organic phase was washed with water, brine and dried (MgSO$_4$). Solvent was removed in vacuo to give the title compound: RT=2.59 min; m/z (ES$^+$)=178.2 [M+H]$^+$.

Preparation 70: 6-(4-Formylbenzo[b]thiophen-7-yloxy)nicotinonitrile

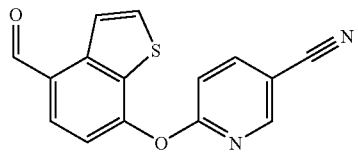

A suspension of 7-hydroxybenzo[b]thiophene-4-carbaldehyde (Preparation 69) (100 mg, 0.62 mmol), 6-chloronicotinonitrile (86 mg, 0.62 mmol) and K$_2$CO$_3$ (258 mg, 1.87 mmol) in sulfolane (3 mL) was heated in a microwave reactor at 130 W/80° C. for 4 h. The mixture was cooled, poured onto ice water and the resulting solid filtered and air-dried to give the title compound: RT=3.40 min; m/z (ES$^+$)=265.2 [M+H]$^+$.

Preparation 71:
6-(4-Formylbenzo[b]thiophen-7-yloxy)nicotinamide

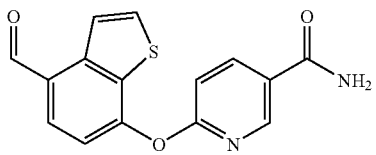

6-(4-Formylbenzo[b]thiophen-7-yloxy)nicotinonitrile (Preparation 70) (111 mg, 0.42 mmol) was added to K$_2$CO$_3$ (29 mg, 0.21 mmol) in DMSO (3 mL) followed by H$_2$O$_2$ solution (0.42 mL, 0.42 mmol). After 3 h water was added and the resulting solid filtered and air-dried to give the title compound: RT=2.93 min; m/z (ES$^+$)=283.3 [M+H]$^+$.

Preparation 72:
7-Methoxybenzofuran-4-carbaldehyde

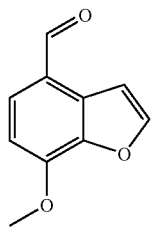

Using the procedure outlined in Preparation 68, 7-methoxybenzofuran gave the title compound: RT=2.99 min; m/z (ES$^+$)=177.2 [M+H]$^+$.

Preparation 73:
7-Hydroxybenzofuran-4-carbaldehyde

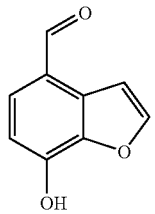

Using the procedure outlined in Preparation 69, 7-methoxybenzofuran-4-carbaldehyde (Preparation 73) gave the title compound: RT=2.59 min; m/z (ES$^+$)=161.2 [M+H]$^+$.

Preparation 74:
6-(4-Formylbenzofuran-7-yloxy)nicotinonitrile

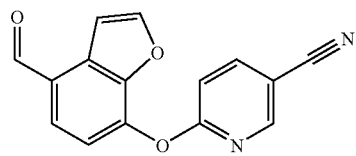

Using the procedure outlined in Preparation 70, 7-hydroxybenzofuran-4-carbaldehyde (preparation 73) and 6-chloronicotinonitrile gave the title compound: RT=3.40 min; m/z (ES$^+$)=265.2 [M+H]$^+$.

Preparation 75: 6-(4-Formylbenzofuran-7-yloxy)nicotinamide

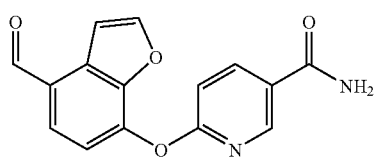

Using the procedure outlined in Preparation 71 6-(4-formylbenzofuran-7-yloxy)-nicotinonitrile (Preparation 74) gave the title compound: RT=2.93 min; m/z (ES$^+$)=283.2 [M+H]$^+$.

Preparation 76: 5,6-Difluoroindan-1-one

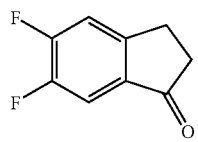

To a solution of 3,4-difluorocinnamic acid (5.0 g, 26.9 mmol) in DCM (35 mL) at 0° C., was added DMF (1 drop) and oxalyl chloride (4.7 mL, 53.8 mmol). The reaction mixture was warmed to rt and stirred for 16 h. The solvents were removed in vacuo and the residue azeotroped with toluene (2×20 mL). The residue was redissolved in carbon disulfide (20 mL) and added to a solution of aluminum trichloride (12.4 g, 94.1 mmol) in carbon disulfide (50 mL) at 0° C. The reaction mixture was stirred at 0° C. for 30 min, heated to reflux for 4 h and then cooled to rt. The reaction mixture was poured into ice, extracted with EtOAc (2×500 mL) and the combined organic phase dried (MgSO$_4$). Solvent was removed in vacuo and the residue purified by column chromatography (EtOAc:isohexane 1:9) to give the title compound: $\delta_H$(CDCl$_3$) 2.73 (2H, t), 3.17 (2H, t), 7.32 (1H, t), 7.43 (1H, t).

Preparation 77: 5,6-Difluoroindan-1,2-dione 2-oxime

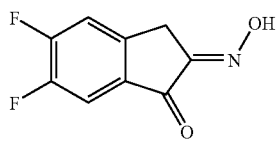

To a solution of 5,6-difluoroindan-1-one (Preparation 76) (3.1 g, 18.4 mmol) in MeOH at 40° C. was added isoamylnitrite (3.22 mL, 23.9 mmol) followed by conc. HCl (1.8 mL). The reaction was stirred at 40° C. for 45 min, cooled to rt and poured into water (50 mL). The precipitate was collected by filtration and air-dried to give the title compound: $\delta_H$(DMSO-d$_6$) 3.77 (2H, s), 7.72-7.85 (2H, m), 12.79 (1H, s).

Preparation 78: 2-Amino-5,6-difluoroindan-1-one

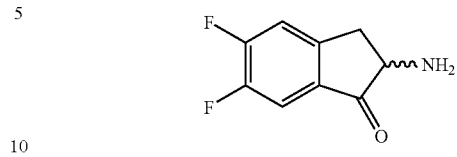

5,6-Difluoroindan-1,2-dione 2-oxime (Preparation 77) (2.70 g, 13.7 mmol) was dissolved in acetic acid (70 mL) and 10% Palladium on carbon (717 mg) added. The reaction mixture was hydrogenated at 50 psi for 72 h, filtered through a pad of celite and washed with chloroform (100 mL). The resulting precipitate was collected by filtration and air dried to give the title compound: $\delta_H$(DMSO-d$_6$) 3.11 (1H, dd), 3.56 (1H, dd), 4.34 (1H, dd), 7.74-7.94 (2H, m), 8.75 (2H, bs).

Preparation 79: (5,6-Difluoro-1-oxoindan-2-yl)carbamic acid benzyl ester

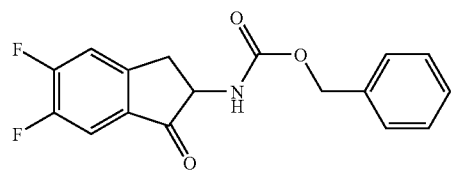

To 2-amino-5,6-difluoroindan-1-one (Preparation 78) (165 mg, 0.90 mmol) in saturated NaHCO$_3$ (15 mL) was added benzyl chloroformate (0.15 mL, 1.08 mmol). The reaction mixture was stirred at rt for 1 h. The mixture was extracted with EtOAc (25 mL) and the organic phase washed with water (20 mL), brine (20 mL) and dried (MgSO$_4$). Solvent was removed in vacuo and the residue purified by column chromatography (MeOH:DCM 1:99) to give the title compound: RT=3.50 min; m/z (ES$^+$)=318.1 [M+H]$^+$.

Preparation 80: 6,7-Difluoro-3,3a,4,8b-tetrahydroindeno[2,1-d]oxazol-2-one

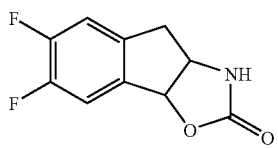

To (5,6-difluoro-1-oxoindan-2-yl)carbamic acid benzyl ester (Preparation 79) (238 mg, 0.75 mmol) was added TFA (5 mL) and triethylsilane (0.59 mL, 3.75 mmol). The reaction mixture was stirred for 24 h. Solvent was removed in vacuo and the residue purified by column chromatography (MeOH:DCM 5:95) to give the title compound: $\delta_H$(CDCl$_3$) 3.06-3.15 (1H, m), 3.29 (1H, dd), 4.79 (1H, t), 5.98 (1H, d), 7.10 (1H, dd), 7.27-7.35 (1H, m), 12.02 (1H, s).

Preparation 81: 5,6-Difluoroindan-2-ylamine

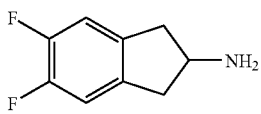

A solution of 6,7-difluoro-3,3a,4,8b-tetrahydroindeno[2,1-d]oxazol-2-one (Preparation 80) (145 mg, 0.69 mmol) and 10% palladium on carbon (15 mg) in EtOH (10 mL) was stirred under $H_2$ for 1 h. The reaction mixture was filtered through celite and the solvent removed in vacuo to give the title compound: $\delta_H$ (CDCl$_3$) 2.66 (2H, dd), 3.15 (2H, dd), 3.86-3.94 (1H, m), 7.00 (2H, t).

Preparation 82: 3-Chloro-4-(4-formylnaphthalen-1-yloxy)benzonitrile

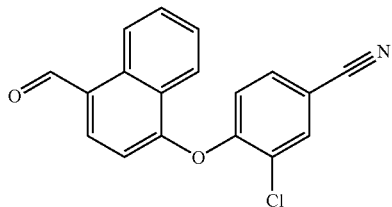

To a solution of 3-chloro-4-fluorobenzonitrile (1.09 g, 7.00 mmol) in DMSO (25 mL) was added 4-hydroxy-1-napthaldehyde (1.20 g, 7.0 mmol) and caesium carbonate (4.55 g, 14.0 mmol). The reaction mixture was heated to 80° C. for 24 h. After cooling to rt the mixture was partitioned between EtOAc (40 mL) and saturated NaHCO$_3$ (50 mL), and the aqueous phase washed with EtOAc (50 mL). Solvent was removed in vacuo and the residue purified by column chromatography (EtOAc:isohexane, 2:8) to give the title compound: RT=4.10 min; m/z (ES$^+$)=NO IONISATION [M+H]$^+$. $\delta_H$(DMSO) 7.10 (1H, t), 7.46 (1H, d), 7.78 (1H, t), 7.88 (1H, t), 7.94 (1H, d), 8.19 (1H, d), 8.32 (1H, d), 8.37 (1H, d), 9.28 (1H, d), 10.33 (1H, s).

Preparation 83: 3-Chloro-4-{4-[(3-methylbutylamino)methyl]naphthalen-1-yloxy}benzonitrile

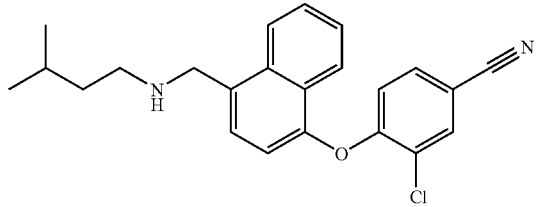

To a solution of 3-chloro-4-(4-formylnaphthalen-1-yloxy)benzonitrile (Preparation 82) (800 mg, 2.60 mmol) in DCM (35 mL) was added acetic acid (0.7 mL, 7.80 mmol), 3-methylbutylamine (0.91 mL, 7.80 mmol) and NaBH(OAc)$_3$ (1.65 g, 7.80 mmol). The reaction was stirred at rt for 16 h. The mixture was partitioned between DCM (150 mL) and saturated NaHCO$_3$ (200 mL) and the organic phase dried (MgSO$_4$). Solvent was removed in vacuo and the residue purified by column chromatography (EtOAc:isohexane 1:1) to give the title compound: RT=3.01 min; m/z (ES$^+$)=379.3, 381.2 [M+H]$^+$.

Preparation 84: 3-Fluoro-4(4-formylnaphthalen-1-yloxy)benzonitrile

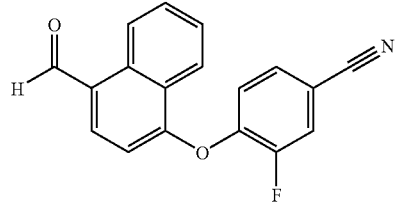

Using the procedure outlined in Preparation 82, 4-hydroxynaphthaldehyde and 3,4-difluorobenzonitrile were converted to the title compound: RT=3.90 min; m/z (ES$^+$)=292.1 [M+H]$^+$.

Preparation 85: 3-Fluoro-4(4-formylnaphthalen-1-yloxy)benzamide

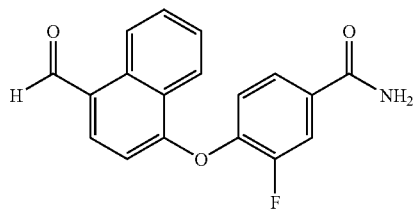

Using the procedure outlined in Preparation 19, 3-fluoro-4(4-formylnaphthalen-1-yloxy)benzonitrile (Preparation 84) was converted to the title compound: RT=3.37 min; m/z (ES$^+$)=310.11 [M+H]$^+$.

Preparation 86: 4-[(3-Methylbutylamino)methyl]naphthalen-1-ol

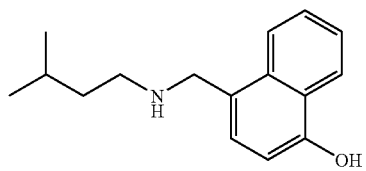

Using the procedure outlined in Preparation 83, 4-hydroxynaphthaldehyde and 3-methylbutylamine were converted to the title compound: RT=2.38 min; m/z (ES$^+$)=144.1 [M+H]$^+$.

Preparation 87: 4-{4-[(3-Methylbutylamino)methyl]naphthalen-1-yloxy}benzonitrile

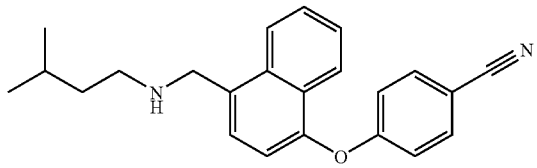

Using the procedure outlined in Example 1, 4-(4-formyl-naphthalen-1-yloxy)benzonitrile (Preparation 28) and 3-methylbutylamine were converted to the title compound: RT=2.88 min; m/z (ES$^+$)=345.3 [M+H]$^+$.

Preparation 88: 4-Chloroquinoline-8-carbonitrile

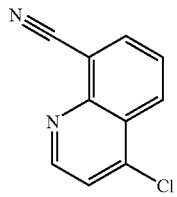

4-Oxo-1,4-dihydroquinoline-8-carbonitrile (0.40 g, 0.24 mmol, WO2004/113303) and phosphorous oxychloride (10 mL) were heated to 100° C. for 1.5 h. Solvent removed in vacuo. EtOAc (50 mL) was added and organic phase washed with sat. aqueous Na$_2$CO$_3$ solution, brine (20 mL) and dried (MgSO$_4$). Solvent removed in vacuo to give the title compound: RT=3.09 min; m/z (ES$^+$)=189.0 [M+H]$^+$.

Preparation 89: C-(4-Chloroquinolin-8-yl)methylamine

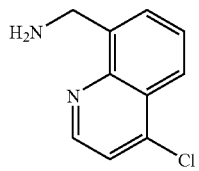

To 4-chloroquinoline-8-carbonitrile (Preparation 88) (422 mg 2.24 mmol) in toluene (20 mL) at −78° C. was added dropwise DIBAL-H (6.73 mL/1M solution in toluene, 6.73 mmol). After 20 min at −78° C. the mixture was allowed to warm to −40° C. The reaction mixture was then re-cooled to −78° C. and DIBAL-H (2.0 mL/1M solution in toluene, 2.0 mmol) was added. After 1 h water (1 mL), MeOH (5 mL) and then NH$_4$Cl$_{(aq)}$ (10 mL) were added. After addition of EtOAc (20 mL) the mixture was stirred vigorously for 14 h at rt. The mixture was extracted with EtOAc (3×20 mL) and the combined organic phase washed with brine (20 mL) and dried (MgSO$_4$). Solvent removed in vacuo to give the title compound: RT=2.10 min; m/z (ES$^+$)=193.0 [M+H]$^+$.

Preparation 90: 4-(8-Aminomethylquinolin-4-yloxy)benzamide

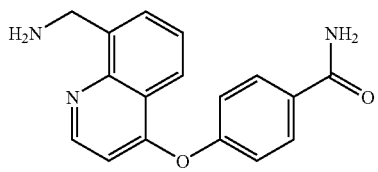

A mixture of C-(4-chloroquinolin-8-yl)methylamine (Preparation 89) (129 mg, 0.67 mmol), K$_2$CO$_3$ (186 mg, 1.34 mmol) and 4-hydroxybenzamide (110 mg, 0.81 mmol) in DMF (4 mL) were heated in a microwave at 100° C. for 40 min (150 W). Solvent removed in vacuo. The mixture was partitioned between EtOAc (50 mL) and water (20 mL), and the aqueous phase was further extracted with EtOAc (2×20 mL). The combined organic phase was washed with brine (20 mL) and dried (MgSO$_4$). Solvent was removed in vacuo and the residue purified by column chromatography (0.25% to 0.75% NH$_4$OH$_{(aq)}$, 2% to 8% MeOH in DCM) to give the title compound: RT=2.15 min; m/z (ES$^+$)=294.1 [M+H]$^+$.

Preparation 91: 2-(4-Formylnaphthalen-1-yloxy)isonicotinamide

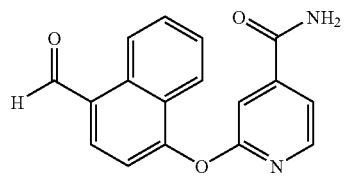

To a solution of 4-hydroxy-1-naphthaldehyde (500 mg, 2.9 mmol) and 2-chloro-4-cyanopyridine (402 mg, 2.9 mmol) in DMF (4 mL) was added K$_2$CO$_3$ (2.01 g, 14.52 mmol). The reaction was heated for 1 h at 70° C. in a microwave. The mixture was diluted with EtOAc (100 mL), washed with water (2×50 mL) and the aqueous phase extracted with EtOAc (2×50 mL). The organic phase was washed with water (100 mL), 1M NaOH (3×60 mL), brine (50 mL) and dried (MgSO$_4$). Solvent was removed in vacuo and the residue purified by column chromatography (SiO$_2$, NH$_4$OH:MeOH:DCM, 0.2:2:98) to give the title compound: RT=3.02 min; m/z (ES$^+$)=293.1 [M+H]$^+$.

Example 1

6-{4-[(2-Cyclopentylethylamino)methyl]naphthalen-1-yloxy}nicotinamide

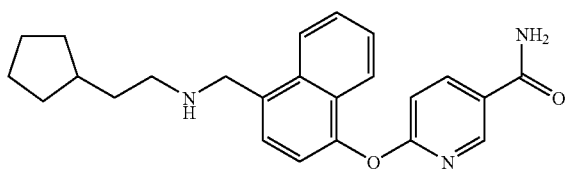

To a solution of 6-(4-formylnaphthalen-1-yloxy)nicotinamide (Preparation 2) (200 mg, 0.7 mmol) in MeOH (10 mL) was added 2-cyclopentyl ethylamine (116 mg, 1.0 mmol) and 4 Å molecular sieves (200 mg). The mixture was stirred for 16 h before adding NaBH$_4$ (130 mg, 3.4 mmol). After 1.5 h water (1 mL) was added and the mixture filtered. Solvent was removed in vacuo and the residue purified by column chromatography (0.5% NH$_3$: 2% MeOH:DCM) to give the title compound: RT=2.68 min; m/z (ES$^+$)=390.2 [M+H]$^+$.

The procedure described in Example 1 was used to prepare Examples 2-90 from the corresponding amide (Preparation X in Table 6) and the appropriate amine. The secondary amines in Examples 34-37 were converted into the hydrochloride salts using the procedure outlined in Preparation 53:

TABLE 6

| Ex | Structure | Name | X | RT (min) | m/z (ES⁺) |
|---|---|---|---|---|---|
| 2 | 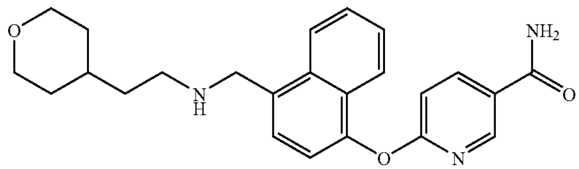 | 6-(4-{[2-(Tetrahydro-pyran-4yl)-ethylamino]methyl}-naphthalen-1-yloxy)-nicotinamide | 2 | 2.42 | 406.2 [M + H]⁺ |
| 3 | 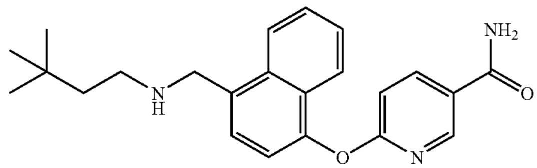 | 6-{4-[(3,3-Dimethyl-butylamino)methyl]-naphthalen-1-yloxy}-nicotinamide | 2 | 2.72 | 378.0 [M + H]⁺ |
| 4 | 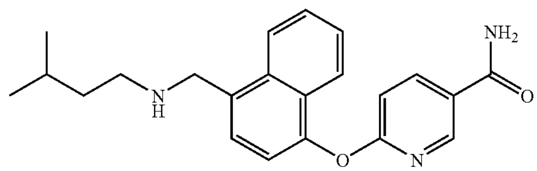 | 6-{4-[(3-Methyl-butylamino)methyl]-naphthalen-1-yloxy}-nicotinamide | 2 | 2.47 | 364.2 [M + H]⁺ |
| 5 | 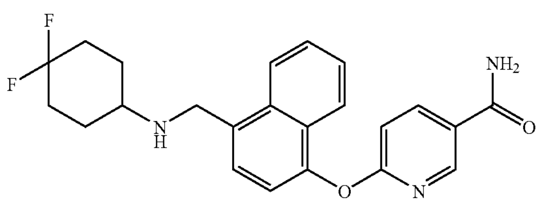 | 6-{4-[(4,4-Difluoro-cyclohexylamino)-methyl]naphthalen-1-yloxy}nicotinamide | 2 | 2.48 | 412.0 [M + H]⁺ |
| 6 | 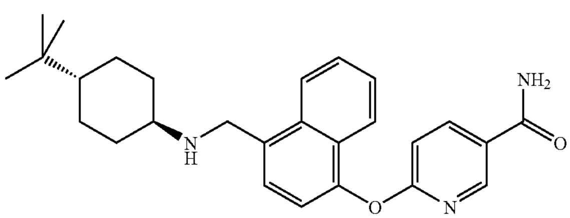 | 6-{4-[trans-(4-tert-Butylcyclohexyl-amino)methyl]-naphthalen-1-yloxy}nicotinamide | 2 | 3.06 | 432.1 [M + H]⁺ |
| 7 | 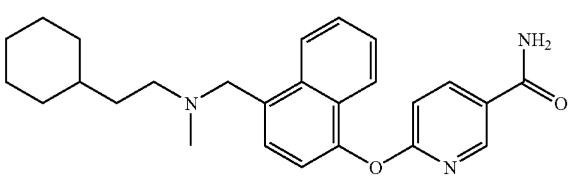 | 6-(4-{[(2-Cyclohexyl-ethyl)methylamino]-methyl}naphthalen-1-yloxy)nicotinamide | 2 | 2.72 | 418.1 [M + H]⁺ |
| 8 | 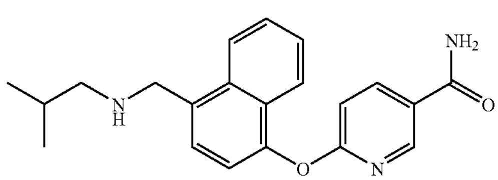 | 6-[4-(Isobutylamino-methyl)naphthalen-1-yloxy]nicotinamide | 2 | 2.36 | 350.0 [M + H]⁺ |
| 9 | 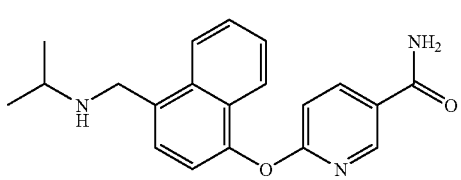 | 6-[4-(Isopropylamino-methyl)naphthalen-1-yloxy]nicotinamide | 2 | 2.42 | 336.0 [M + H]⁺ |

TABLE 6-continued

| Ex | Structure | Name | X | RT (min) | m/z (ES+) |
|---|---|---|---|---|---|
| 10 | 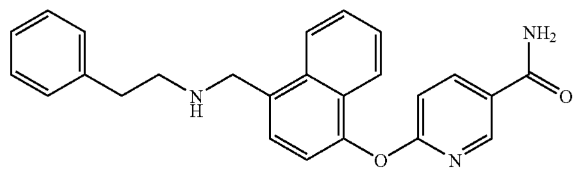 | 6-[4-(Phenethylamino-methyl)naphthalen-1-yloxy]nicotinamide | 2 | 2.62 | 398.0 [M + H]+ |
| 11 | 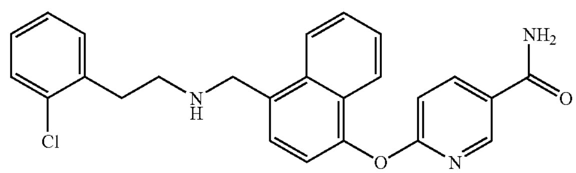 | 6-(4-{[2-(2-Chloro-2-phenyl)ethylamino]-methyl}naphthalen-1-yloxy)nicotinamide | 2 | 2.77 | 431.9 [M + H]+ |
| 12 | 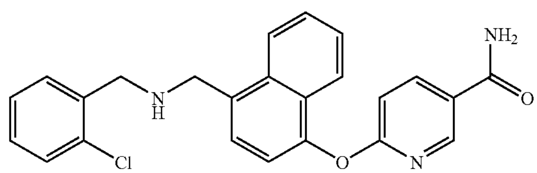 | 6-{4-[(2-Chloro-benzylmaino)methyl]-naphthalen-1-yloxy}-nicotinamide | 2 | 2.64 | 417.9 [M + H]+ |
| 13 | 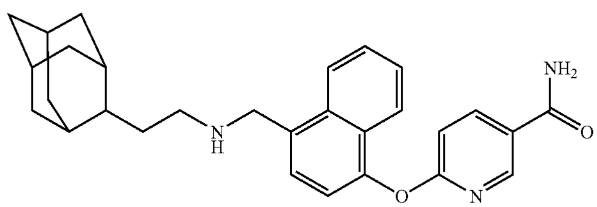 | 6-{4-[(2-Adamantan-2-ylethylamino)methyl]-naphthalen-1-yloxy}-nicotinamide | 2 | 3.01 | 456.0 [M + H]+ |
| 14 | 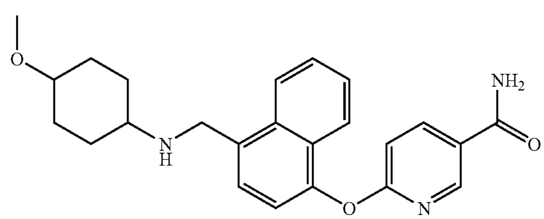 | 6-{4-[(4-Methoxy-cyclohexylamino)-methyl]naphthalen-1-yloxy}nicotinamide | 2 | 2.38 | 406.2 [M + H]+ |
| 15 | 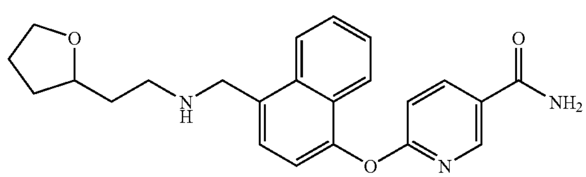 | 6-(4-{[2-(Tetrahydro-furan-2-yl)ethylamino]-methyl}naphthalen-1-yloxy)nicotinamide | 2 | 2.42 | 392.3 [M + H]+ |
| 16 | 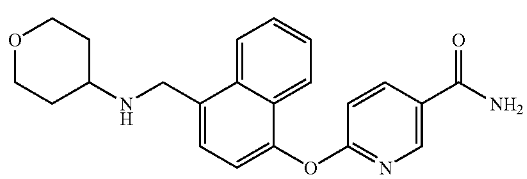 | 6-{4-[(Tetrahydro-pyran-4-ylamino)-methyl]naphthalen-1-yloxy}nicotinamide | 2 | 2.23 | 378.2 [M + H]+ |
| 17 | 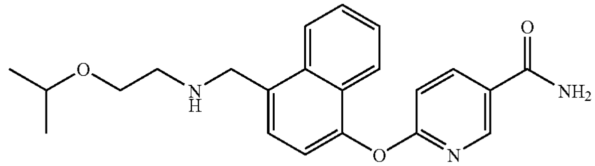 | 6-{4-[(2-Isoproproxy-ethylamino)methyl]-naphthalen-1-yloxy}nicotinamide | 2 | 2.44 | 380.2 [M + H]+ |

TABLE 6-continued

| Ex | Structure | Name | X | RT (min) | m/z (ES+) |
|---|---|---|---|---|---|
| 18 | 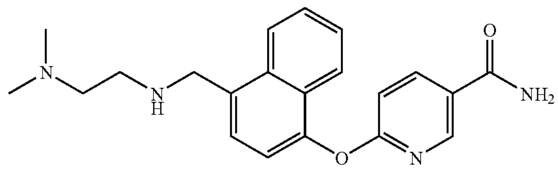 | 6-{4-[(2-Dimethyl-aminoethylamino)-methyl]naphthalen-1-yloxy}nicotinamide | 2 | 1.95 | 365.2 [M + H]+ |
| 19 | 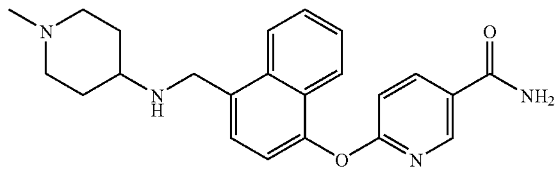 | 6-{4-[(1-Methyl-piperidin-4-ylamino)-methyl]naphthalen-1-yloxy}nicotinamide | 2 | 1.99 | 391.2 [M + H]+ |
| 20 | 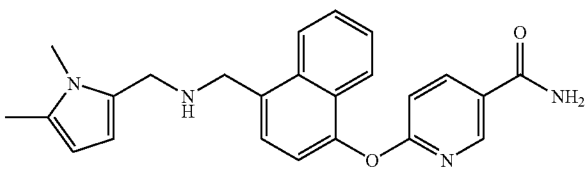 | 6-(4-{[(1,5-Dimethyl-1H-pyrrol-2-ylmethyl)-amino]methyl}-naphthalen-1-yloxy)-nicotinamide | 2 | 2.57 | 401.2 [M + H]+ |
| 21 | 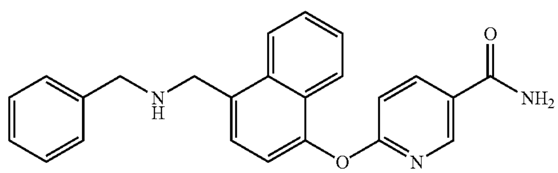 | 6-[4-(Benzylamino-methyl)naphthalen-1-yloxy]nicotinamide | 2 | 2.41 | 384.2 [M + H]+ |
| 22 | 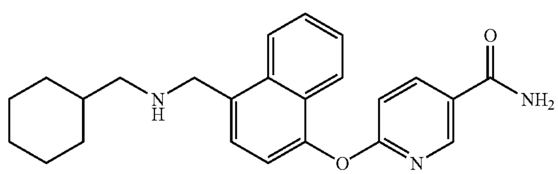 | 6-{4-[(Cyclohexyl-methylamino)methyl]-naphthalen-1-yloxy}-nicotinamide | 2 | 2.64 | 390.3 [M + H]+ |
| 23 | 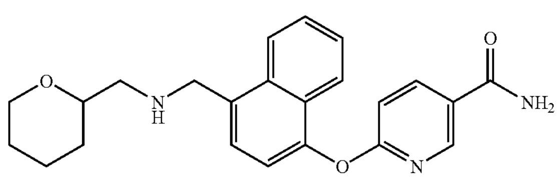 | 6-(4-{[(Tetrahydro-pyran-2-ylmethyl)-amino]methyl}-naphthalen-1-yloxy)-nicotinamide | 2 | 2.50 | 392.2 [M + H]+ |
| 24 | 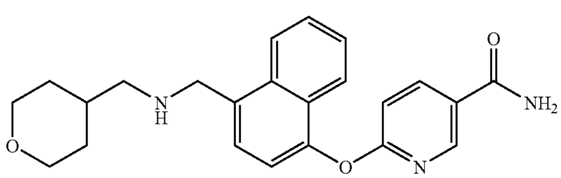 | 6-(4-{[(Tetrahydro-pyran-4-ylmethyl)-amino]methyl}-naphthalen-1-yloxy)-nicotinamide | 2 | 2.34 | 392.2 [M + H]+ |
| 25 | 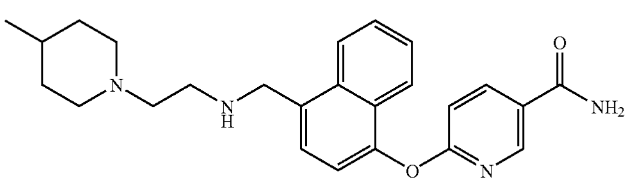 | 6-(4-{[2-(4-Methyl-piperidin-1-yl)-ethylamino]methyl}-naphthalen-1-yloxy)nicotinamide | 2 | 1.98 | 419.3 [M + H]+ |

TABLE 6-continued

| Ex | Structure | Name | X | RT (min) | m/z (ES+) |
|---|---|---|---|---|---|
| 26 | 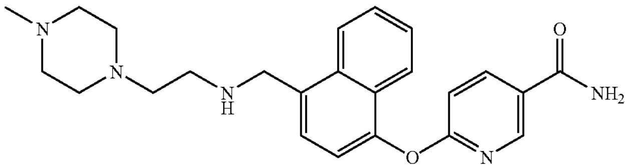 | 6-(4-{[2-(4-Methyl-piperazin-1-yl)-ethylamino]methyl}-naphthalen-1-yloxy)-nicotinamide | 2 | 1.92 | 420.3 [M + H]+ |
| 27 | 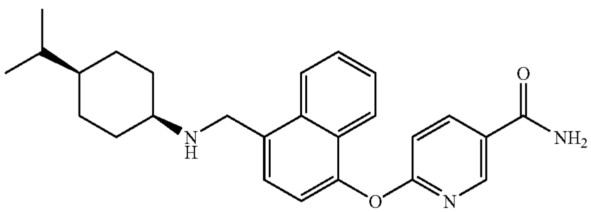 | 6-{4-[(cis-4-Isopropyl-cyclohexylamino)-methyl]naphthalen-1-yloxy}nicotinamide | 2 | 2.79 | 418.2 [M + H]+ |
| 28 | 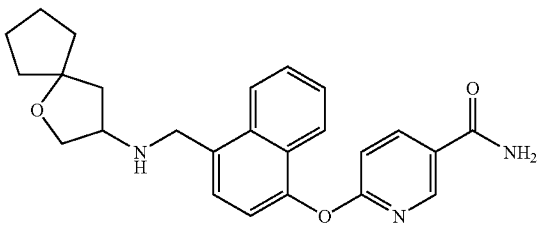 | 6-{4-[(1-Oxaspiro-[4.4]non-3-ylamino)-methyl]naphthalen-1-yloxy}nicotinamide | 2 | 2.45 | 418.2 [M + H]+ |
| 29* | 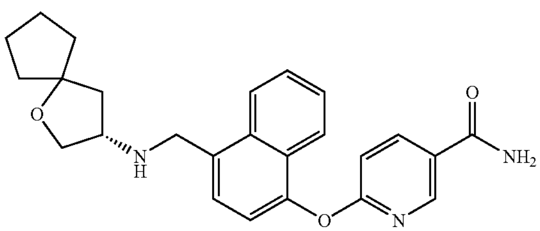 | 6-(4-{[(S)-(1-Oxa-spiro[4.4]non-3-yl)-amino]methyl}-naphthalen-1-yloxy)-nicotinamide | 2 | 2.45 | 418.2 [M + H]+ |
| 30* | 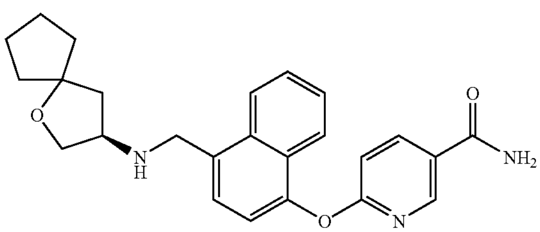 | 6-(4-{[(R)-(1-Oxa-spiro[4.4]non-3-yl)-amino]methyl}-naphthalen-1-yloxy)-nicotinamide | 2 | 2.45 | 418.2 [M + H]+ |
| 31 | 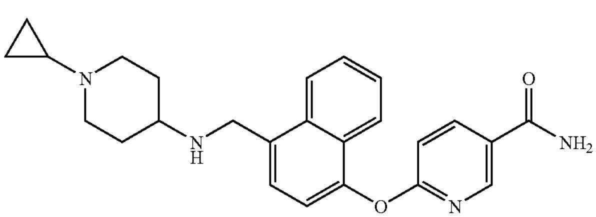 | 6-{4-[(1-Cyclopropyl-piperidin-4-ylamino)-methyl]naphthalen-1-yloxy}nicotinamide | 2 | 1.97 | 417.3 [M + H]+ |
| 32 | 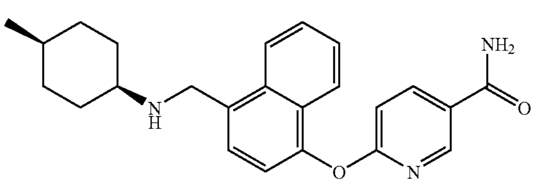 | 6-{4-[cis-(4-Methyl-cyclohexylamino)-methyl]naphthalen-1-yloxy}nicotinamide | 2 | 2.60 | 319.2 [M + H]+ |

TABLE 6-continued

| Ex | Structure | Name | X | RT (min) | m/z (ES+) |
|---|---|---|---|---|---|
| 33 | 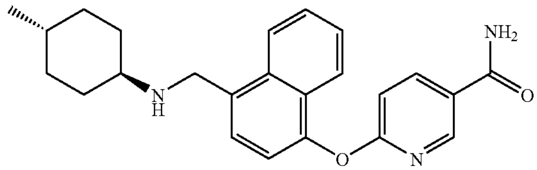 | 6-{4-[trans(4-Methyl-cyclohexylamino)-methyl]naphthalen-1-yloxy}nicotinamide | 2 | 2.42 | 391.2 [M + H]+ |
| 34 | 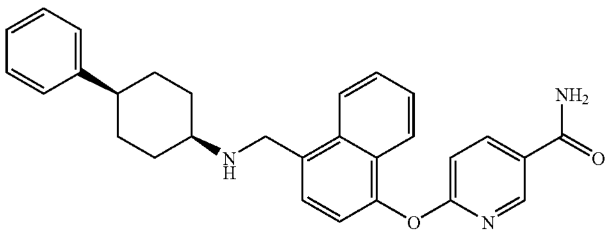 | 6-{4-[cis-(4-Phenyl-cyclohexylamino)-methyl]naphthalen-1-yloxy}nicotinamide hydrochloride | 2 | 2.90 | 452.2 [M + H]+ |
| 35 | 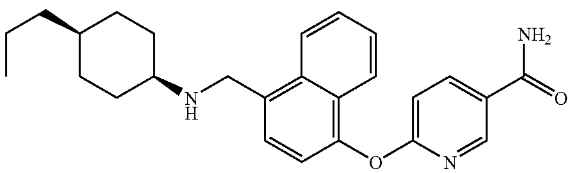 | 6-{4-[cis-(4-Propyl-cyclohexylamino)-methyl]naphthalen-1-yloxy}nicotinamide hydrochloride | 2 | 2.84 | 418.3 [M + H]+ |
| 36 | 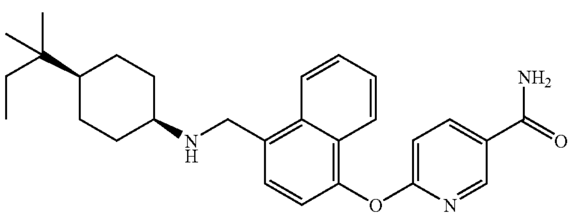 | 6-(4-{[cis-4-(1,1-Dimethylpropyl)-cyclohexylamino]-methyl}naphthalen-1-yloxy)nicotinamide hydrochloride | 2 | 3.07 | 446.3 [M + H]+ |
| 37 | 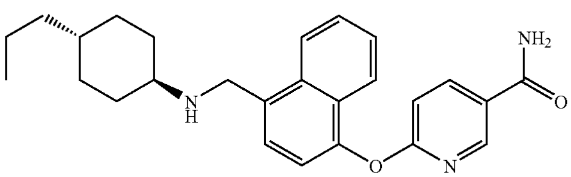 | 6-{4-[trans-(4-Propyl-cyclohexylamino)-methyl]naphthalen-1-yloxy}nicotinamide hydrochloride | 2 | 2.87 | 418.3 [M + H]+ |
| 38 | 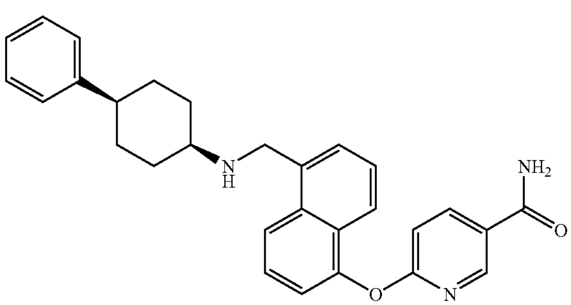 | 6-{4-[cis-(4-Phenyl-cyclohexylamino)-methyl]naphthalen-1-yloxy}nicotinamide | 2 | 2.84 | 452.2 [M + H]+ |
| 39 | 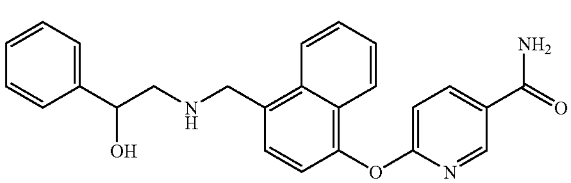 | 6-{4-[(2-Hydroxy-2-phenylethylamino)-methyl]naphthalen-1-yloxy}nicotinamide | 2 | 2.55 | 414.0 [M + H]+ |

TABLE 6-continued

| Ex | Structure | Name | X | RT (min) | m/z (ES+) |
|---|---|---|---|---|---|
| 40 | 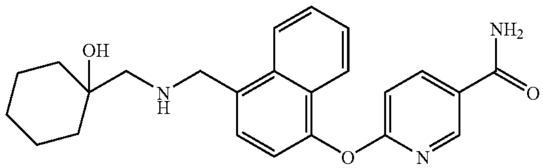 | 6-(4-{[(1-Hydroxy-cyclohexylmethyl)-amino]methyl}-naphthalen-1-yloxy)-nicotinamide | 2 | 2.49 | 405.5 [M + H]+ |
| 41 | 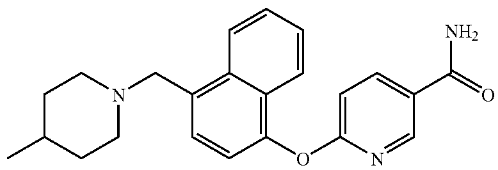 | 6-[4-(4-Methyl-piperidin-1-ylmethyl)-naphthalen-1-yloxy]-nicotinamide | 2 | 2.46 | 376.5 [M + H]+ |
| 43 | 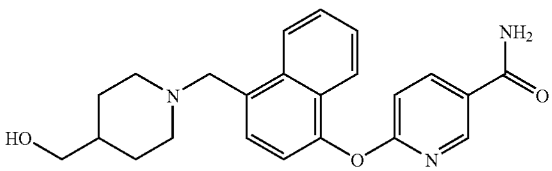 | 6-[4-(4-Hydroxy-methylpiperidin-1-ylmethyl)naphthalen-1-yloxy]nicotinamide | 2 | 2.26 | 392.5 [M + H]+ |
| 44 | 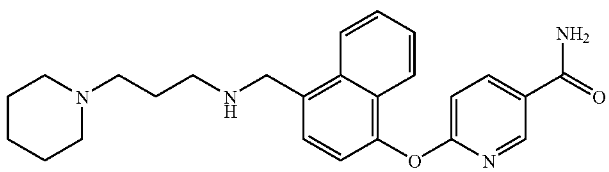 | 6-{4-[(3-Piperidin-1-yl-propylamino)methyl]-naphthalen-1-yloxy}-nicotinamide | 2 | 2.08 | 419.5 [M + H]+ |
| 45 | 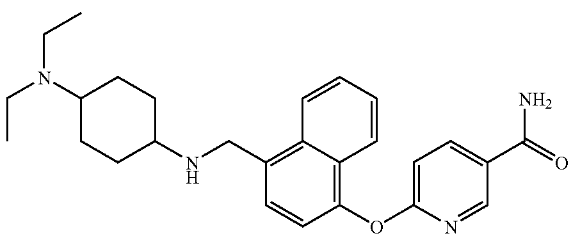 | 6-{4-[(4-Diethylamino-cyclohexylamino)-methyl]naphthalen-1-yloxy}nicotinamide | 2 | 2.03 | 447.6 [M + H]+ |
| 46 | 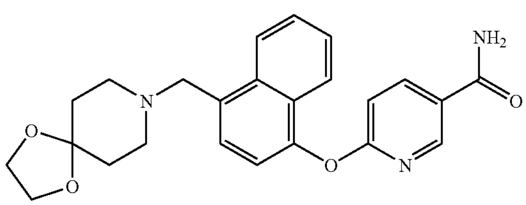 | 6-[4-(1,4-Dioxa-8-aza-spiro[4.5]dec-8-ylmethyl)naphthalen-1-yloxy]nicotinamide | 2 | 2.39 | 420.5 [M + H]+ |
| 47 | 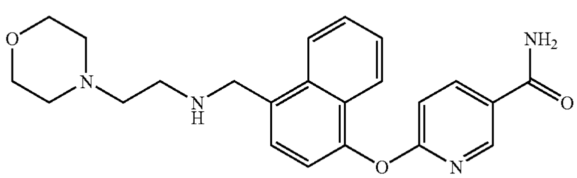 | 6-{4-[(2-Morpholin-4-ylethylamino)methyl]-naphthalen-1-yloxy}-nicotinamide | 2 | 2.10 | 407.5 [M + H]+ |
| 48 | 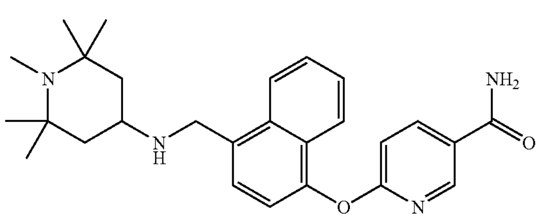 | 6-{4-[1,2,2,6,6-Pentamethylpiperidin-4-ylamino)methyl]-naphthalen-1-yloxy}-nicotinamide | 2 | 2.10 | 447.5 [M + H]+ |

TABLE 6-continued

| Ex | Structure | Name | X | RT (min) | m/z (ES+) |
|---|---|---|---|---|---|
| 49 | 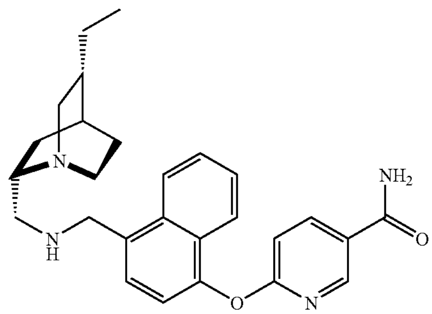 | 6-(4-{[(5-Ethyl-1-azabicyclo[2.2.2]oct-2-ylmethyl)amino]methyl}naphthalen-1-yloxy)nicotinamide | 2 | 2.18 | 445.5 [M + H]+ |
| 50 | 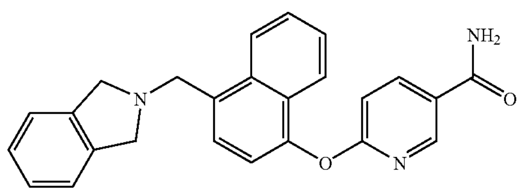 | 6-[4-(1,3-Dihydroisoindol-2-ylmethyl)naphthalen-1-yloxy]nicotinamide | 2 | 2.54 | 395.5 [M + H]+ |
| 51 | 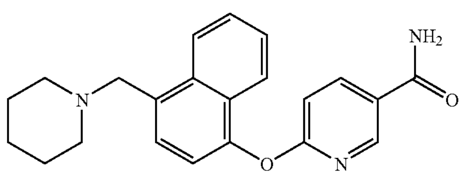 | 6-(4-Piperidin-1-ylmethylnaphthalen-1-yloxy)nicotinamide | 2 | 2.29 | 361.5 [M + H]+ |
| 52 | 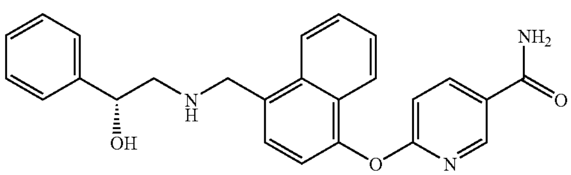 | 6-{4-[((R)-2-Hydroxy-2-phenylethylamino)methyl]naphthalen-1-yloxy}nicotinamide | 2 | 2.52 | 414.5 [M + H]+ |
| 53 | 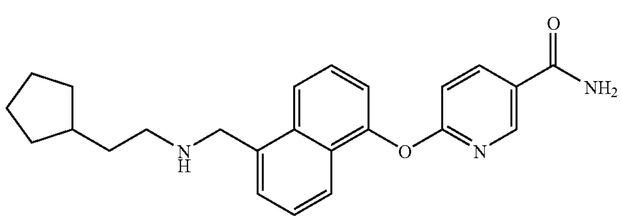 | 6-{5[(2-Cyclopentylethylamino)methyl]naphthalen-1-yloxy}nicotinamide | 35 | 2.75 | 390.2 [M + H]+ |
| 54 | 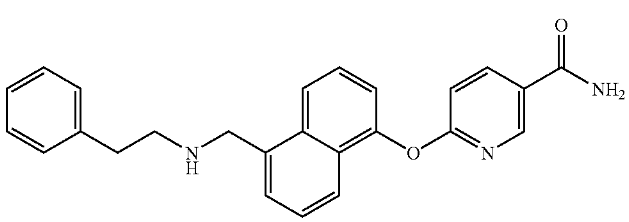 | 6-[5-(Phenethylaminomethyl)naphthalen-1-yloxy]nicotinamide | 35 | 2.62 | 398.2 [M + H]+ |
| 55 | 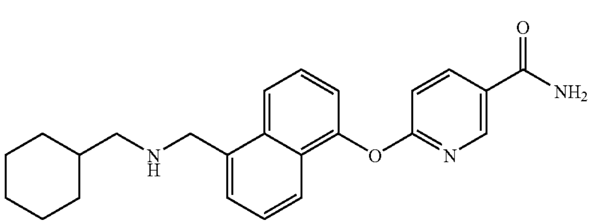 | 6-{5-[(Cyclohexylmethylamino)methyl]naphthalen-1-yloxy}nicotinamide | 35 | 2.60 | 390.2 [M + H]+ |

TABLE 6-continued

| Ex | Structure | Name | X | RT (min) | m/z (ES+) |
|----|-----------|------|---|----------|-----------|
| 56 | 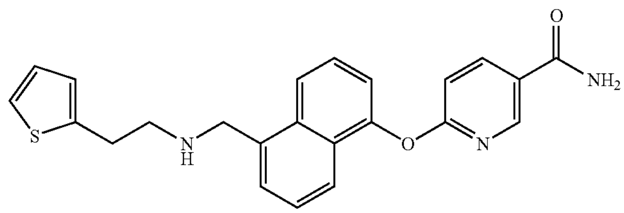 | 6-{5-[(2-Thiophen-2-ylethylamino)methyl]-naphthalen-1-yloxy}-nicotinamide | 35 | 2.57 | 404.2 [M + H]+ |
| 57 | 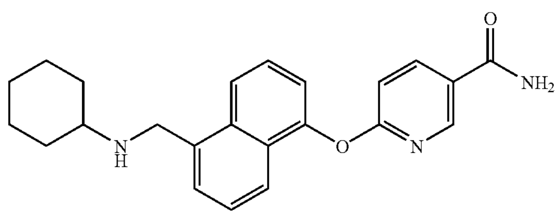 | 6-(5-Cyclohexylamino-methylnaphthalen-1-yloxy)nicotinamide | 35 | 2.54 | 376.3 [M + H]+ |
| 58 | 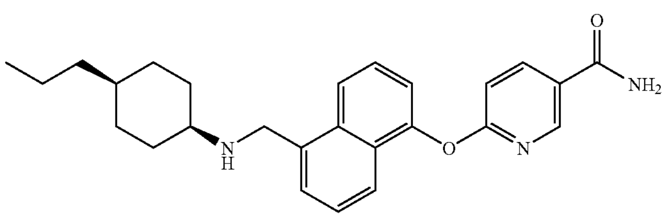 | 6-{5-[cis-(4-Propyl-cyclohexylamino)-methyl]naphthalen-1-yloxy}nicotinamide | 35 | 2.92 | 418.3 [M + H]+ |
| 59 | 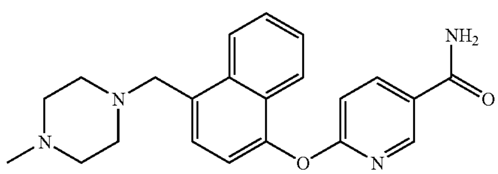 | 6-[4-(4-Methyl-piperazin-1-ylmethyl)-naphthalen-1-yloxy]-nicotinamide | 2 | 2.23 | 377.3 [M + H]+ |
| 60 | 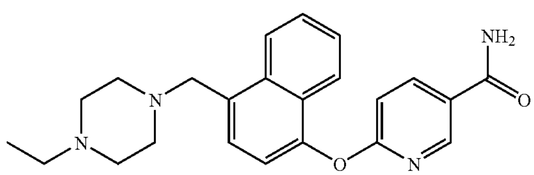 | 6-[4-(4-Ethylpiperazin-1-ylmethyl)-naphthalen-1-yloxy]-nicotinamide | 2 | 2.27 | 391.3 [M + H]+ |
| 61 | 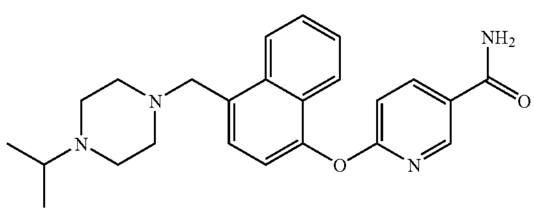 | 6-{4-[(3-Methylbutyl-amino)methyl]-naphthalen-1-yloxy}-nicotinonitrile hydrochloride | 2 | 2.84 | 346.2 [M + H]+ |
| 62 | 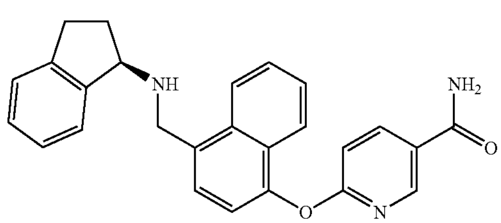 | 6-[4-((S)-Indan-1-yl-aminomethyl)-naphthalen-1-yloxy]-nicotinamide | 2 | 2.77 | 410.2 [M + H]+ |

TABLE 6-continued

| Ex | Structure | Name | X | RT (min) | m/z (ES+) |
|---|---|---|---|---|---|
| 63 | 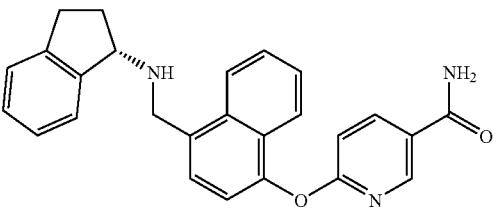 | 6-[4-((R)-Indan-1-yl-aminomethyl)-naphthalen-1-yloxy]-nicotinamide | 2 | 2.73 | 410.2 [M + H]+ |
| 64 | 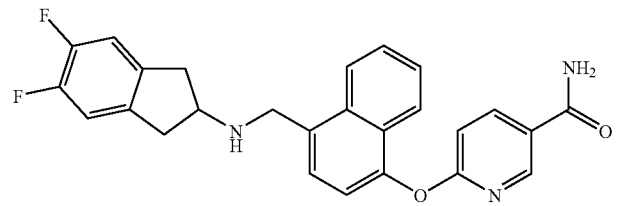 | 6-{4-[(5,6-Difluoro-indan-2-ylamino)-methyl]naphthalen-1-yloxy}nicotinamide | 2 | 2.73 | 446.2 [M + H]+ |
| 65 | 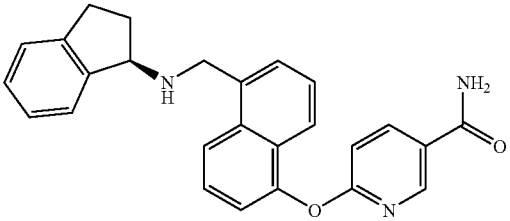 | 6-[5-((R)-Indan-1-yl-aminomethyl)-naphthalen-1-yloxy]-nicotinamide | 35 | 2.80 | 410.2 [M + H]+ |
| 66 | 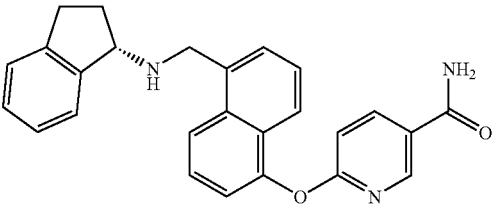 | 6-[5-((S)-Indan-1-yl-aminomethyl)-naphthalenyl)-1-yloxy]-nicotinamide | 35 | 2.65 | 410.2 [M + H]+ |
| 67 | 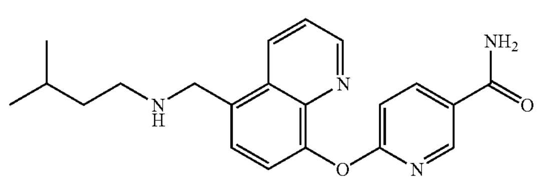 | 6-{5-[(3-Methyl-butylamino)methyl]-quinolin-8-yloxy}-nicotinamide | 67 | 2.24 | 365.3 [M + H]+ |
| 68 | 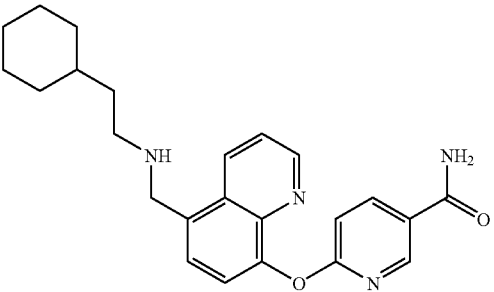 | 6-{5-[(2-Cyclohexyl-ethylamino)methyl]-quinolin-8-yloxy}-nicotinamide | 67 | 2.45 | 405.2 [M + H]+ |

TABLE 6-continued

| Ex | Structure | Name | X | RT (min) | m/z (ES+) |
|---|---|---|---|---|---|
| 69 | 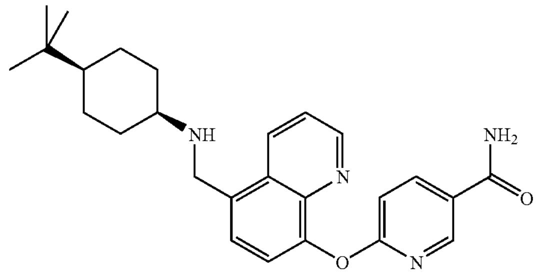 | 6-{5-[cis-(4-tert-Butyl-cyclohexylamino)-methyl]quinolin-8-yloxy]nicotinamide | 67 | 2.73 | 433.4 [M + H]+ |
| 70 | 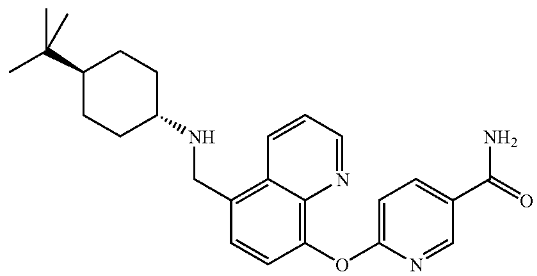 | 6-{5-[trans-(4-tert-Butylcyclohexyl-amino)methyl]-quinolin-8-yloxy}-nicotinamide | 67 | 2.68 | 433.4 [M + H]+ |
| 71 | 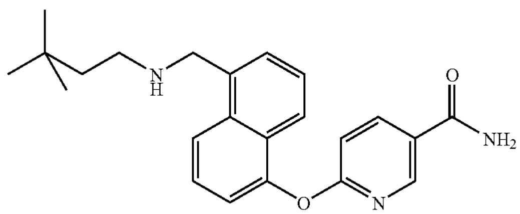 | 6-{5-[(3,3-Dimethyl-butylamino)methyl]-naphthalen-1-yloxy}-nicotinamide | 35 | 2.60 | 378.2 [M + H]+ |
| 72 | 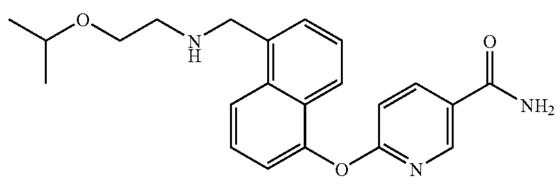 | 6-{5-[(2-Isopropoxy-ethylamino)methyl]-naphthalen-1-yloxy}-nicotinamide | 35 | 2.47 | 380.2 [M + H]+ |
| 73 | 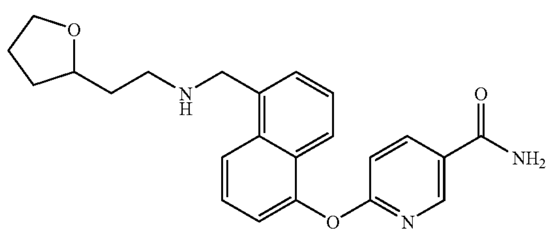 | 6-(5-{[2-(Tetrahydro-furan-2-yl)ethylamino]-methyl}naphthalen-1-yloxy)nicotinamide | 35 | 2.54 | 392.2 [M + H]+ |
| 74 | 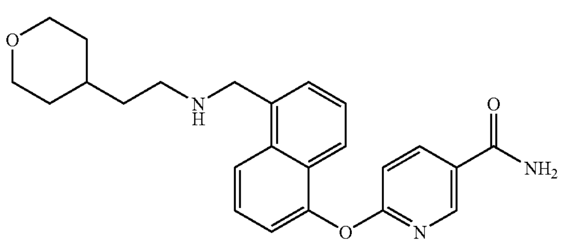 | 6-(5-{[2-(Tetrahydro-pyran-4-yl)ethyl-amino]methyl}-naphthalen-1-yloxy)-nicotinamide | 35 | 2.47 | 406.3 [M + H]+ |

TABLE 6-continued

| Ex | Name | X | RT (min) | m/z (ES+) |
|---|---|---|---|---|
| 75 | 6-{5-[((R)-2-Hydroxy-2-phenylethylamino)-methyl]naphthalen-1-yloxy}nicotinamide | 35 | 2.54 | 414.1 [M + H]+ |
| 76 | 6-(5-{[2-(Tetrahydro-pyran-2-yl)ethyl-amino]methyl}-naphthalen-1-yloxy)-nicotinamide | 35 | 2.55 | 406.2 [M + H]+ |
| 77 | 6-{5-[(1-Oxa-spiro-[4.4]non-3-ylamino)-methyl]naphthalen-1-yloxy}nicotinamide | 35 | 2.48 | 418.2 [M + H]+ |
| 78 | 6-{5-[((S)-2-Hydroxy-2-phenylethylamino)-methyl]naphthalen-1-yloxy}nicotinamide | 35 | 2.54 | 414.2 [M + H]+ |
| 79 | 6-{5-[(4,4-Dimethyl-cyclohexylamino)-methyl]naphthalen-1-yloxy}nicotinamide | 35 | 2.73 | 404.3 [M + H]+ |
| 80 | 3-Fluoro-4-(5-{[2-(tetrahydrofuran-4-yl)ethylamino]methyl}naphthalen-1-yloxy)benzamide | 38 | 2.59 | 423.2 [M + H]+ |

TABLE 6-continued

| Ex | Structure | Name | X | RT (min) | m/z (ES+) |
|---|---|---|---|---|---|
| 81 | 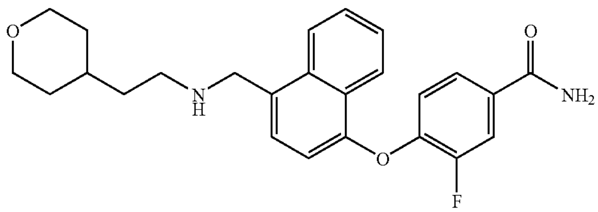 | 3-Fluoro-4-(4-{[2(tetrahydropyran-4-yl)ethylamino]methyl}-naphthalen-1-yloxy)-benzamide | 85 | 2.63 | 423.2 [M + H]+ |
| 82 | 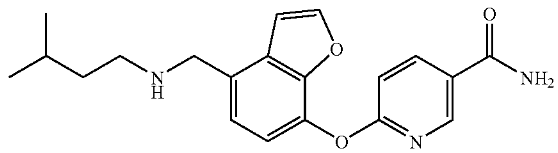 | 6-{4-[(3-Methyl-butylamino)methyl]-benzofuran-7-yloxy}-nicotinamide | 75 | 2.42 | 354.2 [M + H]+ |
| 83 | 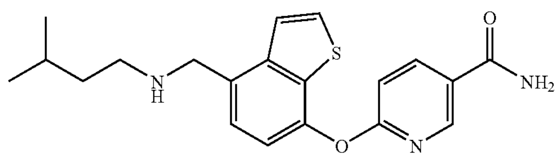 | 6-{4-[(3-Methyl-butylamino)methyl]-benzo[b]thiophen-7-yloxy}nicotinamide | 71 | 2.62 | 370.1 [M + H]+ |
| 84 | 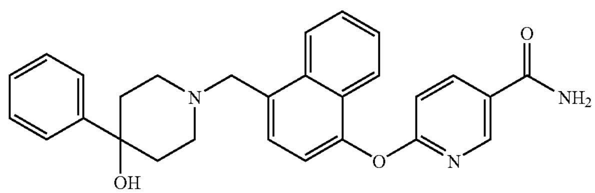 | 6-[4-(4-Hydroxy-4-phenylpiperidin-1-yl-methyl)naphthalen-1-yloxy]nicotinamide | 2 | 2.58 | 453.6 [M + H]+ |
| 85 | 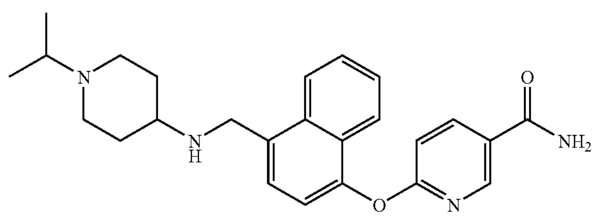 | 6-{4-[(1-Isopropyl-piperidin-4-ylamino)-methyl]naphthalen-1-yloxy}nicotinamide | 2 | 2.04 | 419.2 [M + H]+ |
| 86 | 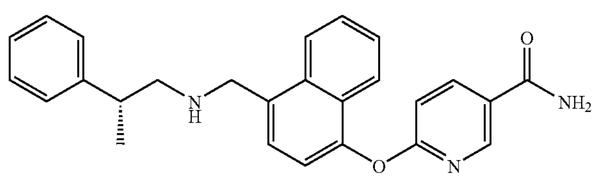 | 6-{4-[((R)-2-Phenyl-propylamino)methyl]-naphthalen-1-yloxy}-nicotinamide | 2 | 2.17** | 412.0 [M + H]+ |
| 87 | 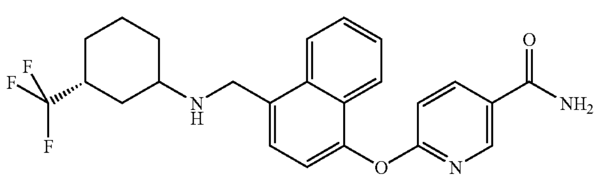 | 6-{4-[((R)-3-Trifluoro-methylcyclohexyl-amino)methyl]-naphthalen-1-yloxy}-nicotinamide | 2 | 2.12** | 443.9 [M + H]+ |
| 88 | 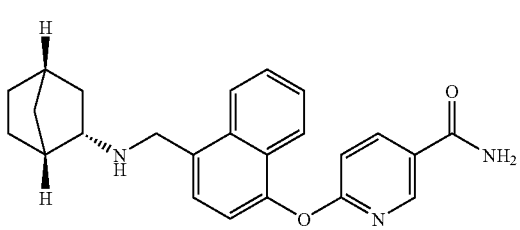 | 6-[4-((1R,2S,4S)-Bicyclo[2.2.1]hept-2-ylaminomethyl)-naphthalen-1-yloxy]-nicotinamide | 2 | 1.95** | 388.0 [M + H]+ |

TABLE 6-continued

| Ex | Structure | Name | X | RT (min) | m/z (ES+) |
|---|---|---|---|---|---|
| 89 | 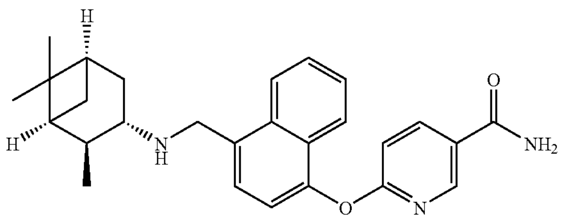 | 6-{4-[((1S,2S,3S,5R)-2,6,6-Trimethyl-bicyclo[3.1.1]hept-3-ylamino)methyl]-naphthalen-1-yloxy}-nicotinamide | 2 | 2.43** | 430.0 [M + H]+ |
| 90 | 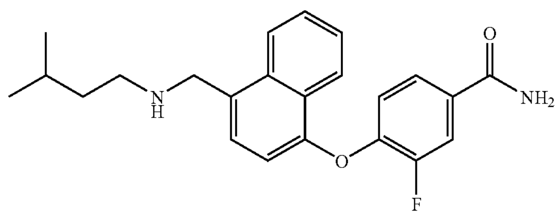 | 3-Fluoro-4-{4-[(3-methylbutylamino)-methyl]naphthalen-1-yloxy}benzamide | 85 | 2.62 | 381.2 [M + H]+ |

**LCMS Method 2

Example 91

6-{5-[3-Methylbutylamino)methyl]naphthalen-1-yloxy}nicotinamide

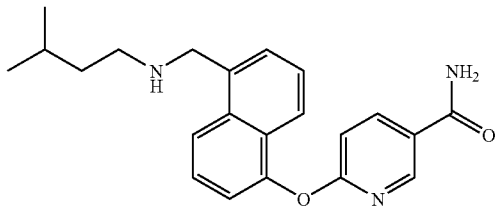

To a solution of 6-{5-[(3-methylbutylamino)methyl]naphthalen-1-yloxy}nicotinonitrile (Preparation 15) (60 mg, 0.17 mmol) in DMSO (1.5 mL) at rt under nitrogen, was added $K_2CO_3$ (12 mg, 0.09 mmol) and $H_2O_2$ (51 μL, 0.17 mmol). After 1.5 h water (3 mL) was added and the mixture partitioned between EtOAc (50 mL) and water (20 mL). The aqueous phase was extracted with EtOAc (2×50 mL) and the combined organic phase washed with water (20 mL), brine and dried ($MgSO_4$). Solvent was removed in vacuo and the residue purified by column chromatography (DCM:MeOH:$NH_4OH$, 95:5:0.5 to 92:8:0.8) to give the title compound: RT=2.55 min; m/z (ES+)=364.1 [M+H]+.

The procedure described in Example 91 was used to prepare Examples 92-95 from the appropriate nicotinonitrile (Preparation X in Table 7).

TABLE 7

| Ex | Structure | Name | X | RT (min) | m/z (ES+) |
|---|---|---|---|---|---|
| 92 | 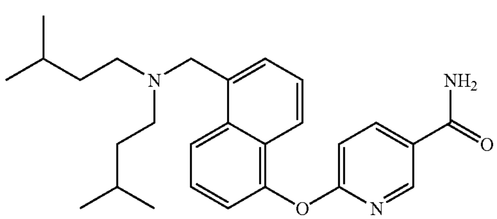 | 6-(5-{[Bis(3-methyl-butyl)amino]methyl}-naphthalen-1-yloxy)-nicotinamide hydrochloride | 48 | 2.82 | 434.4 [M + H]+ |
| 93 | 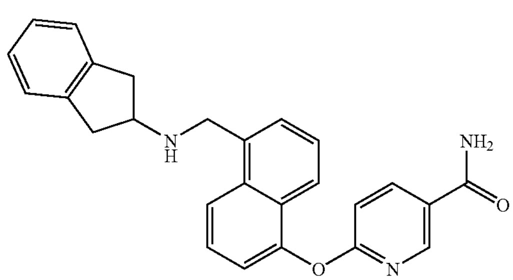 | 6-[5-(Indan-2-ylaminomethyl)-naphthalen-1-yloxy]-nicotinamide | 49 | 2.65 | 410.2 [M + H]+ |

| Ex | Structure | Name | X | RT (min) | m/z (ES+) |
|----|-----------|------|---|----------|-----------|
| 94 | 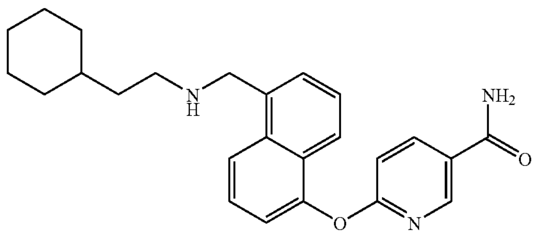 | 6-{5-[(2-Cyclohexyl-ethylamino)methyl]-naphthalen-1-yloxy}-nicotinamide | 50 | 2.88 | 404.2 [M + H]+ |
| 95 | 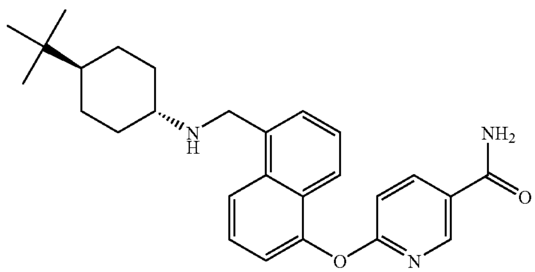 | 6-{5-[Trans-(4-tert-Butylcyclohexyl-amino)methyl]-naphthalen-1-yloxy}-nicotinamide | 51 | 3.00 | 432.3 [M + H]+ |

Example 96

4-{4-[(3-Methylbutylamino)methyl]isoquinolin-1-yloxy}benzamide

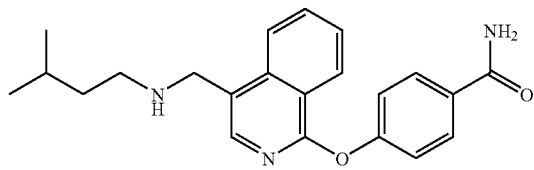

To a suspension of 4-(4-formylisoquinolin-1-yloxy)benzamide (Preparation 16) (100 mg, 0.34 mmol) in DMF (10 mL) was added 3-methylbutylamine (40 µL, 0.34 mmol) and 4 Å molecular sieves (200 mg). The mixture was stirred at rt for 72 h before adding NaBH$_4$ (65 mg, 1.7 mmol). After 16 h water (1 mL) was added. Solvent was removed in vacuo and the residue purified by column chromatography (NEt$_3$: MeOH: DCM 3:30:500) to give the title compound: RT=2.47 min; m/z (ES+)=364.0 [M+H]+.

Example 97

4-{4-[(2-Cyclohexylethylamino)methyl]isoquinolin-1-yloxy}benzamide

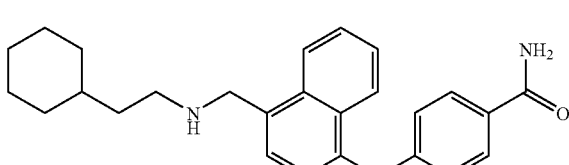

Using the procedure outlined in Example 96, 4-(4-formyl-isoquinolin-1-yloxy)-benzamide (Preparation 16) and 2-cyclohexylethylamine hydrochloride were converted to the title compound: RT=2.70 min; m/z (ES+)=404.0 [M+H]+.

Example 98

4-(4-{[2-(Tetrahydropyran-4-yl)ethylamino]methyl-isoquinolin-1-yloxy)benzamide

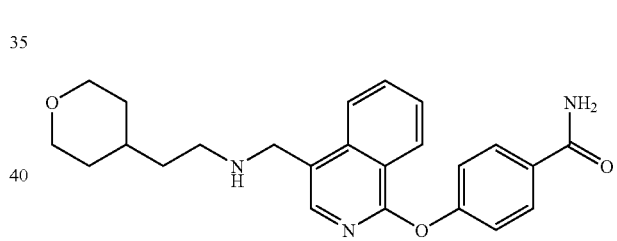

Using the procedure outlined in Example 96, 4-(4-formyl-isoquinolin-1-yloxy)benzamide (Preparation 16) and 2-(tetrahydropyran-4-yl)ethylamine were converted to the title compound: RT=2.23 min; m/z (ES+)=378.2 [M+H]+.

Example 99

6-{1-[(3-Methylbutylamino)methyl]isoquinolin-4-yloxy}nicotinamide

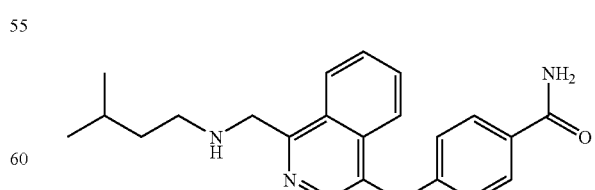

To 6-(1-formylisoquinolin-4-yloxy)nicotinamide (Preparation 20) (130 mg, 0.44 mmol) in dichloroethane (8 mL) was added 3-methylbutylamine (154 µL, 1.33 mmol), NaBH(OAc)$_3$ (282 mg, 1.33 mmol) and acetic acid (76 µL, 1.33 mmol). The mixture was stirred for 16 h. NaHCO₃ (50 mL) was added and the mixture extracted with EtOAc (3×40 mL). The organic phase was washed with water (30 mL), brine (30 mL) and dried (MgSO₄). Solvent was removed in vacuo and the residue purified by column chromatography (0.5 NH₃: 5 MeOH: 95 DCM) to give the title compound: RT=2.48 min; m/z (ES⁺)=365.2 [M+H]⁺.

Example 100

6-{1-[(trans-4-Isopropylcyclohexylamino)methyl]isoquinolin-4-yloxy}nicotinamide

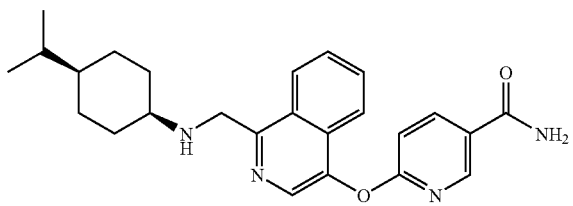

To a suspension of 6-(1-formylisoquinolin-4-yloxy)nicotinamide (Preparation 20) (150 mg, 0.51 mmol) and trans-4-isopropylcyclohexylamine hydrochloride (Preparation 9) (273 mg, 1.53 mmol) in 1,2-dichloroethane (10 mL) under argon was added acetic acid (30 µL, 0.51 mmol) followed by NaBH(OAc)₃ (325 mg, 1.53 mmol). The mixture was stirred at rt for 16 h then the reaction solvent was removed in vacuo. The residue was partitioned between EtOAc (50 mL) and NaHCO₃ (30 mL), and the organic phase washed with NaHCO₃ (30 mL), brine (30 mL) and dried (MgSO₄). Solvent was removed in vacuo and the residue purified by column chromatography (SiO₂, NH₄OH:MeOH:DCM 0.5:5:95) to give the title compound: RT=2.85 min; m/z (ES⁺)=419.3 [M+H]⁺.

The procedure described in Example 100 was used to prepare Examples 101 and 102 in Table 8 using 6-(1-formylisoquinolin-4-yloxy)nicotinamide (Preparation 20) and the appropriate amine hydrochloride:

Example 103

6-(5-{[(2,2-Dimethylcyclopropylmethyl)amino]methyl}naphthalene-1-yloxy)nicotinamide

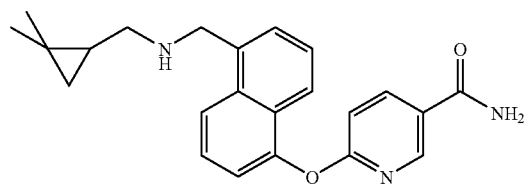

To a solution of 6-(5-formylnaphthalen-1-yloxy)nicotinamide (Preparation 35) (200 mg, 0.68 mmol) and (2,2-dimethylcyclopropyl)methylamine hydrochloride (111 mg, 0.82 mmol) in a 1:1 mixture of MeOH/DCM (12 mL) was added PS-diisopropylethylamine (3.66 mmol/g, 374 mg, 1.37 mmol) and the reaction was stirred at rt for 16 h. PS-borohydride (2 mmol/g, 1.03 g, 2.05 mmol) was added and the reaction was stirred for 30 min Water (0.5 mL) was added and the mixture purified through an SCX column (10 g/70 mL) eluting with 1% NH₄OH in MeOH. Solvent was removed in vacuo and the residue was triturated with EtOAc to give the title compound: RT=2.60 min; m/z (ES⁺)=376.2 [M+H]⁺.

Example 104

3-Fluoro-4-[1-(indan-2-ylaminomethyl)isoquinolin-4-yloxy]benzamide

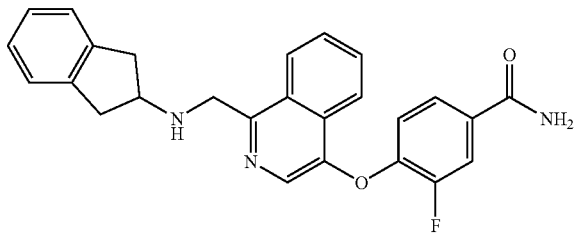

TABLE 8

| Ex | Structure | Name | RT (min) | m/z (ES⁺) |
|---|---|---|---|---|
| 101 | 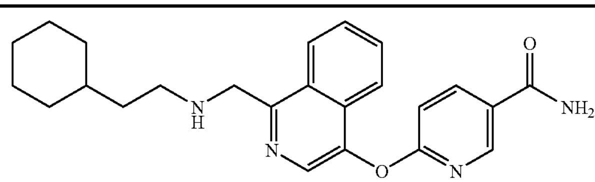 | 6-{1-[(2-Cyclohexylethylamino)methyl]-isoquinolin-4-yloxy}-nicotinamide | 2.76 | 405.3 [M + H]⁺ |
| 102 | 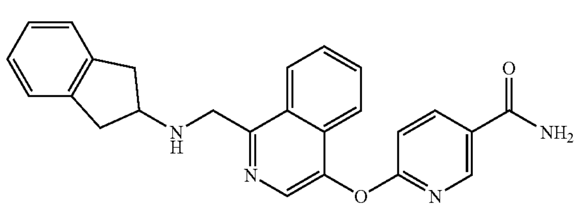 | 6-[1-(Indan-2-ylaminomethyl)-isoquinolin-4-yloxy]-nicotinamide | 2.38 | 406.2 [M + H]⁺ |

Using the procedure outlined in Example 100, 3-fluoro-4-(1-formylisoquinolin-4-yloxy)benzamide (Preparation 42) and indan-2-ylamine hydrochloride were converted to the title compound: RT=2.87 min; m/z (ES+)=428.1 [M+H]+.

Example 105

6-{4-[(2-Piperidin-1-yl-ethylamino)methyl]naphthalen-1-yloxy}nicotinamide hydrochloride

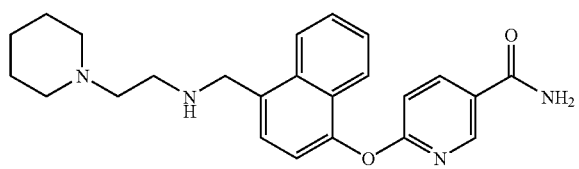

To a solution of 6-(4-formylnaphthalen-1-yloxy)nicotinamide (Preparation 2) (70 mg, 0.24 mmol) and 2-piperidin-1-ylethylamine (37 µL, 0.26 mmol) in MeOH (5 mL) was added 4 Å molecular sieves (50 mg) and the reaction stirred for 16 h at rt. NaBH$_4$ (45 mg, 1.2 mmol) was added and the mixture stirred for a further 1 h. Water (0.5 mL) was added, the reaction mixture filtered and the solvent removed in vacuo. The residue was purified by column chromatography (SiO$_2$, NH$_4$OH:MeOH:DCM 0.5:5:95) to give the title compound as a free base. 4M HCl in dioxane and Et$_2$O were added to the residue, and the resulting precipitate was filtered to give the title compound: RT=1.96 min; m/z (ES+)=405.3 [M+H]+.

The procedure outlined in Example 105 was used to prepare Examples 106-109 in Table 9 from 6-(4-formylnaphthalen-1-yloxy)nicotinamide (Preparation 2) and the appropriate amine:

TABLE 9

| Ex | Structure | Name | RT (min) | m/z (ES+) |
|---|---|---|---|---|
| 106 | 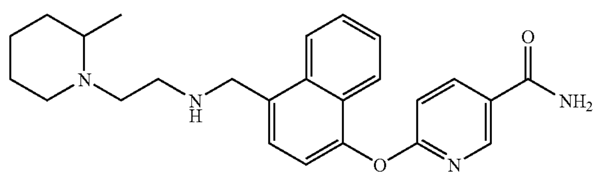 | 6-(4-{[(2-(2-Methyl-piperidin-1-yl)-ethylamino]methyl}-naphthalen-1-yloxy)-nicotinamide | 2.47 | 459.4 [M + MeCN]+ |
| 107 | 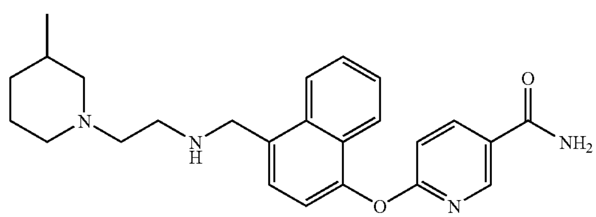 | 6-(4-{[2-(3-Methyl-piperidin-1-yl)-ethylamino]methyl}-naphthalen-1-yloxy)-nicotinamide | 1.99 | 419.3 [M + H]+ |
| 108 | 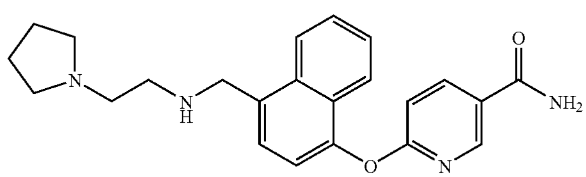 | 6-{4-[(2-Pyrrolidin-1-ylethylamino)methyl]-naphthalen-1-yloxy}-nicotinamide | 2.02 | 391.3 [M + H]+ |
| 109 | 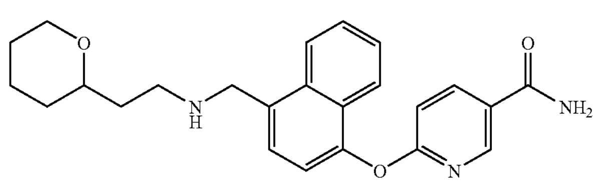 | 6-(4-{[2-(Tetrahydro-pyran-2-yl)-ethyl-amino]methyl}-naphthalen-1-yloxy)-nicotinamide | 2.53 | 406.2 [M + H]+ |

Example 110

6-{5-[(4,4-Difluorocyclohexylamino)methyl]naphthalen-1-yloxy}-nicotinamide

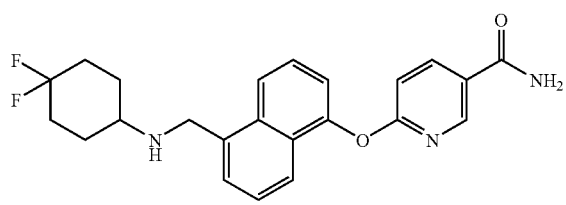

To a solution of 6-(5-formylnaphthalen-1-yloxy)nicotinamide (Preparation 35) (200 mg, 0.7 mmol) in MeOH (10 mL) was added 4,4-difluorocyclohexylammonium chloride (141 mg, 0.8 mmol), DIPEA (358 µl, 2.1 mmol) and 4 Å molecular sieves (200 mg). The mixture was stirred at 50° C. for 16 h, cooled to rt and NaBH$_4$ (78 mg, 2.1 mmol) added. After 3 h water (1 mL) was added and the mixture filtered. Solvent was removed in vacuo and the residue purified by column chromatography (10% MeOH-EtOAc) to give the title compound: RT=2.40 min; m/z (ES$^+$)=412.2 [M+H]$^+$.

The procedure outlined in Example 110 was used to prepare Examples 111-133 in Table 10 from the corresponding nicotinamides (Preparation X in Table 10) and the appropriate ammonium chloride. Hydrochloride salts, where formed, were prepared by adding a few drops of 1M HCl to the free base followed by removal of the solvent in vacuo. The mixture was washed with acetone (10 mL) and the solid removed by filtration to give the title compound:

TABLE 10

| Ex | Structure | Name | X | RT (min) | m/z (ES$^+$) |
|---|---|---|---|---|---|
| 111 | 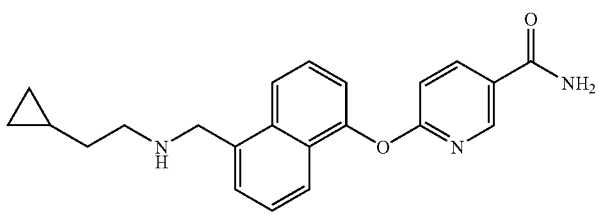 | 6-{5-[(2-Cyclopropylethylamino)methyl]-naphthalen-1-yloxy}-nicotinamide | 35 | 2.38 | 362.2 [M + H]$^+$ |
| 112 | 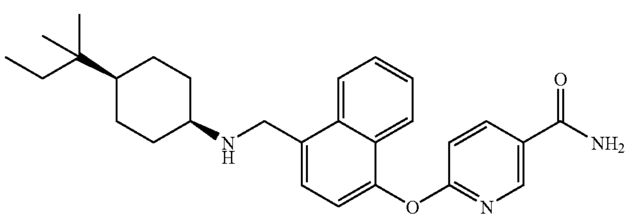 | 6-(5-{[cis-4-(1,1-Dimethylpropyl)-cyclohexylamino]-methyl}naphthalen-1-yloxy)nicotinamide | 35 | 3.00 | 446.3 [M + H]$^+$ |
| 113 | 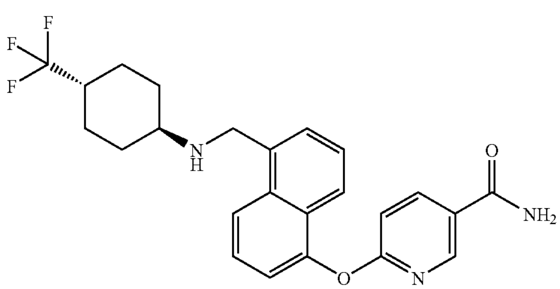 | 6-{4-[(4-Trifluoromethylcyclohexyl-amino)methyl]-naphthalen-1-yloxy}-nicotinamide | 2 | 2.70 | 444.2 [M + H]$^+$ |
| 114 | 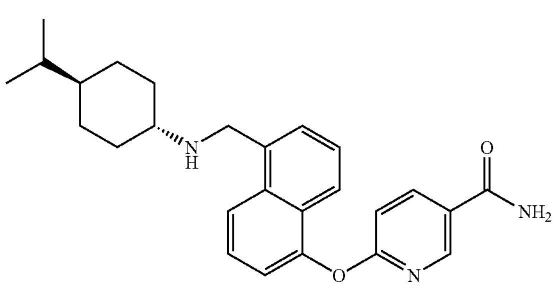 | 6-{5-[trans-(4-Isopropylcyclohexyl-amino)methyl]-naphthalen-1-yloxy}-nicotinamide | 35 | 2.85 | 418.2 [M + H]$^+$ |

TABLE 10-continued

| Ex | Structure | Name | X | RT (min) | m/z (ES+) |
|---|---|---|---|---|---|
| 115 | 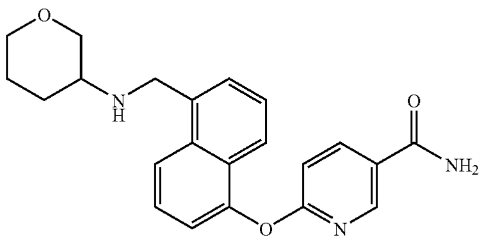 | 6-{5-[(Tetrahydro-pyran-3-ylamino)-methyl]naphthalen-1-yloxy}nicotinamide | 35 | 2.29 | 378.2 [M + H]+ |
| 116 | 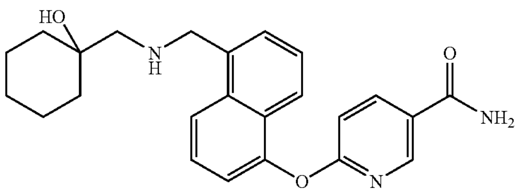 | 6-(5-{[(1-Hydroxy-cyclohexylmethyl)-amino]methyl}-naphthalen-1-yloxy)-nicotinamide | 35 | 2.61 | 410.2 [M + H]+ |
| 117 | 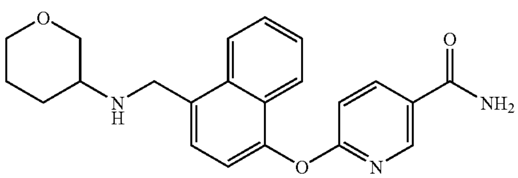 | 6-{4-[(Tetrahydro-pyran-3-ylamino)-methyl]naphthalen-1-yloxy}nicotinamide | 2 | 2.25 | 378.2 [M + H]+ |
| 118 | 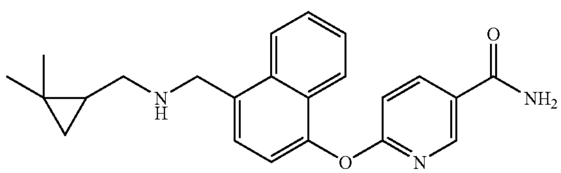 | 6-(4-{[(2,2-Dimethyl-cyclopropylmethyl)-amino]methyl}-naphthalen-1-yloxy)-nicotinamide | 2 | 2.53 | 376.2 [M + H]+ |
| 119 | 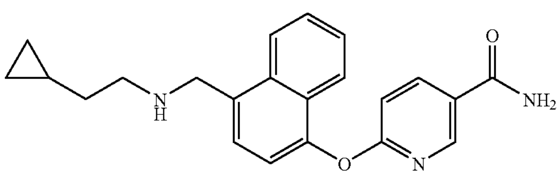 | 6-{4-[(2-Cyclopropyl-ethylamino)methyl]-naphthalen-1-yloxy}-nicotinamide | 2 | 2.49 | 362.2 [M + H]+ |
| 120 | 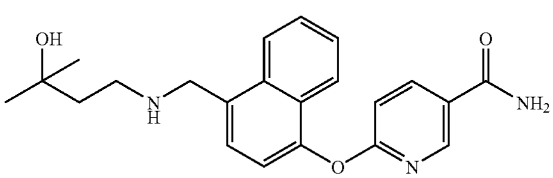 | 6-{4-[(3-Hydroxy-3-methylbutylamino)-methyl]naphthalen-1-yloxy}nicotinamide | 2 | 2.27 | 380.2 [M + H]+ |
| 121 | 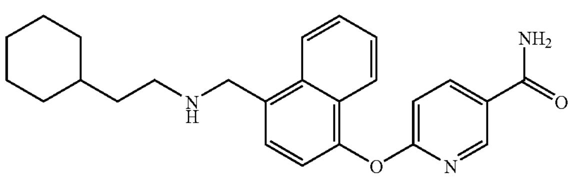 | 6-{4-[(2-Cyclohexyl-ethylamino)methyl]-naphthalen-1-yloxy}-nicotinamide | 2 | 2.86 | 404.0 [M + H]+ |
| 122 | 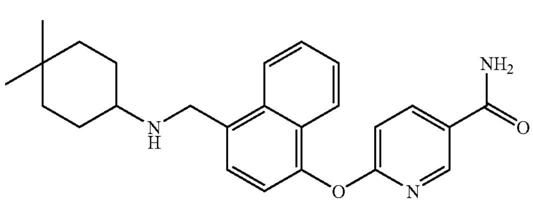 | 6-{4-[(4,4-Dimethyl-cyclohexylamino)-methyl]naphthalen-1-yloxy}nicotinamide | 2 | 2.79 | 404.0 [M + H]+ |

TABLE 10-continued

| Ex | Structure | Name | X | RT (min) | m/z (ES+) |
|---|---|---|---|---|---|
| 123 | 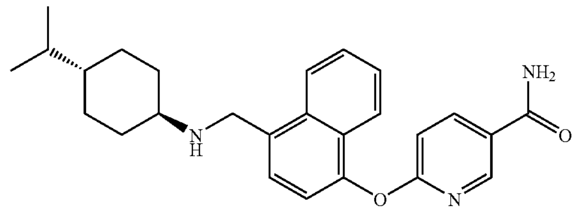 | 6-{4-[trans-(4-Isopropylcyclohexyl-amino)methyl]-naphthalen-1-yloxy}-nicotinamide | 2 | 2.99 | 418.1 [M + H]+ |
| 124 | 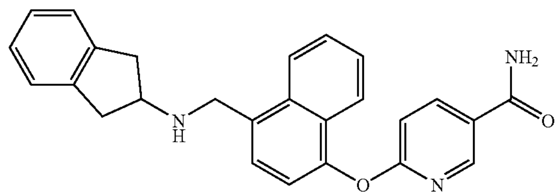 | 6-[4-(Indan-2-yl-aminomethyl)-naphthalen-1-yloxy]-nicotinamide | 2 | 2.61 | 410.2 [M + H]+ |
| 125 | 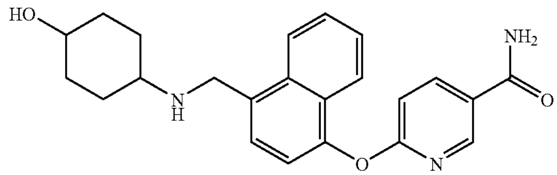 | 6-{4-[(4-Hydroxy-cyclohexylamino)-methyl]naphthalen-1-yloxy}nicotinamide | 2 | 2.24 | 392.2 [M + H]+ |
| 126 | 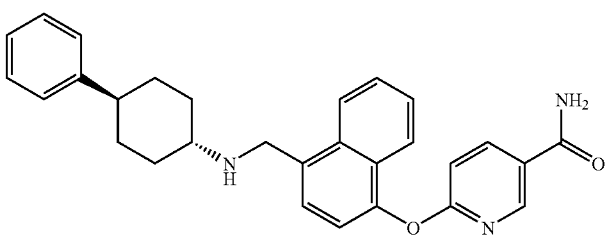 | 6-{4-[trans(4-Phenyl-cyclohexylamino)-methyl]naphthalen-1-yloxy}nicotinamide | 2 | 2.93 | 452.3 [M + H]+ |
| 127 | 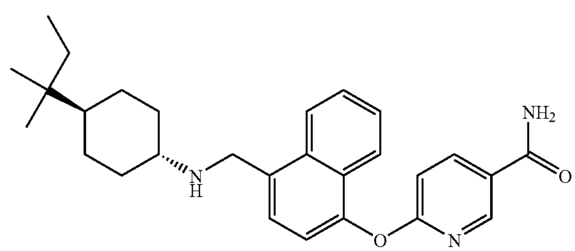 | 6-(4-{[trans-4-(1,1-Dimethylpropyl)cyclo-hexylamino]methyl}-naphthalen-1-yloxy)-nicotinamide hydrochloride | 2 | 3.09 | 446.3 [M + H]+ |
| 128 | 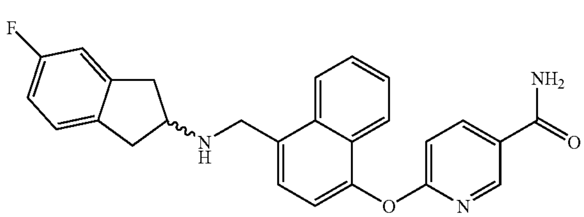 | 6-{5-[(5-Fluoroindan-2-ylamino)methyl]-naphthalen-1-yloxy}-nicotinamide | 2 | 2.68 | 428.2 [M + H]+ |
| 129 | 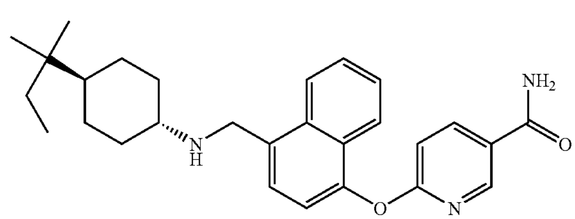 | 6-(5-{trans[4-(1,1-Dimethylpropyl)cyclo-hexylamino]methyl}-naphthalen-1-yloxy)-nicotinamide hydrochloride | 35 | 3.07 | 446.3 [M + H]+ |

TABLE 10-continued

| Ex | Structure | Name | X | RT (min) | m/z (ES⁺) |
|---|---|---|---|---|---|
| 130 | 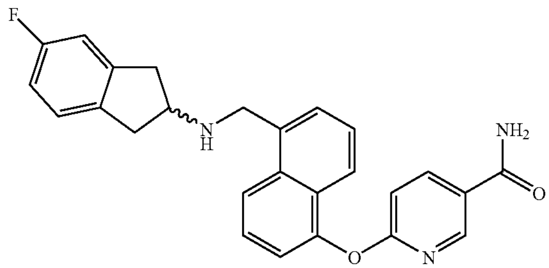 | 6-{5-[(5-Fluoroindan-2-ylamino)methyl]-naphthalen-1-yloxy}-nicotinamide | 35 | 2.70 | 428.2 [M + H]⁺ |
| 131 | 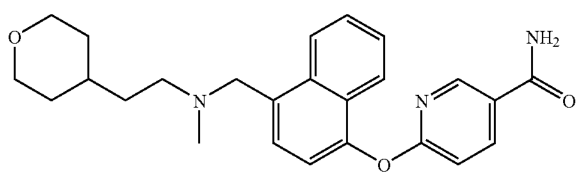 | 6-[4-({Methyl-[2-(tetrahydropyran-4-yl)ethyl]amino}methyl)naphthalen-1-yloxy]-nicotinamide | 2 | 2.45 | 420.4 [M + H]⁺ |
| 132 | 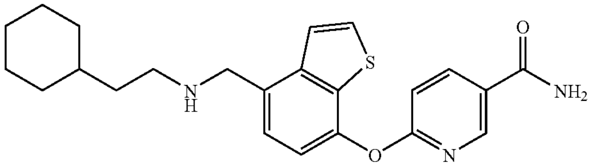 | 6-{4-[(2-Cyclohexyl-ethylamino)methyl]-benzo[b]thiophen-7-yloxy}nicotinamide | 71 | 2.88 | 410.5 [M + H]⁺ |
| 133 | 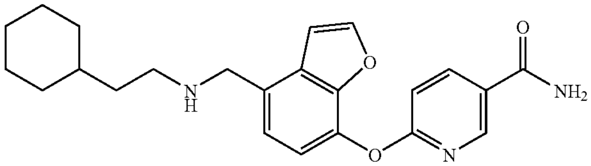 | 6-{4-[(2-Cyclohexyl-ethylamino)methyl]-benzofuran-7-yloxy}-nicotinamide | 75 | 2.60 | 394.5 [M + H]⁺ |

Example 134

3-Chloro-4-{4-[(3-methylbutylamino)methyl]naphthalen-1-yloxy}benzamide

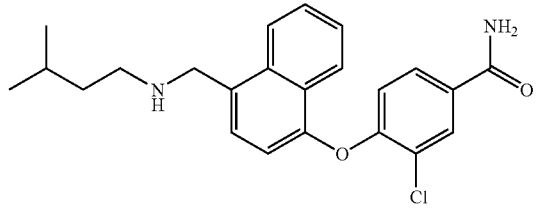

Using the procedure outlined in Preparation 19, 3-chloro-4-{4-[(3-methylbutylamino)methyl]naphthalen-1-yloxy}benzonitrile (Preparation 83) was converted to the title compound: RT=2.80 min; m/z (ES⁺)=397.2, 399.2 [M+H]⁺.

Example 135

4-{4-[(3-Methylbutylamino)methyl]naphthalen-1-yloxy}benzamide

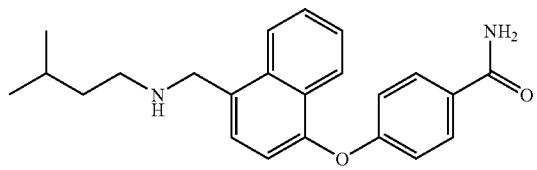

Using the procedure outlined in Preparation 19, 4-{4-[(3-methylbutylamino)-methyl]naphthalen-1-yloxy}benzonitrile (Preparation 87) was converted to the title compound: RT=2.73 min; m/z (ES⁺)=363.2 [M+H]⁺.

Example 137

4-{8-[(3-Methylbutylamino)methyl]quinolin-4-yloxy}benzamide

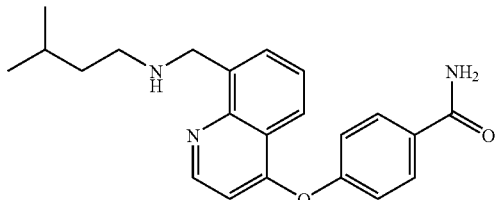

To a solution of 4-(8-aminomethylquinolin-4-yloxy)benzamide (23 mg, 0.08 mmol, Preparation 90) in MeOH (5 mL) was added 3-methylbutyraldehyde (8.5 µL, 0.08 mmol) and 4 Å molecular sieves (500 mg). The resulting mixture was heated to 50° C. for 16 h then cooled to rt and NaBH₄ (6 mg, 0.16 mmol) was added. After 3 h a few drops of water were added, the mixture filtered and washed with MeOH. Solvent was removed in vacuo and the residue purified by column chromatography (0.25% NH₄OH$_{(aq)}$, 5% MeOH in DCM) to give the title compound: RT=2.65 min; m/z (ES⁺)=364.2 [M+H]⁺.

Example 138

6-{4-[(3-Methylbutylamino)methyl]naphthalene-1-yloxy}pyridine-2-carboxamide hydrochloride

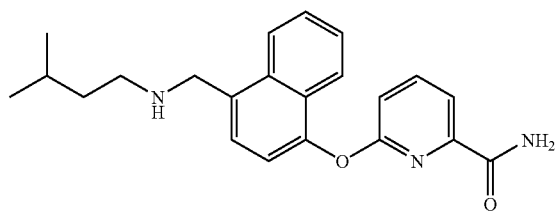

To a solution of 4-[(3-methylbutylamino)methyl]naphthalen-1-ol (Preparation 28) (191 mg, 0.79 mmol) and 2-fluoro-6-pyridine carboxamide (100 mg, 0.71 mmol) in DMSO (6 mL) under argon was added cesium carbonate (698 mg, 2.14 mmol) and the reaction was heated to 90° C. for 4 h. The mixture was partitioned between water (100 mL) and EtOAc:THF 1:1 (3×50 mL). The combined organic phase was and washed with water (40 mL), NaHCO$_3$ (40 mL), brine (40 mL) and then dried (MgSO$_4$). Solvent was removed in vacuo and the residue purified by prep HPLC to give the product as the TFA salt. Na$_2$CO$_3$ (10 mL) and EtOAc (10 mL) were added and the organic layer was separated, dried (MgSO$_4$) and solvent removed in vacuo. The residue was dissolved in MeOH (3 mL) and acidified with 4M HCl in dioxane. Solvent was removed in vacuo to give the title compound: RT=2.62 min; m/z (ES$^+$)=364.2 [M+H]$^+$.

Example 139

2-{4-[(3-Methylbutylamino)methyl]naphthalen-1-yloxy}isonicotinamide

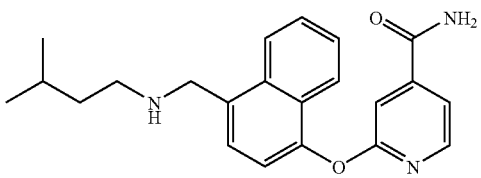

Using the procedure outlined in Example 1,2-(4-formyl-naphthalen-1-yloxy)-isonicotinamide (Preparation 91) and 3-methylbutylamine were converted to the title compound: RT=2.46 min; m/z (ES$^+$)=364.2 [M+H]$^+$.

Using the procedure outlined below, Examples 140-173 (Table 11) were synthesised from the corresponding nicotinamide (Preparation X in Table 11) and amine:

To a solution of the aldehyde (0.51 mmol) in THF (5 mL) was added amine (0.49 mmol), acetic acid (0.55 mmol) (sodium acetate (0.51 mmol) is added if amine HCl salt is used). The mixture was stirred for 0.5 h and then NaBH(OAc)$_3$ (1.23 mmol) was added. After 16 h water (10 mL) and EtOAc (40 mL) were added and the pH of the mixture adjusted to ~pH 11 with 2M NaOH. The mixture was extracted with EtOAc (2×40 mL) and the combined organics were washed with water (20 mL), brine (20 mL) and then dried (MgSO$_4$). The solvent was removed in vacuo and the residue purified by column chromatography (1% MeOH:EtOAc) to give the title compound.

TABLE 11

| Ex | Structure | Name | X | RT (min) | m/z (ES$^+$) |
|---|---|---|---|---|---|
| 140 | ![structure] | 6-[5-(4,4-Difluoro-piperidin-1-ylmethyl)-naphthalen-1-yloxy]-nicotinamide | 35 | 2.16** | 398.3 [M + H]$^+$ |
| 141 | ![structure] | 6-[5-(3-Methyl-azetidin-1-ylmethyl)-naphthalen-1-yloxy]-nicotinamide | 35 | 2.03** | 348.2 [M + H]$^+$ |
| 142 | ![structure] | 6-[5-(4-Trifluoro-methylpiperidin-1-ylmethyl)naphthalen-1-yloxy]nicotinamide | 35 | 2.26** | 430.1 [M + H]$^+$ |

TABLE 11-continued

| Ex | Structure | Name | X | RT (min) | m/z (ES+) |
|---|---|---|---|---|---|
| 143 | 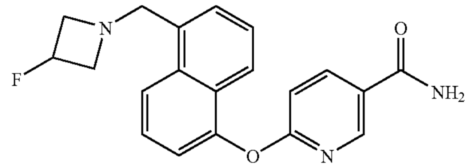 | 6-[5-(3-Fluoro-azetidin-1-ylmethyl)-naphthalen-1-yloxy]-nicotinamide | 35 | 1.97** | 352.1 [M + H]+ |
| 144 | 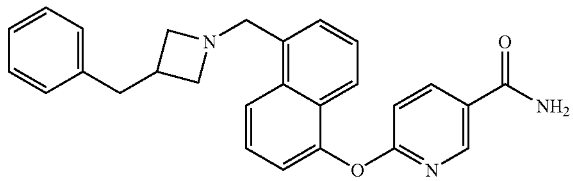 | 6-[5-(3-Benzyl-azetidin-1-ylmethyl)-naphthalen-1-yloxy]-nicotinamide | 35 | 2.56** | 424.1 [M + H]+ |
| 145 | 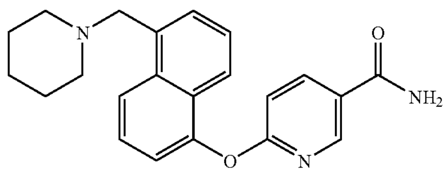 | 6-(5-Piperidin-1-ylmethylnaphthalen-1-yloxy)nicotinamide | 35 | 2.06** | 362.3 [M + H]+ |
| 146 | 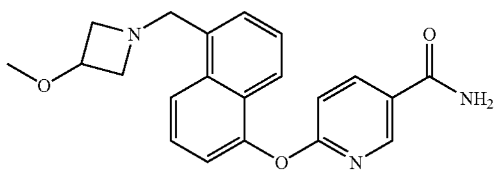 | 6-[5-(3-Methoxy-azetidin-1-ylmethyl)-naphthalen-1-yloxy]-nicotinamide | 35 | 1.99** | 364.4 [M + H]+ |
| 147 | 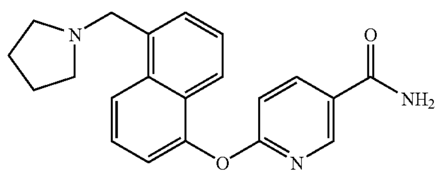 | 6-(5-Pyrrolidin-1-ylmethylnaphthalen-1-yloxy)nicotinamide | 35 | 2.00* | 384.2 [M + H]+ |
| 148 | 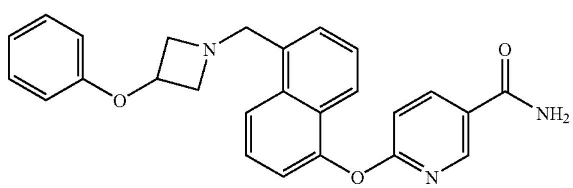 | 6-[5-(3-Phenoxy-azetidin-1-ylmethyl)-naphthalen-1-yloxy]-nicotinamide | 35 | 2.46** | 426.2 [M + H]+ |
| 149 | 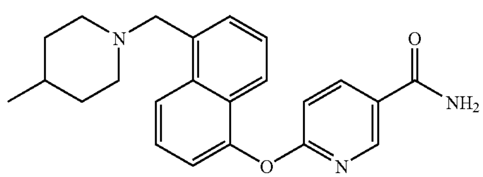 | 6-[5-(4-Methyl-piperidin-1-ylmethyl)-naphthalen-1-yloxy]-nicotinamide | 35 | 2.20** | 376.4 [M + H]+ |
| 150 | 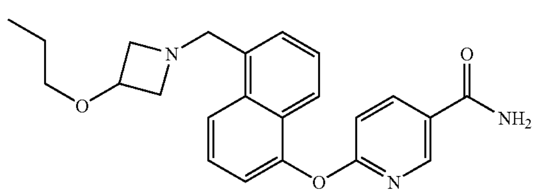 | 6-[5-(3-Propoxy-azetidin-1-ylmethyl)-naphthalen-1-yloxy]-nicotinamide | 35 | 2.30** | 392.3 [M + H]+ |

TABLE 11-continued

| Ex | Structure | Name | X | RT (min) | m/z (ES+) |
|---|---|---|---|---|---|
| 151 | 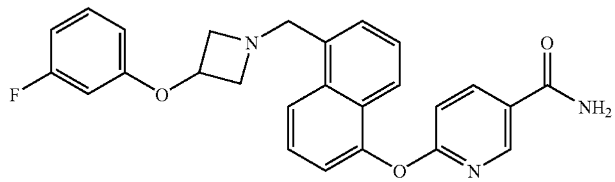 | 6-{5-[3-(3-Fluoro-phenoxy)azetidin-1-ylmethyl]naphthalen-1-yloxy}nicotinamide | 35 | 2.51** | 444.2 [M + H]+ |
| 152 | 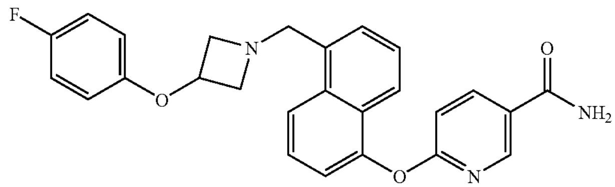 | 6-{5-[3-(4-Fluoro-phenoxy)azetidin-1-ylmethyl]naphthalen-1-yloxy}nicotinamide | 35 | 2.51** | 444.2 [M + H]+ |
| 153 | 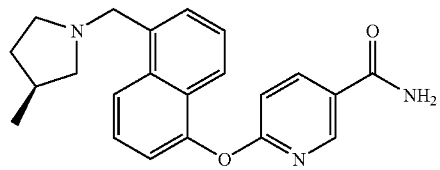 | 6-[5-((S)-3-Methyl-pyrrolidin-1-ylmethyl)-naphthalen-1-yloxy]-nicotinamide | 35 | 2.12** | 362.3 [M + H]+ |
| 154 | 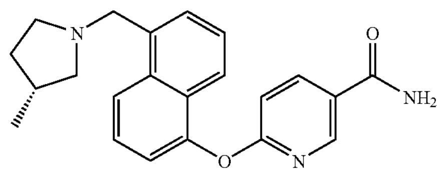 | 6-[5-((R)-3-Methyl-pyrrolidin-1-ylmethyl)-naphthalen-1-yloxy]-nicotinamide | 35 | 2.07** | 362.3 [M + H]+ |
| 155 | 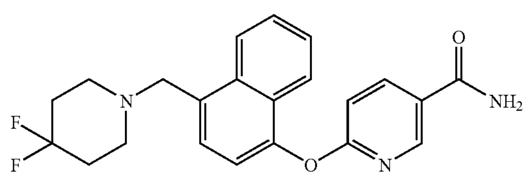 | 6-[4-(4,4-Difluoro-piperidin-1-ylmethyl)-naphthalen-1-yloxy]-nicotinamide | 2 | 2.18** | 398.3 [M + H]+ |
| 156 | 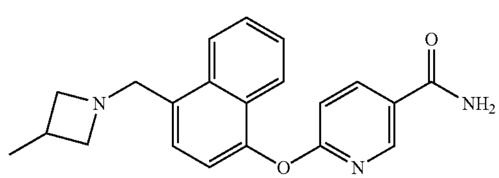 | 6-[4-(3-Methyl-azetidin-1-ylmethyl)-naphthalen-1-yloxy]-nicotinamide | 2 | 2.07** | 348.2 [M + H]+ |
| 157 | 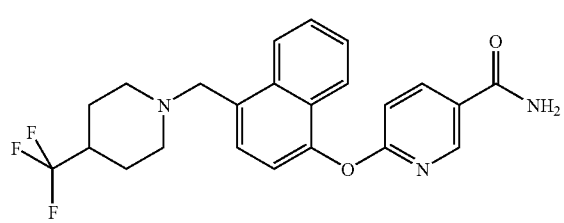 | 6-[4-(4-Trifluoro-methylpiperidin-1-ylmethyl)naphthalen-1-yloxy]nicotinamide | 2 | 2.29** | 430.1 [M + H]+ |
| 158 | 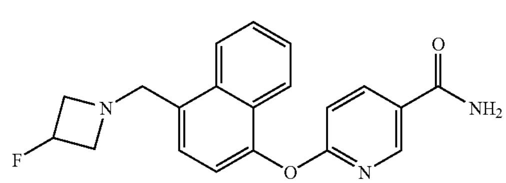 | 6-[4-(3-Fluoro-azetidin-1-ylmethyl)-naphthalen-1-yloxy]-nicotinamide | 2 | 1.99* | 352.1 [M + H]+ |

TABLE 11-continued

| Ex | Structure | Name | X | RT (min) | m/z (ES+) |
|---|---|---|---|---|---|
| 159 | 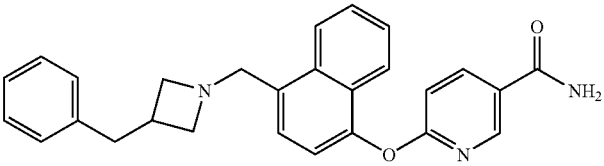 | 6-[4-(3-Benzyl-azetidin-1-ylmethyl)-naphthalen-1-yloxy]-nicotinamide | 2 | 2.51** | 424.1 [M + H]+ |
| 160 | 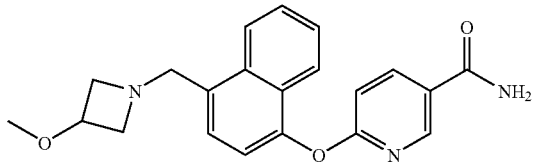 | 6-[4-(3-Methoxy-azetidin-1-ylmethyl)-naphthalen-1-yloxy]-nicotinamide | 2 | 2.03** | 364.1 [M + H]+ |
| 161 | 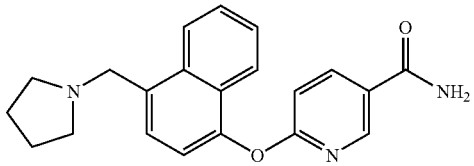 | 6-(4-Pyrrolidin-1-ylmethylnaphthalen-1-yloxy)nicotinamide | 2 | 2.02** | 348.2 [M + H]+ |
| 162 | 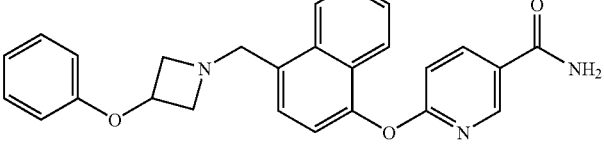 | 6-[4-(3-Phenoxy-azetidin-1-ylmethyl)-naphthalen-1-yloxy]-nicotinamide | 2 | 2.47** | 426.2 [M + H]+ |
| 163 | 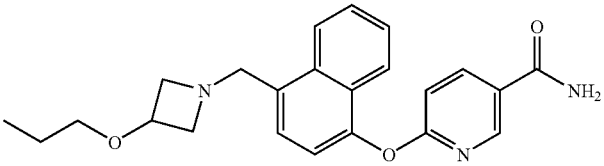 | 6-[4-(3-Propoxy-azetidin-1-ylmethyl)-naphthalen-1-yloxy]-nicotinamide | 2 | 2.30** | 392.3 [M + H]+ |
| 164 | 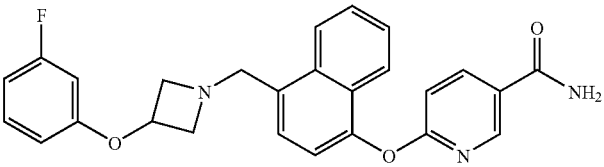 | 6-{4-[3-(3-Fluoro-phenoxy)azetidin-1-ylmethyl]-naphthalen-1-yloxy}-nicotinamide | 2 | 2.53** | 444.2 [M + H]+ |
| 165 | 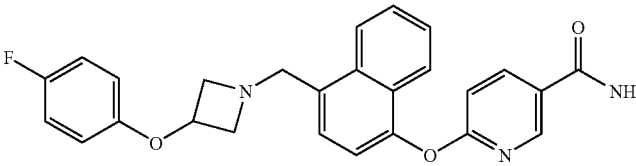 | 6-{4-[3-(4-Fluoro-phenoxy)azetidin-1-ylmethyl]-naphthalen-1-yloxy}-nicotinamide | 2 | 2.52** | 444.2 [M + H]+ |
| 166 | 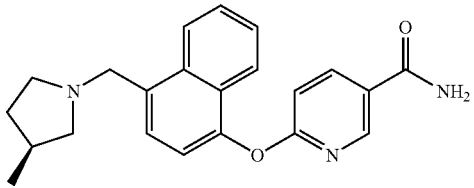 | 6-[4-((S)-3-Methyl-pyrrolidin-1-ylmethyl)-naphthalen-1-yloxy]-nicotinamide | 2 | 2.13** | 362.3 [M + H]+ |

TABLE 11-continued

| Ex | Structure | Name | X | RT (min) | m/z (ES+) |
|---|---|---|---|---|---|
| 167 | 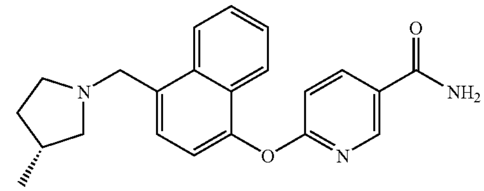 | 6-[4-((R)-3-Methyl-pyrrolidin-1-ylmethyl)-naphthalen-1-yloxy]-nicotinamide | 2 | 2.13** | 362.3 [M + H]+ |
| 168 | 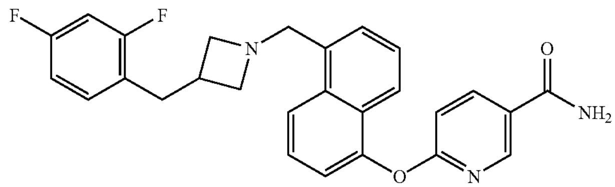 | 6-{5-[3-(2,4-Difluoro-benzyl)azetidin-1-ylmethyl]naphthalen-1-yloxy}nicotinamide | 35 | 2.58** | 460.1 [M + H]+ |
| 169 | 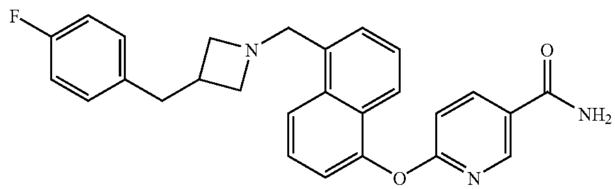 | 6-{5-[3-(4-Fluoro-benzyl)azetidin-1-ylmethyl]-naphthalen-1-yloxy]-nicotinamide | 35 | 2.52** | 442.1 [M + H]+ |
| 170 | 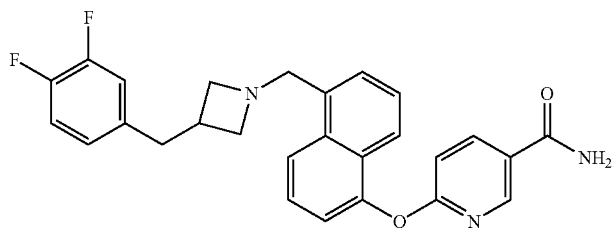 | 6-{5-[3-(3,4-Difluoro-benzyl)azetidin-1-ylmethyl]naphthalen-1-yloxy}nicotinamide | 35 | 2.58** | 460.1 [M + H]+ |
| 171 | 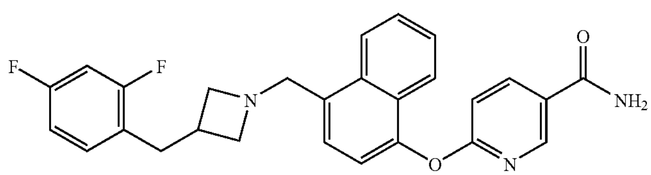 | 6-{4-[3-(2,4-Difluoro-benzyl)azetidin-1-ylmethyl]naphthalen-1-yloxy}nicotinamide | 2 | 2.55* | 460.1 [M + H]+ |
| 172 | 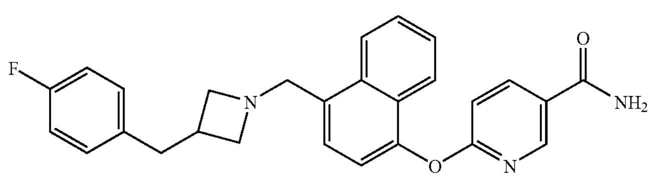 | 6-{4-[3-(4-Fluoro-benzyl)azetidin-1-ylmethyl]naphthalen-1-yloxy}nicotinamide | 2 | 2.56** | 442.1 [M + H]+ |
| 173 | 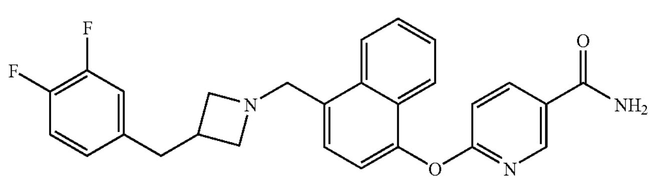 | 6-{4-[3-(3,4-Difluoro-benzyl)azetidin-1-ylmethyl]naphthalen-1-yloxy}nicotinamide | 2 | 2.61** | 460.1 [M + H]+ |

**LCMS Method 2

The biological activity of the compounds of the invention may be tested in the following assay systems:

Competition Binding Assays

Mu-, kappa- or delta-opioid receptor expressing membranes (5-15 μg/well) were suspended in 50 mM Tris buffer pH 7.6 containing 5 mM MgCl$_2$ and were incubated on 96-well plates with test compound or vehicle (1% DMSO) and either 0.5 nM $^3$H-DAMGO, 0.8 nM $^3$H—U-69,595 or 1.1 nM $^3$H-DPDPE respectively in a total volume of 200 μL for 90 min at rt (22° C.). The contents of the wells were filtered and washed 5 times with chilled 50 mM Tris buffer pH 7.6 through H$_2$O pre-soaked GF/B filters using a Perkin Elmer Filtermate. The filters were dried and upon application of scintillant the bound radioactive content for each well determined by scintillation counting in a Wallac TriLux Microbeta scintillation counter. Non-specific binding was determined in the presence of 2 μM Naloxone. $IC_{50}$ values were determined by plotting log concentration test compound against specific binding and subsequent Ki values calculated.

Compounds of the invention demonstrate $K_i$ values of <10000 nM for the mu-opioid receptor in the competition binding assay and preferred compounds, such as Example 16, have $K_i$ of <100 nM at the mu-opioid receptor.

GTPγS Functional Binding Assays

Mu-, kappa- or delta-opioid receptor expressing membranes (5-20 μg/well) were suspended in 50 mM HEPES buffer pH 7.6 containing 3 mM $MgCl_2$, 120 mM NaCl, 150 pM GTPγS, 10 μg/mL saponin and 3 μM GDP (μ-opioid receptor assay) or 5 μM GDP (κ- and δ-opioid receptor assay) and were pre-incubated on 96-well plates with test compound or vehicle (1% DMSO) in a total volume of 160 μL for 10 min at rt (22° C.). Specific agonists DAMGO (10 nM final concentration), U-50,488 (30 nM final concentration) or SNC-80 (10 nM final concentration) were added respectively and the plates pre-incubated for a further 15 min at rt (22° C.) $^{35}$S-GTPγS at a final concentration in the assay of 150 pM was then added to provide a total volume per well of 200 μL and the plates incubated for 45 min at 30° C. The contents of the wells were filtered and washed 5 times with chilled 50 mM Tris buffer pH 7.6 through $H_2O$ pre-soaked GF/B filters using a Perkin Elmer Filtermate. The filters were dried and upon application of scintillant the bound radioactive content for each well determined by scintillation counting in a Wallac TriLux Microbeta scintillation counter. Non-specific binding was determined in the presence of 10 μM GTPγS. $IC_{50}$ values were determined by plotting log concentration test compound against percentage increase over non-stimulated $^{35}$S-GTPγS binding.

Compounds of the invention demonstrate $IC_{50}$ values of <10000 nM for the mu-opioid receptor in the GTPγS assay and preferred compounds, such as Example 16, have $IC_{50}$ of <100 nM at the mu-opioid receptor.

The compounds of the invention preferably demonstrate a degree of selectivity for modulation of the mu-opioid receptor compared to the kappa- and delta-opioid receptors.

In Vivo Feeding Study

The effect of compounds of the invention on body weight and food and water intake was examined in freely-feeding male Sprague-Dawley rats maintained on reverse-phase lighting. Test compounds and reference compounds were dosed orally and measurements made over the following 24 h. Rats were individually housed in polypropylene cages with metal grid floors at a temperature of 21±4° C. and 55±20% humidity. Polypropylene trays with cage pads were placed beneath each cage to detect any food spillage. Animals were maintained on a reverse phase light-dark cycle (lights off for 8 h from 09.30-17.30 h) during which time the room was illuminated by red light. Animals had free access to a standard powdered rat diet and tap water during a two week acclimatization period. The diet was contained in glass feeding jars with aluminum lids. Each lid had a 3-4 cm hole in it to allow access to the food. Animals, feeding jars and water bottles were weighed (to the nearest 0.1 g) at the onset of the dark period. The feeding jars and water bottles were subsequently measured 1, 2, 4, 6 and 24 h after animals were dosed with a compound of the invention and any significant differences between the treatment groups at baseline compared to vehicle-treated controls. Preferred compounds of the invention significantly reduce cumulative food intake, relative to vehicle control, 6 h after administration of compound at 100 mg/kg or less.

What is claimed is:

1. A compound of formula (I), or a pharmaceutically acceptable salt thereof:

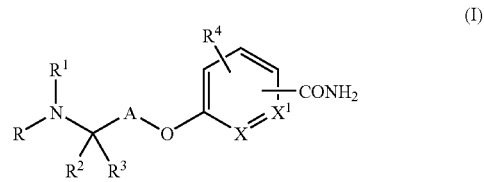

wherein X and $X^1$ are independently CH or N, provided that X and $X^1$ are not both N, and wherein when X is CH the H may be replaced by the $R^4$ group or where $X^1$ is CH the H may be replaced by the $R^4$ group or the —$CONH_2$ substituent;

A is selected from:

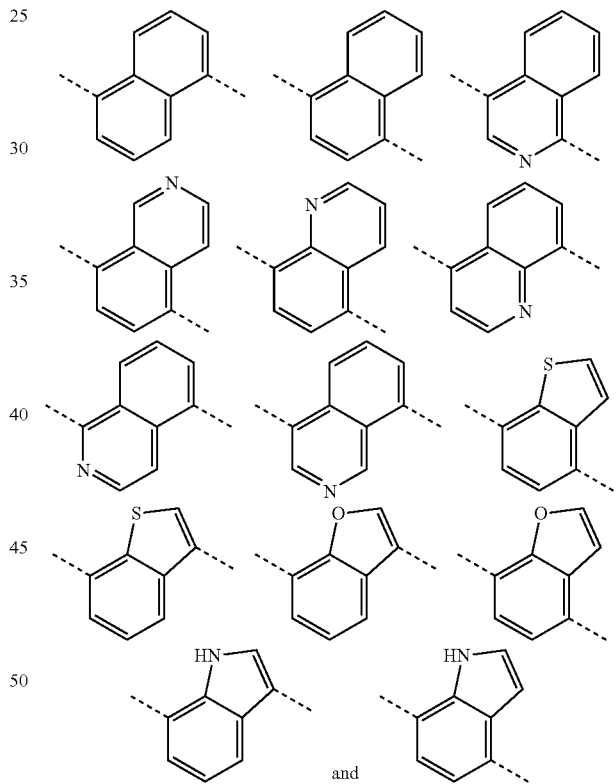

wherein A is optionally substituted with one to three groups selected from nitrile, $C_1$-$C_3$ alkyl, $C_1$-$C_3$ alkoxy, halo, $C_1$-$C_3$ haloalkyl, $C_1$-$C_3$ haloalkoxy, —C(O)$C_1$-$C_3$ alkyl, $C_3$-$C_8$ cycloalkyl and —$C_1$-$C_3$ alkyl $C_3$-$C_8$ cycloalkyl;

R is hydrogen, $C_1$-$C_6$ alkyl or $C_2$-$C_3$ alkylO$C_1$-$C_3$ alkyl;

$R^1$ is $C_1$-$C_6$ alkyl, $C_3$-$C_6$ alkenyl, —$C_1$-$C_6$ alkylaryl, $C_3$-$C_{10}$ cycloalkyl, —$C_1$-$C_6$ alkyl $C_3$-$C_{10}$ cycloalkyl, $C_3$-$C_9$ heterocyclyl, —$C_2$-$C_6$ alkyl-O—$C_3$-$C_9$ heterocyclyl, —$C_1$-$C_6$ alkyl $C_3$-$C_9$ heterocyclyl, —$C_2$-$C_6$ alkyl-O—$C_3$-$C_{10}$ cycloalkyl, —$C_2$-$C_6$ alkyl-O—$C_5$-$C_{10}$ heteroaryl, —$C_1$-$C_6$ alkyl $C_5$-$C_{10}$ heteroaryl, —$C_1$-$C_6$ alkylC(O)C$_1$-C$_6$alkyl, —C$_1$-C$_6$alkylC(O)C$_3$-C$_9$heterocyclyl, —C$_1$-C$_6$ alkylC(O)aryl, —C$_2$-C$_6$ alkyl-O-aryl, —C$_2$-C$_6$ alkyl-O—C$_1$-C$_6$ alkyl, —C$_2$-C$_6$ alkylNR$^6$R$^7$, —(CH$_2$)$_m$C(O)NR$^6$R$^7$ and —(CH$_2$)$_m$NSO$_2$R$^5$; wherein each of the alkyl, alkenyl, cycloalkyl, heterocyclyl, heteroaryl and aryl groups are optionally substituted with one to three groups selected from halo, nitrile, C$_1$-C$_6$ haloalkyl, —S(O)$_n$, C$_1$-C$_6$ alkyl, C$_1$-C$_6$ alkyl, C$_2$-C$_6$ alkenyl, C$_2$-C$_6$ alkynyl, aryl, —C$_1$-C$_6$ alkylaryl, —C(O)C$_1$-C$_6$ alkyl, C$_1$-C$_6$ alkoxy, —O—C$_1$-C$_6$ haloalkyl and hydroxy;

or R and R$^1$ may together with the N atom to which they are attached form a 4- to 7-membered heterocyclic ring optionally containing one further heteroatom selected from N, O and S, which ring may be substituted by one to five groups selected from NR$^8$R$^9$, C$_1$-C$_6$ alkyl, C$_2$-C$_6$ alkenyl, C$_2$-C$_6$ alkynyl, aryl, hydroxy, halo, —C$_1$-C$_6$ alkylaryl, —C$_1$-C$_6$ alkoxy, —C$_1$-C$_6$ alkoxyaryl, aryloxy, —C(O)C$_1$-C$_6$ alkyl, oxo, C$_1$-C$_6$ haloalkyl and —O—(CH$_2$)$_2$—O—, wherein any aryl groups are optionally substituted with one to three halo groups;

R$^2$ and R$^3$ are independently hydrogen or C$_1$-C$_3$ alkyl;

R$^4$ is hydrogen, C$_1$-C$_3$ alkyl, C$_1$-C$_3$ alkoxy, halo, C$_1$-C$_3$ haloalkyl, —C(O)C$_1$-C$_3$ alkyl, —C$_1$-C$_3$ alkyl C$_3$-C$_8$ cycloalkyl or C$_1$-C$_3$ haloalkoxy;

R$^5$ is C$_1$-C$_6$ alkyl, —C$_1$-C$_6$ alkylaryl or —C$_1$-C$_6$ alkyl-O—C$_1$-C$_6$ alkyl;

R$^6$ and R$^7$ are independently hydrogen, C$_1$-C$_6$ alkyl, —C$_1$-C$_6$ alkylaryl, C$_3$-C$_8$ cycloalkyl, —C$_1$-C$_6$ alkyl C$_5$-C$_{10}$ heteroaryl, —C$_1$-C$_6$ alkyl C$_3$-C$_7$ heterocyclyl, —C$_1$-C$_6$ alkylC(O)C$_1$-C$_6$alkyl, —C$_1$-C$_6$alkylC(O)C$_3$-C$_7$heterocyclyl, —C$_1$-C$_6$ alkylC(O)aryl, —C$_1$-C$_6$ alkyl-O-aryl, —C$_2$-C$_6$ alkyl-O—C$_1$-C$_6$ alkyl, —C$_1$-C$_6$ alkyl C$_3$-C$_9$ cycloalkyl; wherein each of the alkyl, cycloalkyl, heterocyclyl, heteroaryl and aryl groups are optionally substituted with one to three groups selected from halo, C$_1$-C$_6$ haloalkyl, —S(O)$_n$C$_1$-C$_6$ alkyl, C$_1$-C$_6$ alkyl, C$_2$-C$_6$ alkenyl, C$_2$-C$_6$ alkynyl, aryl, —C$_1$-C$_6$ alkylaryl, —C(O)C$_1$-C$_6$ alkyl, C$_1$-C$_6$ alkoxy and C$_1$-C$_6$ haloalkoxy;

or R$^6$ and R$^7$ may together with the N atom to which they are attached form a 4- to 7-membered heterocyclic ring optionally containing one further heteroatom selected from N, 0 and S, which ring may be substituted by one to three groups selected from NR$^8$R$^9$, C$_1$-C$_6$ alkyl, C$_2$-C$_6$ alkenyl, C$_2$-C$_6$ alkynyl, aryl, hydroxy, halo, —C$_1$-C$_6$ alkylaryl, —C(O)C$_1$-C$_6$ alkyl, oxo and C$_1$-C$_6$ haloalkyl;

R$^8$ and R$^9$ are independently hydrogen or C$_1$-C$_6$ alkyl;

n is 0, 1, or 2; and m is 1, 2 or 3;

provided that the —CONH$_2$ substituent is not ortho to the —O— group on the phenyl or pyridyl ring.

2. A compound according to claim 1, or a pharmaceutically acceptable salt thereof, wherein X$^1$ is CH.

3. A compound according to claim 1, or a pharmaceutically acceptable salt thereof, wherein A is selected from:

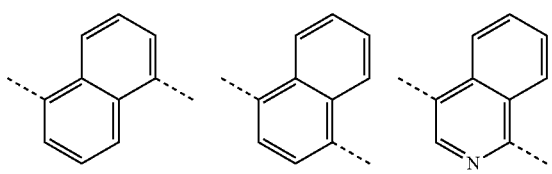

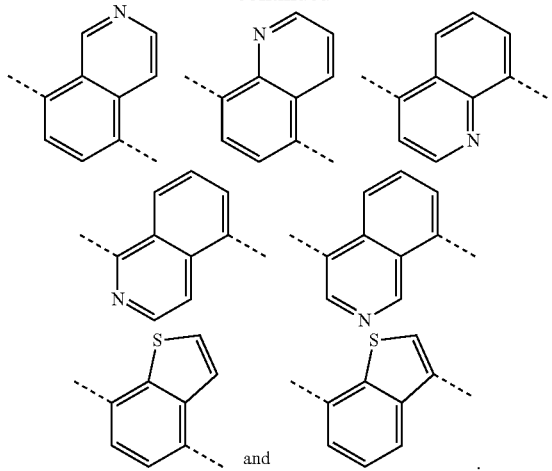

and

4. A compound according to claim 1, or a pharmaceutically acceptable salt thereof, wherein the —CONH$_2$ substituent is para to the —O-group on the phenyl or pyridyl ring.

5. A compound according to claim 1, or a pharmaceutically acceptable salt thereof, wherein R is hydrogen or C$_1$-C$_3$ alkyl.

6. A compound according to claim 1, or a pharmaceutically acceptable salt thereof, wherein R$^1$ is C$_1$-C$_6$ alkyl, C$_1$-C$_6$ alkylaryl, C$_3$-C$_{10}$ cycloalkyl, C$_1$-C$_6$ alkyl C$_3$-C$_{10}$ cycloalkyl, C$_3$-C$_7$ heterocyclyl, C$_1$-C$_6$ alkyl C$_3$-C$_7$ heterocyclyl or C$_1$-C$_6$ alkyl C$_5$-C$_{10}$ heteroaryl; wherein each of the alkyl, cycloalkyl, heterocyclyl, heteroaryl and aryl groups are optionally substituted with one or two groups as described in claim 1.

7. A compound according to claim 1, or a pharmaceutically acceptable salt thereof, wherein R and R$^1$ together with the N atom to which they are attached form a 4- to 7-membered heterocyclic ring, which ring may be substituted by one to three groups selected from NR$^8$R$^9$, C$_1$-C$_6$ alkyl, C$_2$-C$_6$ alkenyl, C$_2$-C$_6$ alkynyl, awl, hydroxy, halo, C$_1$-C$_6$ alkylaryl, C$_1$-C$_6$ alkoxy, C$_1$-C$_6$ alkoxyaryl, aryloxy, C(O)C$_1$-C$_6$ alkyl, oxo and C$_1$-C$_6$ haloalkyl, wherein any aryl groups are optionally substituted with one to three halo groups.

8. A compound according to claim 1, or a pharmaceutically acceptable salt thereof, wherein R$^2$ and R$^3$ are hydrogen.

9. A compound according to claim 1, or a pharmaceutically acceptable salt thereof, wherein R$^4$ is hydrogen or fluoro.

10. A compound according to claim 1, or a pharmaceutically acceptable salt thereof, wherein X is CH, N or CF.

11. A compound of formula (I) selected from:
  6-{4-[(2-Cyclopentylethylamino)methyl]naphthalen-1-yloxy}nicotinamide,
  6-(4-{[2-(Tetrahydropyran-4-yl)ethylamino]methyl}naphthalen-1-yloxy)nicotinamide,
  6-{4-[(3,3-Dimethylbutylamino)methyl]naphthalen-1-yloxy}nicotinamide,
  6-{4-[(3-Methylbutylamino)methyl]naphthalen-1-yloxy}nicotinamide,
  6-{4-[(4,4-Difluorocyclohexylamino)methyl]naphthalen-1-yloxy}nicotinamide,
  6-{4-trans-(4-tert-Butylcychexylamino)methyl]naphthalen-1-yloxy}nicotinamide,
  6-(4-{[(2-Cyclohexylethyl)methylamino]methyl}naphthalen-1-yloxy)nicotinamide,
  6-[4-(Isobutylaminomethyl)naphthalen-1-yloxy]nicotinamide, 6-[4-(Isopropylaminomethyl)naphthalen-1-yloxy]nicotinamide,
6-[4-(Phenethylaminomethyl)naphthalen-1-yloxy]nicotinamide,
6-(4-{[2-(2-Chlorophenyl)ethylamino]methyl}naphthalen-1-yloxy)nicotinamide,
6-{4-[(2-Chlorobenzylamino)methyl]naphthalen-1-yloxy}nicotinamide,
6-{4-[(2-Adamantan-2-ylethylamino)methyl]naphthalen-1-yloxy}nicotinamide,
6-{4-[(4-Methoxycycohexylamino)methyl]naphthalene-1-yloxy}nicotinamide,
6-(4-{[2-(Tetrahydrofuran-2-yl)ethylamino]methyl}naphthalen-1-yloxy)nicotinamide,
6-{4-[(Tetrahydropyran-4-ylamino)methyl]naphthalen-1-yloxy}nicotinamide,
6-{4-[(2-Isopropoxyethylamino)methyl]naphthalen-1-yloxy}nicotinamide,
6-{4-[(2-Dimethylaminoethylamino)methyl]naphthalen-1-yloxy}nicotinamide,
6-{4-[(1-Methylpiperidin-4-ylamino)methyl]naphthalen-1-yloxy}nicotinamide,
6-(4-{[1,5-Dimethyl-1H-pyrrol-2-ylmethyl)amino]methyl}naphthalen-1-yloxy)nicotinamide,
6-[4-(Benzylaminomethyl)naphthalen-1-yloxy]nicotinamide,
6-{4-[(Cyclohexylmethylamino)methyl]naphthalen-1-yloxy}nicotinamide,
6-(4-{[(Tetrahydropyran-2-ylmethyl)amino]methyl}naphthalen-1-yloxy)nicotinamide,
6-(4-{[(Tetrahydropyran-4-ylmethyl)amino]methyl}naphthalen-1-yloxy)nicotinamide,
6-(4-{[2-(4-Methyl-piperidin-1-yl)ethylamino]methyl}naphthalen-1-yloxy)nicotinamide,
6-(4-{[2-(4-Methylpiperazin-1-yl)ethylamino]methyl}naphthalen-1-yloxy)nicotinamide,
6-{4-[(cis-4-Isopropylcyclohexylamino)methyl]naplithalen-1-yloxy}nicotinamide,
6-{4-[(1-Oxaspiro-[4.4]non-3-ylamino)methyl]naphthalen-1-yloxy}nicotinamide,
6-(4-{[(S)-(1-Oxaspiro[4.4]non-3-yl)amino]methyl}naphthalen-1-yloxy)nicotinamide,
6-(4-{[(R)-(1-Oxaspiro[4.4]non-3-yl)amino]methyl}naphthalen-1-yloxy)nicotinamide,
6-(4-[(1-Cyclopropylpiperidin-4-ylamino)methyl]naphthalen-1-yloxy}nicotinamide,
6-{4-[cis-(4-Methylcyclohexylamino)methyl]naphthalen-1-yloxy}nicotinamide,
6-{4-[trans-(4-Methylcyclohexylamino)methyl]naphthalen-1-yloxy}nicotinamide,
6-{4-[cis-(4-Phenylcychexylamino)methyl]napalen-1-yloxy}nicotinamide,
6-{4-[cis-(4-Propylcyclohexylamino)methyl]naphthalen-1-yloxy}nicotinamide,
6-(4-{[cis-4-(1,1-Dimethylpropyl)cyclohexylamino]methyl}naphthalen-1-yloxy)nicotinamide,
6-{4-[trans-(4-Propylcyclohexylamino)methyl]naphthalen-1-yloxy}nicotinamide,
6-{4-[cis-(4-Phenylcyclohexylamino)methyl]naphthalen-1-yloxy}nicotinamide,
6-{4-[(2-Hydroxy-2-phenylethylamino)methyl]naphthalen-1-yloxy}nicotinamide,
6-(4-{[(1-Hydroxycyclohexylmethyl)amino]methyl}naphthalen-1-yloxy)nicotinamide,
6-[4-(4-Methylpiperidin-1-ylmethyl)naphthalen-1-yloxy]nicotinamide,
6-[4-(4-Hydroxymethylpiperidin-1-ylmethy)naphthalen-1-yloxy]nicotinamide,
6-{-4-[(3-Piperidin-1-yl-propylamino)methyl]naphthalen-1-yloxyl}nicotinamide,
6-{4-[(4-Diethylaminocyclohexylamino)methyl]naphthalen-1-yloxy}nicotinamide,
6-{4-[1,4-Dioxa-8-aza-spiro[4.5]dec-8-ylmethyl]naphthalen-1-yloxy}nicotinamide,
6-{4-[2-Morpholin-4-ylethylamino)methyl]naphthalen-1-yloxy}nicotinamide,
6-{4-[(1,2,2,6,6-Pentamethylpiperidin-4-ylamino)methyl]naphthalene-1-yloxy}nicotinamide,
6-(4-{[(5-Ethyl-1-aza-bicyclo[2.2.2]oct-2-ylmethyl)amino]methyl}naphthalen-1-yloxy)nicotinamide,
6-[4-(1,3-Dihydroisoindol-2-ylmethyl)naphthalen-1-yloxy]nicotinamide,
6-(4-Piperidin-1-ylmethylnaphthalen-1-yloxy)nicotinamide,
6-{4-[((R)-2-Hydroxy-2-phenylethylamino)methyl]naphthalen-1-yloxy}nicotinamide,
6-{5-[(2-Cyclopentylethyl amino)methyl]naphthalen-1-yloxy}nicotinamide,
6-{5-(Phenethylaminomethyl)naphthalen-1-yloxy}nicotinamide,
6-{5-[(Cyclohexylmethylamino)methyl]naphthalen-1-yloxy}nicotinamide,
6-{5-[(2-Thiophen-2-ylethylamino)methyl]naphthalen-1-yloxy}nicotinamide,
6-(5-Cyclohexylaminomethylnaphthalen-1-yloxy)nicotinamide
6-{5-[cis-(4-Propylcyclohexylamino)methyl]naphthalen-1-yloxy}nicotinamide,
6-[4-(4-Methylpiperazin-1-ylmethyl)naphthalen-1-yloxy]nicotinamide,
6-[4-(4-Ethylpiperazin-1-ylmethyl)naphthalen-1-yloxy]nicotinamide,
6-{4-[(3-Methylbutylamino)methyl]naphthalen-1-yloxy}nicotinonitrile,
6-[4-((S)-Indan-1-ylaminomethyl)naphthalen-1-yloxy]nicotinamide,
6-[4-((R)-Indan-1-ylaminomethyl)naphthalen-1-yloxy]nicotinamide,
6-{4-[(5,6-Difluoroindan-2-ylamino) methyl]naphthalen-1-yloxy}nicotinamide,
6-[5-((R)-Indan-1-ylaminomethyl)naphthalen-1-yloxy]nicotinamide,
6-[5-((S)-Indan-1-ylaminomethyl)naphthalen-1-yloxy]nicotinamide,
6-{5-[(3-Methylbutylamino)methyl]quinolin-8-yloxy}nicotinamide,
6-{5-[(2-Cyclohexylethylamino)methyl]quinolin-8-yloxy}nicotinamide,
6-{5-[cis-(4-tert-Butylcyclohexylamino)methyl]quinolin-8-yloxy}nicotinamide,
6-{5-[trans-(4-tert-Butylcyclohexylamino)methyl]quinolin-8-yloxy}nicotinamide,
6-{5-[(3,3-Dimethylbutylamino)methyl]naphthalen-1-yloxy}nicotinamide,
6-{5-[(2-Isopropoxyethylamino)methyl]naphthalen-1-yloxy}nicotinamide,
6-(5-{[2-(Tetrahydrofuran-2-yl)ethylamino]methyl}naphthalen-1-yloxy)nicotinamide,
6-(5-{[2-(Tetrahydropyran-4-yl)ethylamino]methyl}naphthalen-1-yloxy)nicotinamide
6-{5-[((R)-2-Hydroxy-2-ethenylethylamino)methyl]naphthalen-1-yloxy}nicotinamide, 6-(5-{[2-(Tetrahydropyran-2-yl)ethylamino]
methyl}naphthalen-1-yloxy)nicotinamide,
6-{5-[(1-Oxaspiro-[4.4]non-3-ylamino)methyl]naphthalen-1-yloxy}nicotinamide,
6-{5-[((S)-2-Hydroxy-2-phenylethylamino)methyl]naphthalen-1-yloxy}nicotinamide,
6-{5-[(4,4-Dimethylcyclohexylamino)methyl]naphthalen-1-yloxy}nicotinamide,
3-Fluoro-4-(5-{[2-(tetrahydrofuran-4-yl)ethylamino]
methyl}naphthalen-1-yloxy)benzamide,
3-Fluoro-4-(4-{[2-(tetrahydropyran-4-yl)ethylamino]
methyl}naphthalen-1-yloxy)benzamide,
6-{4-[(3-Methylbutylamino)methyl]benzofuran-7-yloxy}nicotinamide,
6-{4-[(3-Methylbutylamino)methyl]benzo[b]thiophen-7-yloxy}nicotinamide,
6-[4-(4-Hydroxy-4-phenylpiperidin-1-ylmethyl)naphthalen-1-yloxy]nicotinamide,
6-{4-[(1-Isopropylpiperidin-4-ylamino)methyl]naphthalen-1-yloxy}nicotinamide,
6-{4-[((R)-2-Phenylpropylamino)methyl]naphthalen-1-yloxy}nicotinamide,
6-{4-[((R)-3-Trifluoromethylcyclohexylamino)methyl]
naphthalen-1-yloxy}nicotinamide,
6-[4-((1R,2S,4S)-Bicyclo[2.2.1]hept-2-ylaminomethyl)
naphthalen-1-yloxy]nicotinamide,
6-{4-[((1S,2S,3S,5R)-2,6,6-Trimethylbicyclo[3.1.1]hept-3-ylamino)methyl]naphthalen-1-yloxy}nicotinamide,
3-Fluoro-4-{4-[(3-methylbutylamino)methyl]naphthalen-1-yloxy}benzamide,
6-{5-[(3-Methylbutylamino)methyl]naphthalen-1-yloxy}nicotinamide,
6-(5-{[Bis(3-methylbutyl)amino]methyl}naphthalen-1-yloxy)nicotinamide,
6-[5-(Indan-2-ylaminomethyl)naphthalen-1-yloxy]nicotinamide,
6-{5-[(2-Cyclohexylethylamino)methyl]naphthalen-1-yloxy}nicotinamide,
6-{5-[trans-(4-tert-Butylcyclohexylamino)methyl]naphthalen-1-yloxy}nicotinamide,
4-{4-[(3-Methylbutylamino)methyl] isoquinolin-1-yloxy}benzamide,
4-{4-[(2-Cyclohexylethylamino)methyl]isoquinolin-1-yloxy}benzamide,
4-(4-{2-(Tetrahydropyran-4-yl)ethylamino]methylisoquinolin-1-yloxy}benzamide,
6-{1-[(3-Methylbutylamino)methyl]isoquinolin-4-yloxy}nicotinamide,
6-{1-[(trans-4-Isopropylcyclohexylamino)methyl]isoquinolin-4-yloxy}nicotinamide,
6-{1-[(2-Cyclohexylethylamino)methyl]isoquinolin-4-yloxyl}nicotinamide,
6-[1-(Indan-2-ylaminomethyl)isoquinolin-4-yloxy]nicotinamide,
6-(5-{[(2,2-Dimethylcyclopropylmethyl)amino]methyl]
naphthalene-1-yloxy}nicotinamide,
3-Fluoro-4-[1-(indan-2-ylaminomethyl)isoquinolin-4-yloxy]benzamide,
6-{4-[(2-Piperidin-1-yl-ethylamino)methyl]naphthalen-1-yloxy}nicotinamide,
6-(4-{[2-(2-Methylpiperidin-1-yl)ethylamino]methyl
naphthalen-1-yloxy)nicotinamide,
6-(4-[2-(3-Methylpiperidin-1-yl)ethylamino]
methyl}naphthalen-1-yloxy)nicotinamide,
6-{4-[(2-Pyrrolidin-1-ylethylamino)methyl]naphthalen-1-yloxy}nicotinamide,
6-(4-{[2-(Tetrahydropyran-2-yl)ethylamino]
methyl}naphthalen-1-yloxy)nicotinamide,
6-{5-[(4,4-Difluorocyclohexylamino)methyl]naphthalen-1-yloxy}nicotinamide,
6-{5-[(2-Cyclopropylethylamino)methyl]naphthalen-1-yloxy}nicotinamide,
6-(5-{[cis-4-(1,1-Dimethylpropy)cyclohexylamino]
methyl}naphthalen-1-yloxy)nicotinamide,
6-{4-[(4-Trifluoromethylcyclohexylamino)methyl]naphthalen-1-yloxy}nicotinamide,
6-{5-[trans-(4-Isopropylcycloexylamino)methyl]naphthalen-1-yloxy}nicotinamide,
6-{5-[(Tetrahydropyran-3-ylamino)methyl]naphthalen-1-yloxy}nicotinamide,
6-(5-{[(-Hydroxycyclohexylmethyl)amino]
methyl}naphthalen-1-yloxy)nicotinamide,
6-{4-[(Tetrahydropyran-3-ylamino)methyl]naphthalen-1-yloxy}nicotinamide,
6-(4-{[(2,2-Dimethylcyclopropylmethy)amino]
methyl}naphthalen-1-yloxy)nicotinamide,
6-{4-[(2-Cyclopropylethylamino)methyl]naphthalen-1-yloxy}nicotinamide,
6-{4-[(3-Hydroxy-3-methylbutylamino)methyl]naphthalen-1-yloxy}nicotinamide,
6-{4-[(2-Cyclohexylethylamino)methyl]naphthalen-1-yloxy}nicotinamide,
6-{4-[(4,4-Dimethylcyclohexylamino)methyl]naphthalen-1-yloxy}nicotinamide,
6-{4-[trans-(4-Isopropylcyclohexylamino)methyl]naphthalen-1-yloxy}nicotinamide,
6-[4-(Indan-2-ylaminomethyl)naphthalen-1-yloxy]nicotinamide,
6-{4-[(4-Hydroxycyclohexylamino)methyl]naphthalen-1-yloxy}nicotinamide,
6-{4-[trans-(4-Phenylcyclohexylamino)methyl]naphthalen-1-yloxy}nicotinamide,
6-(4-{[trans-4-(1,1-Dimethylpropyl)cyclohexylamino]
methyl}naphthalen-1-yloxy)-nicotinamide,
6-{5-[(5-Fluoroindan-2-ylamino)methyl]naphthalen-1-yloxy}nicotinamide,
6-(5-{trans-[4-(1,1-Dimethylpropyl)cyclohexylamino]
methyl}naphthalen-1-yloxy)-nicotinamide,
6-{5-[(5-Fluoroindan-2-ylamino)methyl]naphthalen-1-yloxy}nicotinamide,
6-[4-({Methyl-[2-(tetrahydropyran-4-yl)ethyl]
amino}methyl)naphthalen-1-yloxy]nicotinamide,
6-{4-[(2-Cyclohexylethylamino)methyl]benzo[b]
thiophen-7-yloxy}nicotinamide,
6-{4-[(2-Cyclohexylethylamino)methyl]benzofuran-7-yloxy}nicotinamide,
3-Chloro-4-{4-[(3-methylbutylamino)methyl]naphthalen-1-yloxy}benzamide,
4-{4-[(3-Methylbutylamino)methyl]naphthalene-1-yloxy}benzamide,
4-{8-[(3-Methylbutylamino)methyl]quinolin-4-yloxy}benzamide,
6-{4-[(3-Methylbutylamino)methyl]naphthalene-1-yloxy}pyridine-2-carboxamide,
2-{4-[(3-Methylbutylamino)methyl]naphthalen-1-yloxy}isonicotinamide,
6-[5-(4,4-Difluoropiperidin-1-ylmethyl)naphthalen-1-yloxy]nicotinamide,
6-[5-(3-Methylazetidin-1-ylmethyl)naphthalen-1-yloxy]
nicotinamide,
6-[5-(4-Trifluoromethylpiperidin-1-ylmethyl)naphthalen-1-yloxy]nicotinamide, 6-[5-(3-Fluoroazetidin-1-ylmethyl)naphthalen-1-yloxy]nicotinamide,
6-[5-(3-Benzylazetidin-1-ylmethyl)naphthalen-1-yloxy]nicotinamide,
6-(5-Piperidin-1-ylmethylnaphthalen-1-yloxy)nicotinamide,
6-[5-(3-Methoxyazetidin-1-ylmethyl)naphthalen-1-yloxy]nicotinamide,
6-(5-Pyrrolidin-1-ylmethylnaphthalen-1-yloxy)nicotinamide,
6-[5-(3-Phenoxyazetidin-1-ylmethyl)naphthalen-1-yloxy]nicotinamide,
6-[5-(4-Methylpiperidin-1-ylmethyl)naphthalen-1-yloxy]nicotinamide,
6-[5-(3-Propoxyazetidin-1-ylmethyl)naphthalen-1-yloxy]nicotinamide,
6-{5-[3-(3-Fluorophenoxy)azetidin-1-ylmethyl]naphthalen-1-yloxy}nicotinamide,
6-{5-[3-(4-Fluorophenoxy)azetidin-1-ylmethyl]naphthalen-1-yloxy}nicotinamide,
6-[5-((S)-3-Methylpyrrolidin-1-ylmethyl)naphthalen-1-yloxy]nicotinamide,
6-[5-((R)-3-Methylpyrrolidin-1-ylmethyl)naphthalen-1-yloxy]nicotinamide,
6-[4-(4,4-Difluoropiperidin-1-ylmethyl)naphthalen-1-yloxy]nicotinamide,
6-[4-(3-Methylazetidin-1-ylmethyl)naphthalen-1-yloxy]nicotinamide,
6-[4-(4-Trifluoromethylpiperidin-1-ylmethyl)naphthalen-1-yloxy]nicotinamide
6-[4-(3-Fluoroazetidin-1-ylmethyl)naphthalen-1-yloxy]nicotinamide,
6-[4-(3-Benzylazetidin-1-ylmethyl)naphthalen-1-yloxy]nicotinamide,
6-[4-(3-Methoxyazetidin-1-ylmethyl)naphthalen-1-yloxy]nicotinamide,
6-(4-Pyrrolidin-1-ylmethylnaphthalen-1-yloxy)nicotinamide,
6-[4-(3-Phenoxyazetidin-1-ylmethyl)naphthalen-1-yloxy]nicotinamide,
6-[4-(3-Propoxyazetidin-1-ylmethyl)naphthalen-1-yloxy]nicotinamide,
6-{4-[3-(3-Fluorophenoxy)azetidin-1-ylmethyl]naphthalene-1-yloxy}nicotinamide,
6-{4-[3-(4-Fluorophenoxy)azetidin-1-ylmethyl]naphthalen-1-yloxy}nicotinamide,
6-[4-((S)-3-Methylpyrrolidin-1-ylmethyl)naphthalen-1-yloxy]nicotinamide,
6-[4-((R)-3-Methylpyrrolidin-1-ylmethyl)naphthalen-1-yloxy]nicotinamide,
6-{5-[3-(2,4-Difluorobenzyl)azetidin-1-ylmethyl]naphthalen-1-yloxy}nicotinamide,
6-{5-[3-(4-Fluorobenzyl)azetidin-1-ylmethyl]naphthalen-1-yloxy}nicotinamide,
6-{5-[3-(3,4-Difluorobenzyl)azetidin-1-ylmethyl]naphthalen-1-yloxy}nicotinamide,
6-{4-[3-(2,4-Difluorobenzyl)azetidin-1-ylmethyl]naphthalen-1-yloxy}nicotinamide,
6-{4-[3-(4-Fluorobenzyl)azetidin-1-ylmethyl]naphthalen-1-yloxy}nicotinamide, and
6-{4-[3-(3,4-Difluorobenzyl)azetidin-1-ylmethyl]naphthalen-1-yloxy}nicotinamide, or a pharmaceutically acceptable salt of any one thereof.

12. A pharmaceutical composition comprising a compound according to claim 1, or a pharmaceutically acceptable salt thereof and a pharmaceutically acceptable carrier.

\* \* \* \* \*